(12) United States Patent
Beck et al.

(10) Patent No.: US 12,595,452 B2
(45) Date of Patent: Apr. 7, 2026

(54) SYSTEM AND METHOD FOR THE PRODUCTION OF BIOMOLECULES

(71) Applicant: UNIVERCELLS TECHNOLOGIES S.A., Nivelles (BE)

(72) Inventors: Sarah Beck, Nivelles (BE); Christophe Dumont, Haine-Saint-Pierre (BE); Thibault Poncelet, Nivelles (BE); Alexandre Vanhaver, Braine le Château (BE); Jean-Christophe Drugmand, Wavre (BE); Andy Reniers, Nivelles (BE); Laetitia De Viron, Ecaussinnes (BE)

(73) Assignee: UNIVERCELLS TECHNOLOGIES SA, Nivelles (BE)

(*) Notice: Subject to any disclaimer, the term of this patent is extended or adjusted under 35 U.S.C. 154(b) by 624 days.

(21) Appl. No.: 17/928,416

(22) PCT Filed: May 31, 2021

(86) PCT No.: PCT/EP2021/064554
§ 371 (c)(1),
(2) Date: Nov. 29, 2022

(87) PCT Pub. No.: WO2021/240016
PCT Pub. Date: Dec. 2, 2021

(65) Prior Publication Data
US 2023/0203418 A1 Jun. 29, 2023

Related U.S. Application Data

(60) Provisional application No. 63/130,002, filed on Dec. 23, 2020, provisional application No. 63/031,961, filed on May 29, 2020.

(51) Int. Cl.
*C12M 1/00* (2006.01)
*C12M 1/12* (2006.01)

(52) U.S. Cl.
CPC ............ *C12M 23/52* (2013.01); *C12M 23/34* (2013.01); *C12M 25/18* (2013.01)

(58) Field of Classification Search
CPC ...... C12M 23/52; C12M 23/34; C12M 25/18; C12M 25/04; C12M 25/06; C12N 5/0602
(Continued)

(56) References Cited

U.S. PATENT DOCUMENTS

2015/0175950 A1 6/2015 Hirschel
2015/0368600 A1 12/2015 Norey et al.
(Continued)

FOREIGN PATENT DOCUMENTS

CN 201605192 U 10/2010
CN 106399074 A 2/2017
(Continued)

*Primary Examiner* — Michael L Hobbs
*Assistant Examiner* — Lenora A Abel
(74) *Attorney, Agent, or Firm* — Dickinson Wright PLLC; Andrew D. Dorisio; Nicholas P. Coleman

(57) ABSTRACT

The current invention relates to a bioreactor cabinet, configured to be incorporated in a biomolecule production system, wherein said bioreactor cabinet is preferably a mobile bioreactor cabinet suited to receive a bioreactor, said bioreactor cabinet is provided with a bioreactor docking station, wherein said bioreactor cabinet, more preferably a side wall of said bioreactor cabinet, is provided with a connector allowing the transmission of power, signals and/or data when paired with a biomolecule production system, such as a bioreactor chamber of said system. The current invention equally relates to a biomolecule production system and methods for producing biomolecules.

15 Claims, 33 Drawing Sheets

(58) Field of Classification Search
USPC ...................................................... 435/289.1
See application file for complete search history.

(56)                        References Cited

U.S. PATENT DOCUMENTS

| | | | |
|---|---|---|---|
| 2016/0304824 A1* | 10/2016 | Mahajan ................ | C12M 23/28 |
| 2019/0241375 A1* | 8/2019 | Guarracina .......... | B65G 47/905 |
| 2019/0330579 A1 | 10/2019 | Guenat | |
| 2021/0009933 A1* | 1/2021 | Castillo ................. | C12M 33/02 |

FOREIGN PATENT DOCUMENTS

| | | | |
|---|---|---|---|
| CN | 107002014 A | 8/2017 | |
| CN | 109321450 A | 2/2019 | |
| CN | 109996863 A | 7/2019 | |
| CN | 114032167 A | 2/2022 | |
| WO | 2005076093 A1 | 8/2005 | |
| WO | 2019072584 A1 | 4/2019 | |
| WO | 2019122239 A1 | 6/2019 | |
| WO | 2019175442 A1 | 9/2019 | |
| WO | 2020020569 A1 | 1/2020 | |

* cited by examiner

A

B

SYSTEM AND METHOD FOR THE PRODUCTION OF BIOMOLECULES

FIELD OF THE INVENTION

The invention pertains to the technical field of the production of biomolecules such as viral vaccines, antibodies or gene therapy products and describes a system and method thereto.

BACKGROUND

Biomolecules are increasingly gaining importance in the world of pharmaceuticals. Antibody-based therapies and RNA, DNA and gene therapies are deemed to provide a solution for many, hitherto not treatable diseases. In addition, due to the emergence of new viral infections such as SARS, SARS-CoV-2 and MERS, the demand for vaccine production facilities have risen.

The traditional methods of producing and purifying biomolecules from cultured cells are tedious and time consuming, rendering the cost of biomolecule production too high. In addition, they often require large facilities, which again has a negative effect on the production efficiency, the overall time for production and the total cost.

In order to obtain products suitable for clinical administration, fast and efficient methods of producing biomolecules are needed. In addition, there is a need for systems that are concise and require a minimum amount of space and which can be easily transported, for instance to be placed on a bench or in a laminar flow cabinet.

The present disclosure aims to resolve at least some of the problems mentioned above. More specifically, it aims to provide a concise and modular biomolecule production system, suited for the production of viral particles, proteins and gene therapy products that can be used for clinical and therapeutic purpose.

The present disclosure provides a system and solutions adapted for the production and/or purification of biomolecules which allow the low-cost manufacture of biomolecules such as cells, DNA, RNA, proteins, peptides and virus products while still maintaining the high quality requirements. The disclosure allows the production of biomolecules under GMP conditions. Second, it is also the aim to provide an ergonomic, highly accessible and user-friendly system which is flexible and preferably modular. Finally, it is also the aim of the current disclosure to provide a methodology that allows a limited amount of operational steps while still providing a high yield of biomolecule, with a significant reduction of operation expenses (OPEX) and a high level of containment.

SUMMARY OF THE INVENTION

The present disclosure serves to provide a solution to one or more of above-mentioned disadvantages. To this end, the present disclosure provides a bioreactor cabinet according to claim 1. More in particular, the disclosure provides a bioreactor cabinet configured to be incorporated in a biomolecule production system, wherein said bioreactor cabinet is preferably a wheeled (or otherwise mobile) bioreactor cabinet suited to receive a bioreactor, said bioreactor cabinet is provided thereto with a bioreactor docking station, wherein said bioreactor cabinet, more preferably a sidewall of said cabinet, is provided with a connector allowing the transmission of power, signals and/or data when paired with a biomolecule production system, such as a bioreactor chamber of said biomolecule production system.

Preferred embodiments of the bioreactor cabinet are shown in any of the claims. The bioreactor cabinet is compact and requires a minimum of space and can be easily transported.

In a second aspect, the present disclosure provides a system for producing biomolecules said system comprises:
  at least one process chamber comprising one or more purification or filtration devices allowing the purification or filtration of a biomolecule of a cell harvest
  and a bioreactor chamber, suited to receive a bioreactor, wherein said bioreactor chamber is provided with a connector allowing the transmission of power, signals and/or data when paired with a bioreactor cabinet comprising a bioreactor.

The present disclosure also discloses a system for producing biomolecules said system comprising:
  a process chamber comprising one or more purification or filtration devices allowing the purification or filtration of a biomolecule of a cell harvest,
  a downstream chamber
  and a bioreactor chamber, suited to receive a bioreactor, wherein said bioreactor chamber is positioned in between said process chamber and said downstream chamber, and is fluidly connected to one or more chambers, wherein said bioreactor chamber is provided with a connector allowing the transmission of power, signals and/or data when paired with a bioreactor cabinet.

In a last aspect the present disclosure discloses a method for producing a biomolecule, such as a protein, a virus or viral particle, or gene therapy product, comprising the steps of:
  providing a bioreactor provided in a bioreactor cabinet, preferably a mobile/wheeled bioreactor cabinet, that docks into a bioreactor chamber of a biomolecule production system
  and wherein a harvest from said bioreactor is purified in a processing chamber flanking said bioreactor chamber to produce a biomolecule harvest.

In an embodiment, said biomolecule harvest is further concentrated by means of a concentrator located in said bioreactor chamber.

In a further aspect the present disclosure discloses a method of docking a bioreactor cabinet into a chamber of a biomolecule production system, said method comprising providing a connection between said cabinet and system by means of a connector allowing the transmission of power, signals and/or data when paired.

The systems and method according to the present disclosure allow the low-cost manufacture of biomolecules such as virus products while still maintaining the high quality requirements. In addition, the present disclosure allows the production of biomolecules under GMP conditions and provides an ergonomic, highly accessible and user-friendly system. Finally, the current disclosure provides a methodology that allows a limited amount of operational steps while still providing a high yield of biomolecule, with a significant reduction of operation expenses (OPEX) and a high level of containment.

US 12,595,452 B2

3

Figure 1A:
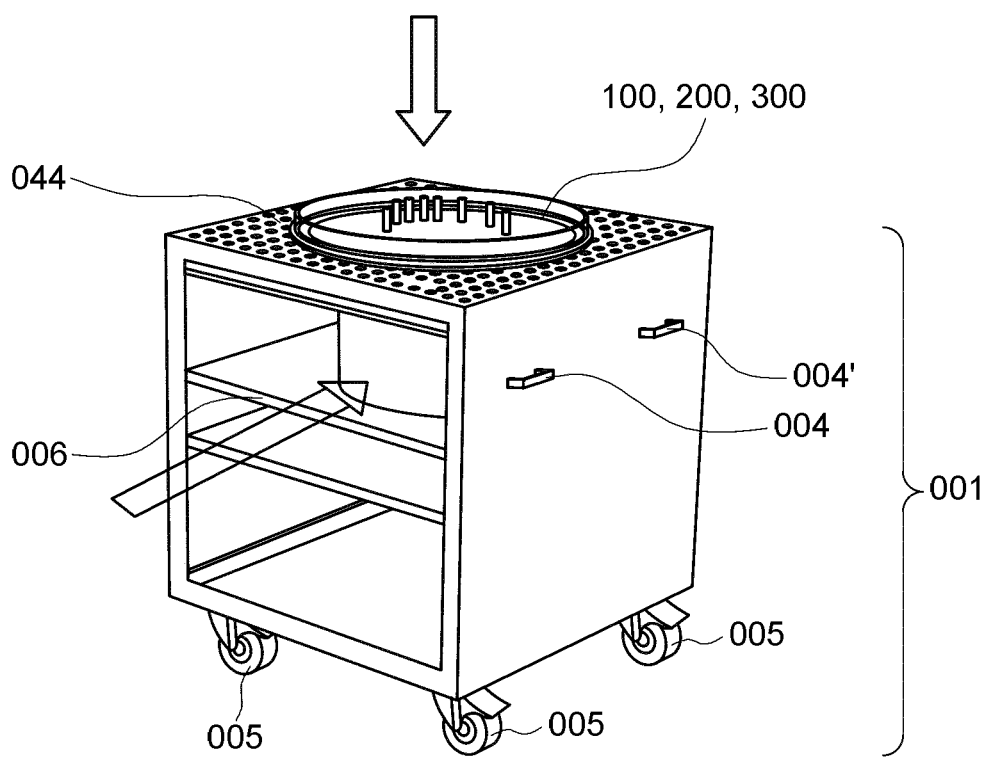
FIGS. 1A, 1B and 1C illustrate different embodiments of a bioreactor cabinet according to the current disclosure.
Figure 1B:
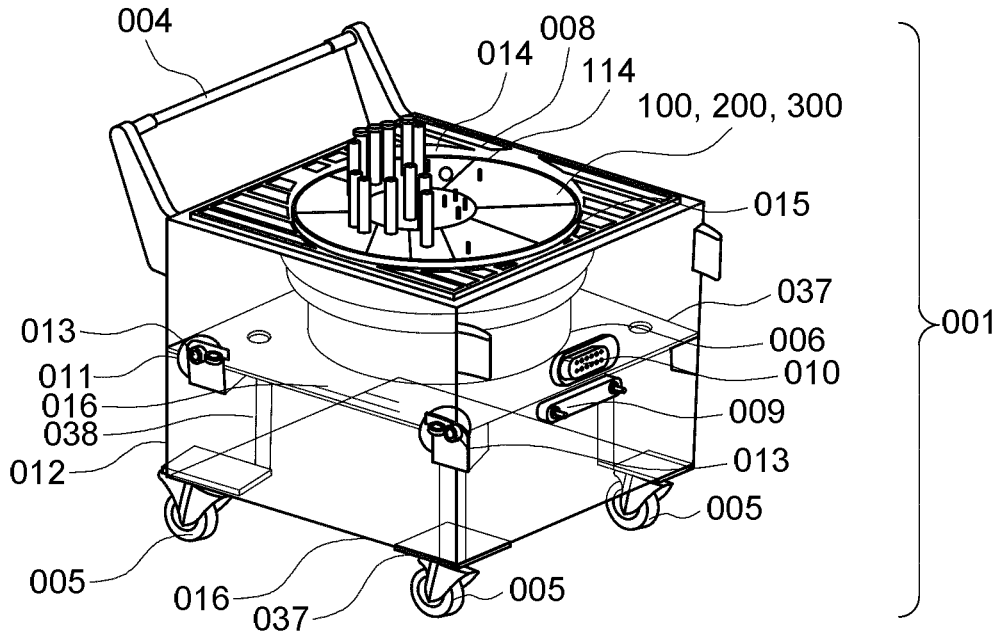
Figure 1C:
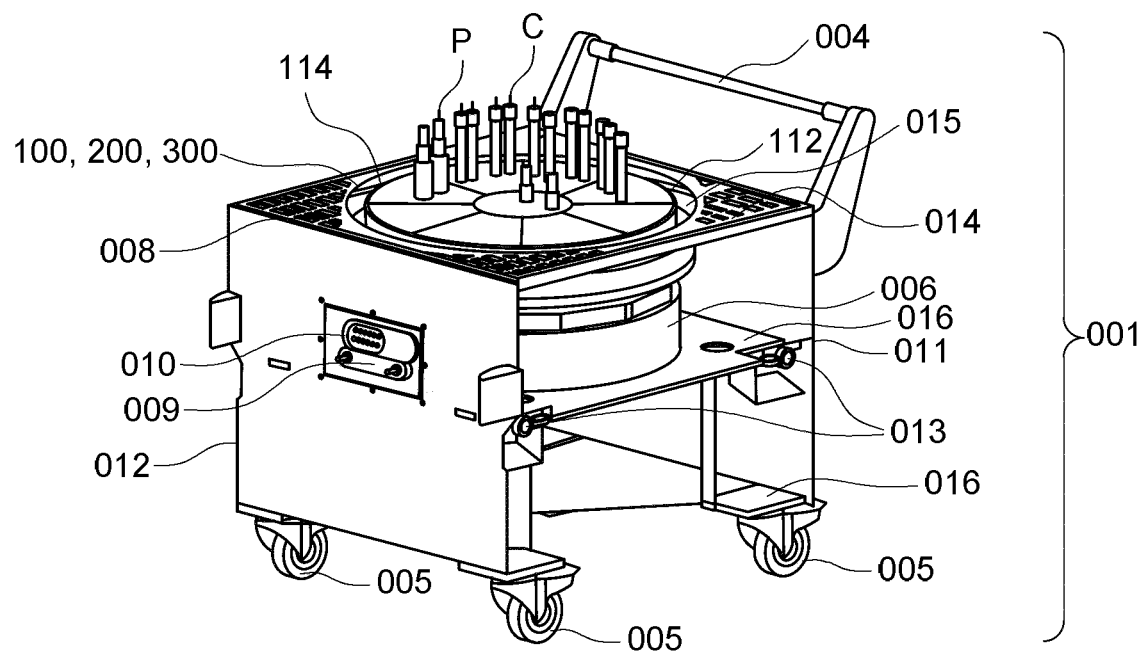
Figure 1D:
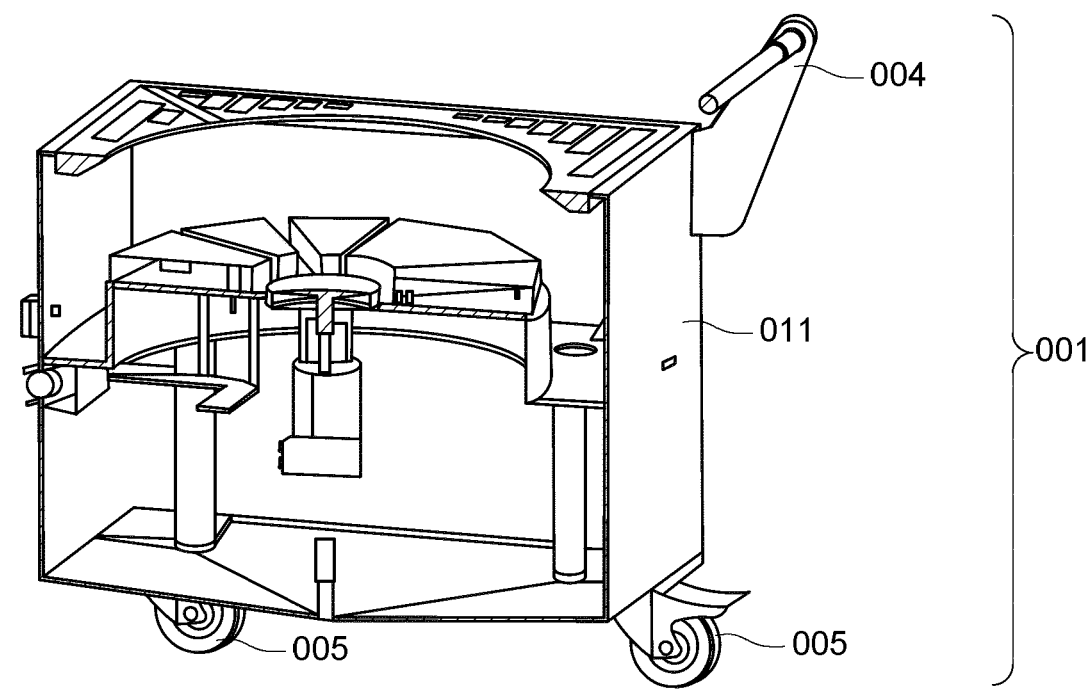
Figure 1E:
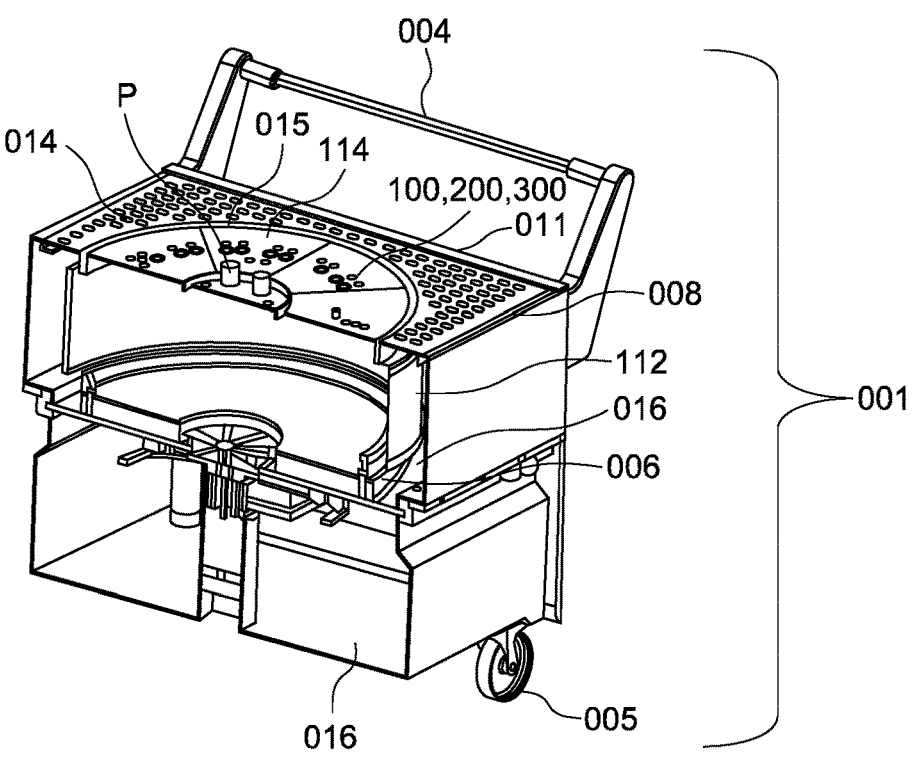
Figure 1F:
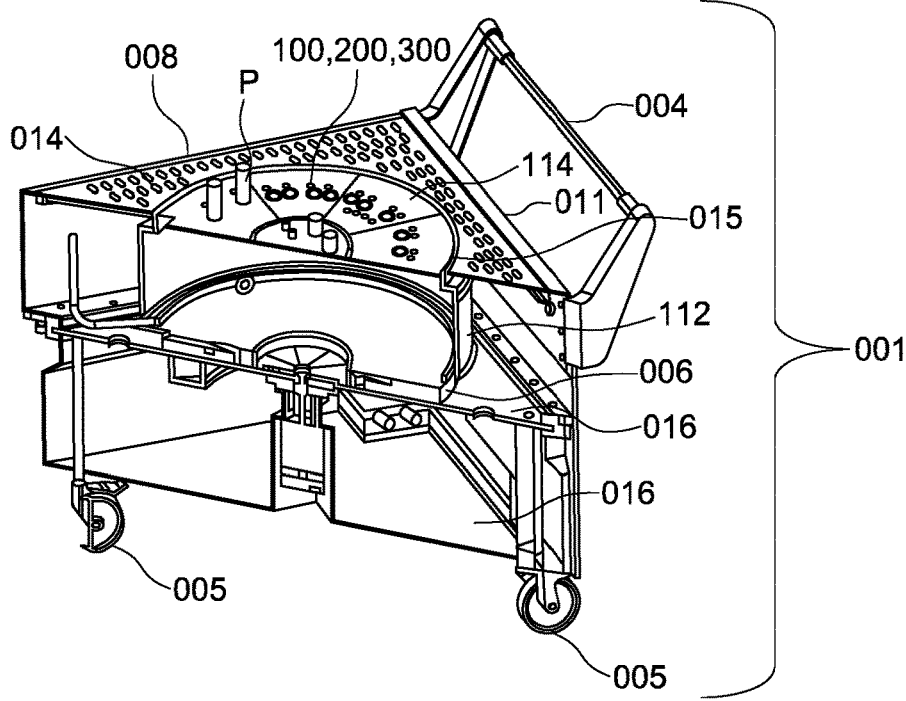

FIGS. 1D, 1E and 1F show a cross section of an embodiment of a bioreactor cabinet according to the current disclosure.

Figure 2:
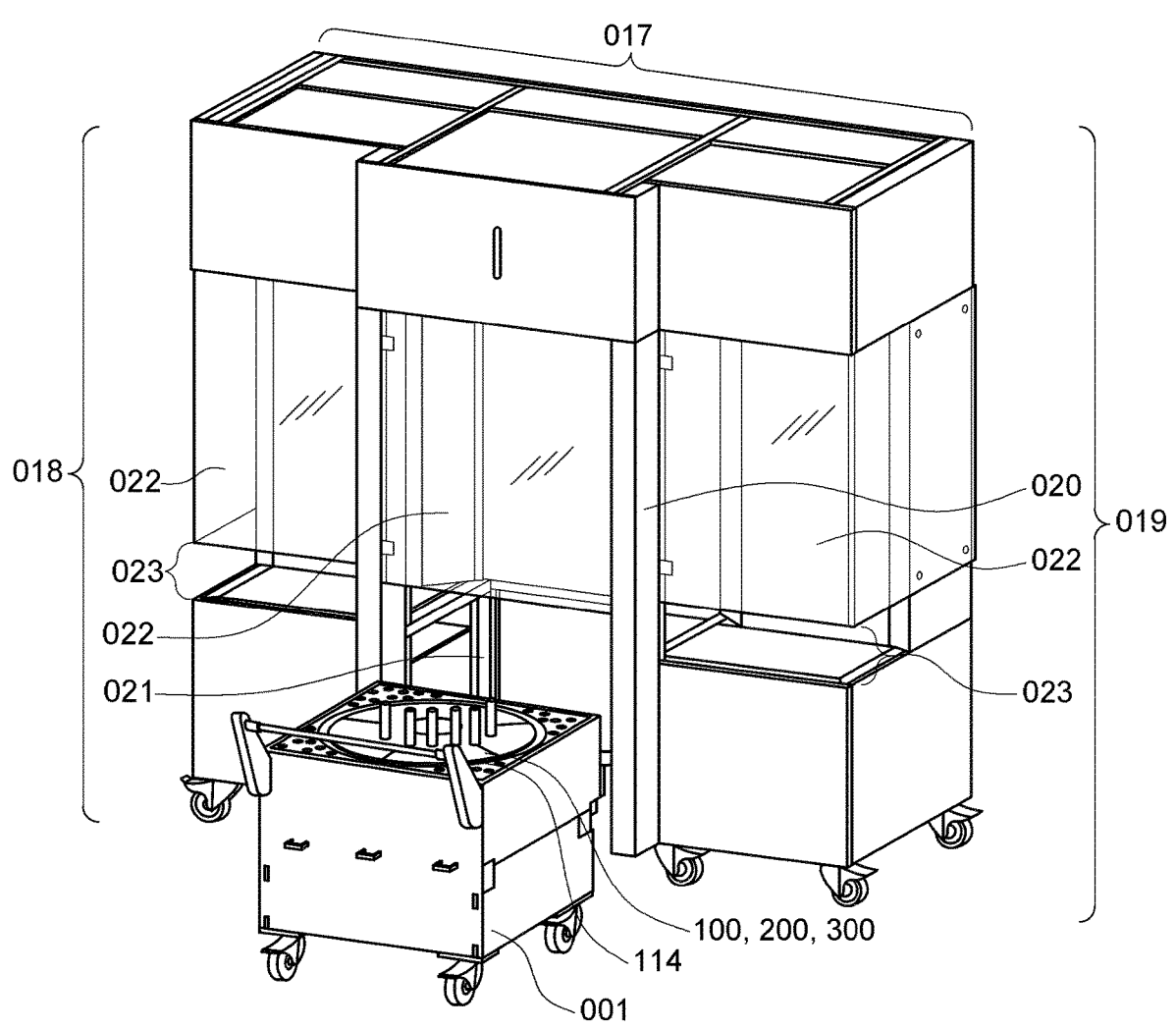

FIG. 2 illustrates a front view of an embodiment of the system according to the current disclosure.

Figure 3:
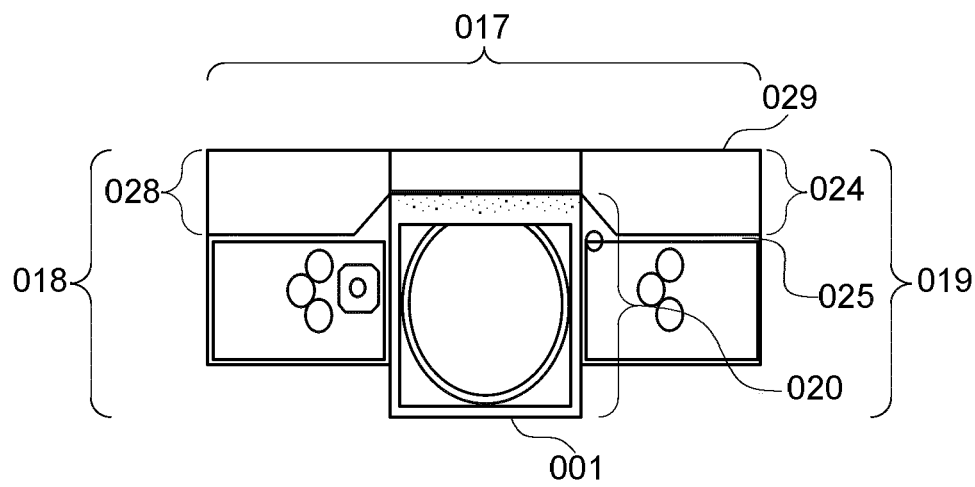

FIG. 3 shows a top view of the system of an embodiment according to the current disclosure, including dimensions of the different elements.

Figure 4A:
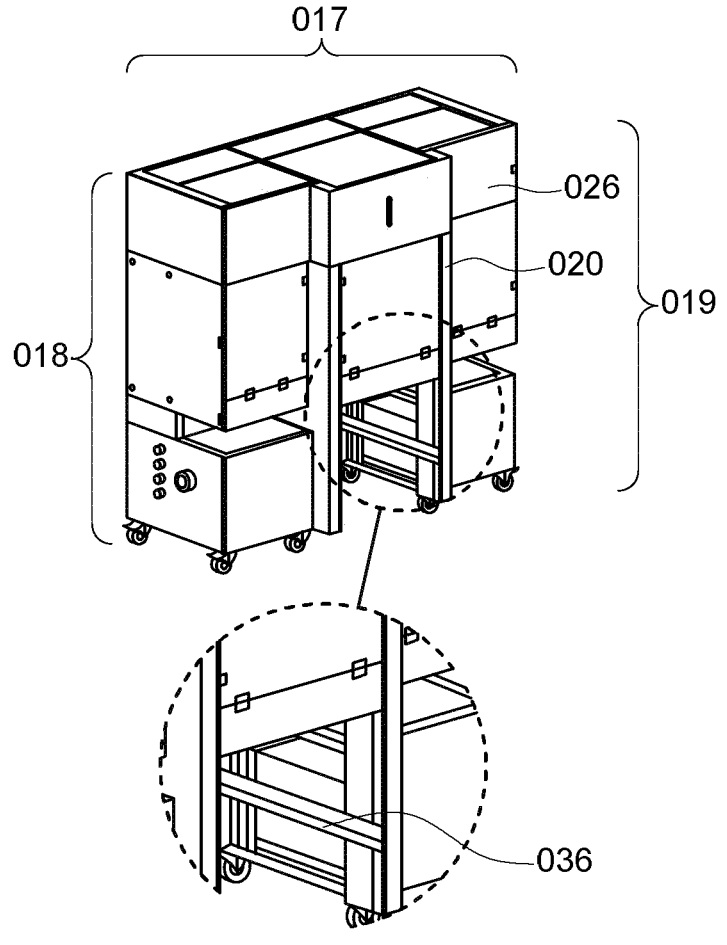

FIG. 4A shows a front view of the system of an embodiment according to the current disclosure, including dimensions of the general casing.

Figure 4B:
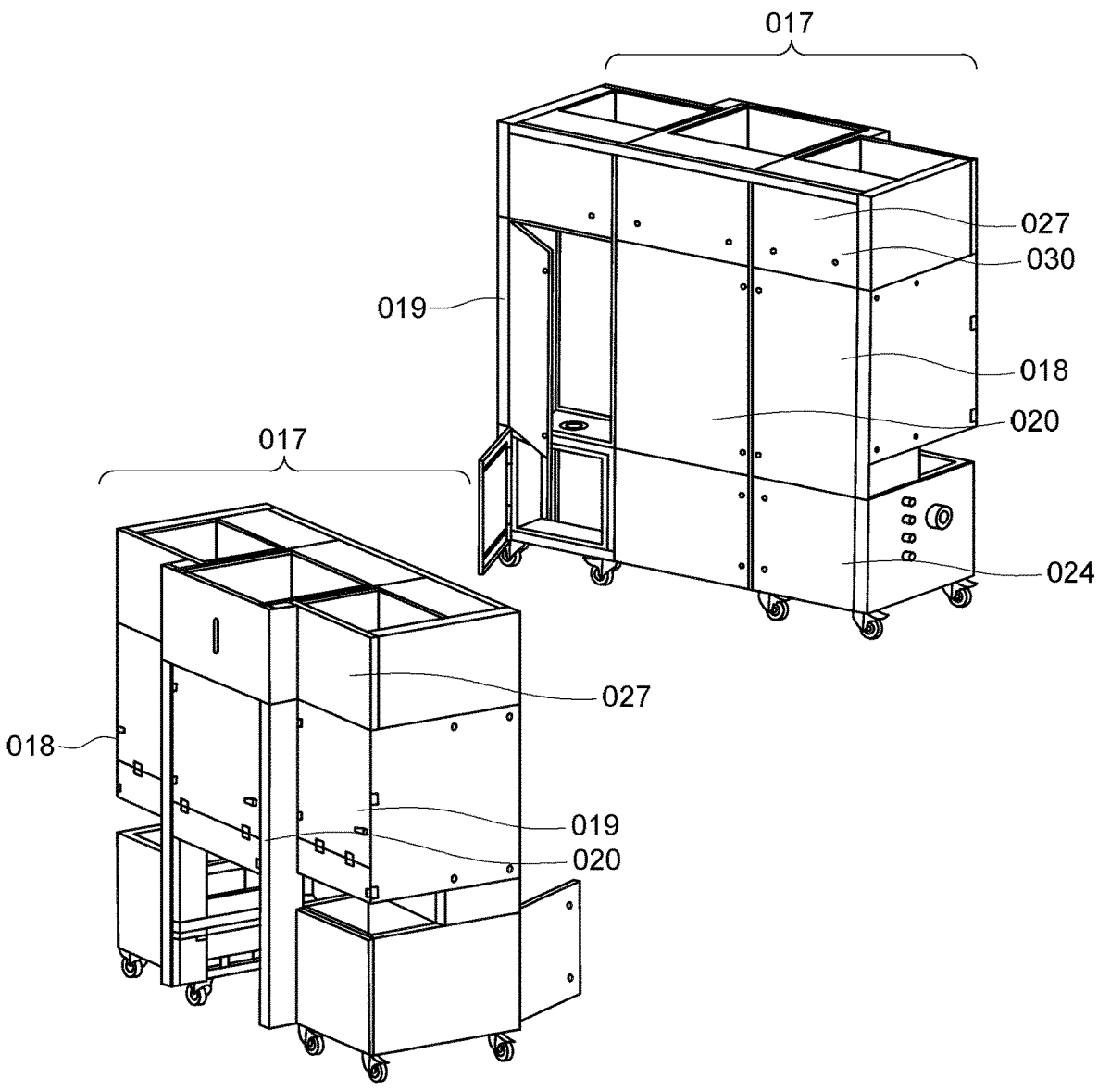

FIG. 4B shows a back view and a front view of the system of an embodiment according to the current disclosure.

Figure 5:
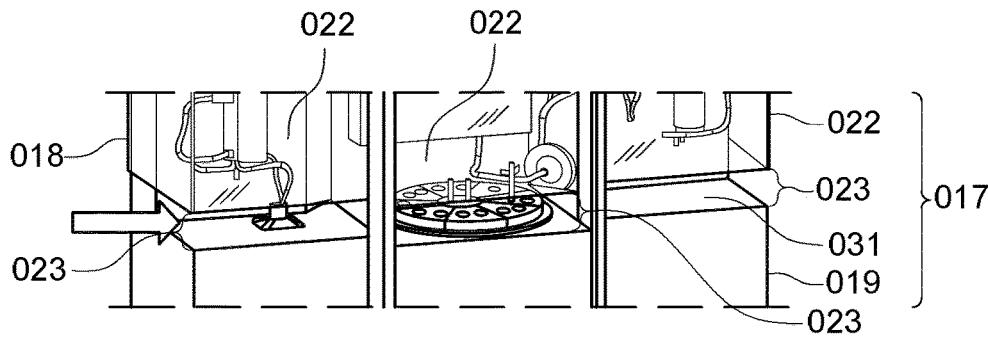

FIG. 5 illustrates a detail of the front view of the system including the front windows of an embodiment according to the current disclosure.

Figure 6A:
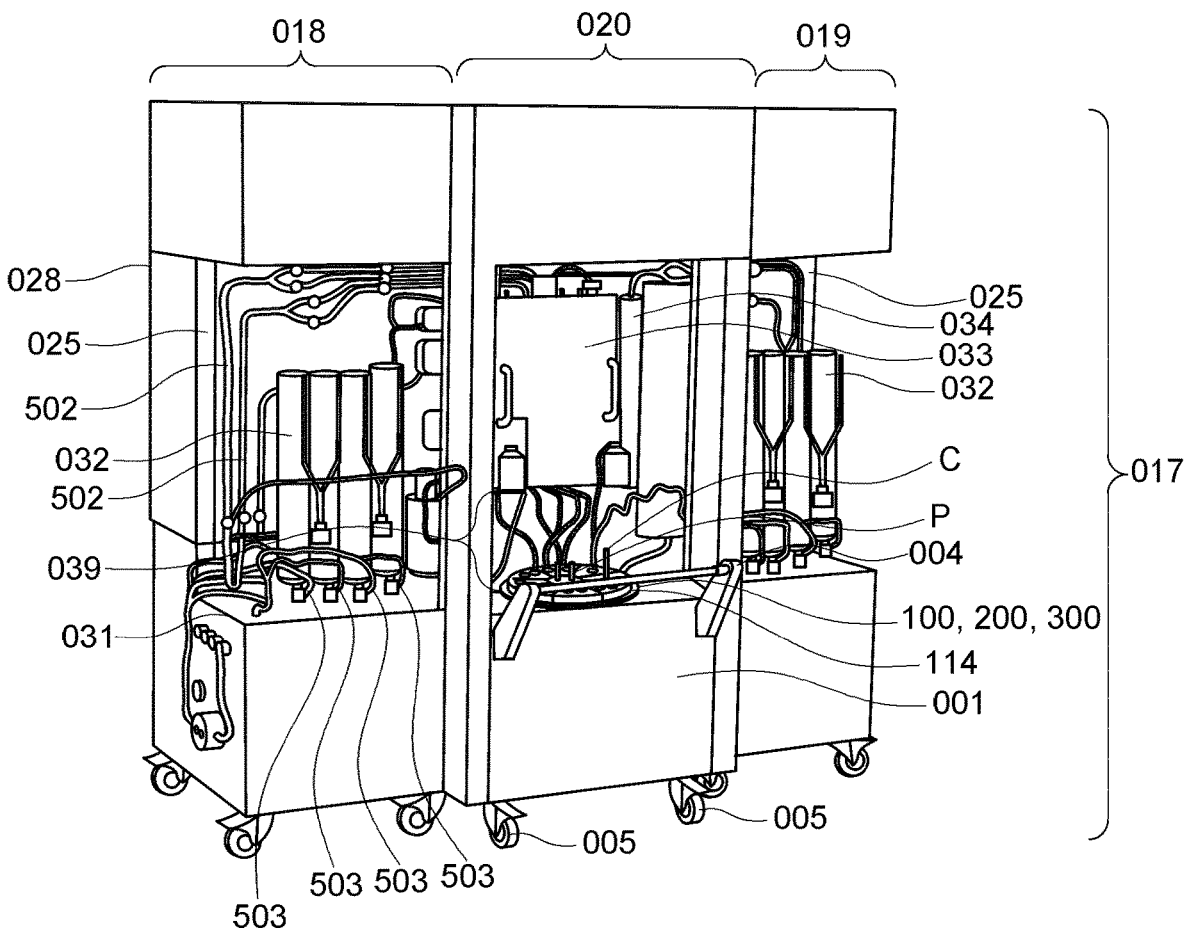
Figure 6B:
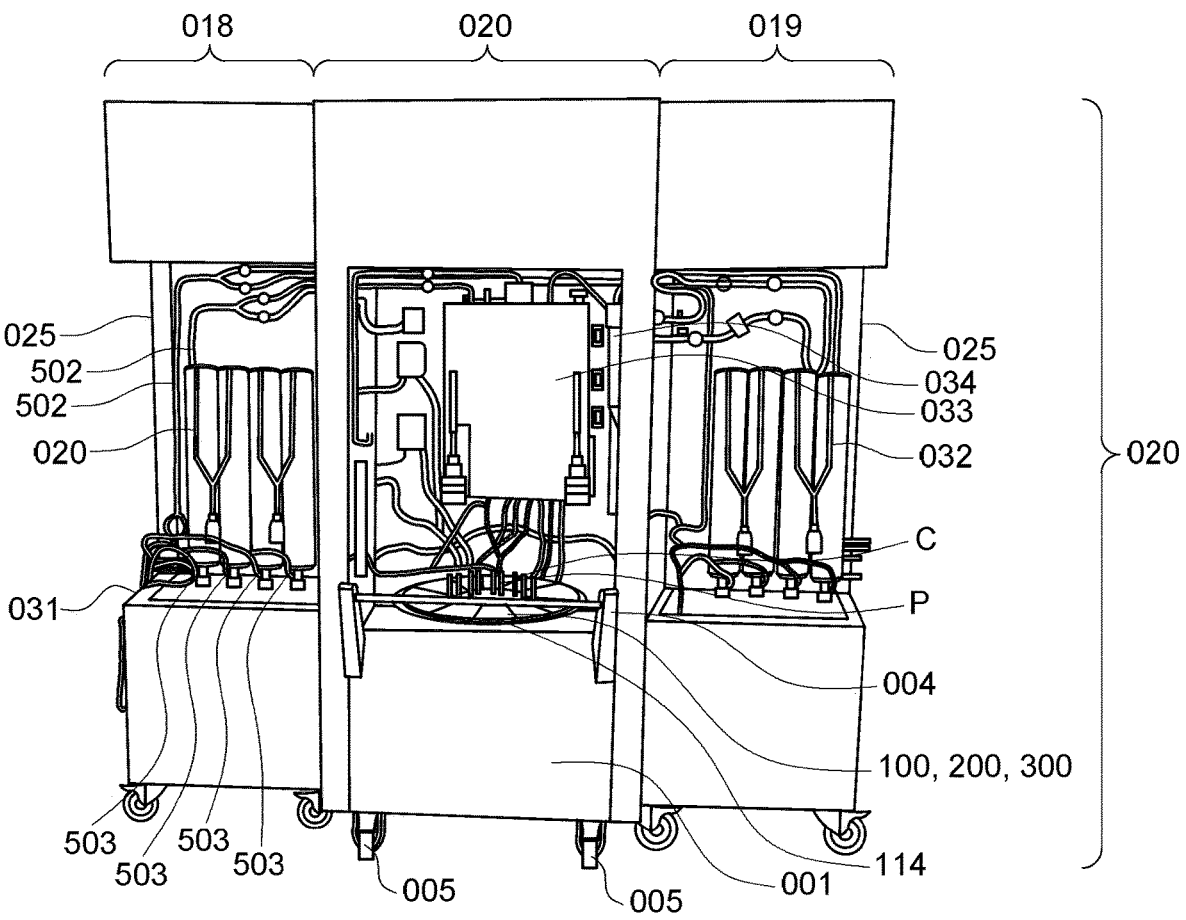

FIGS. 6A and 6B illustrate an embodiment of the system according to the current disclosure, including the collection vessel and TFF.

Figure 7:
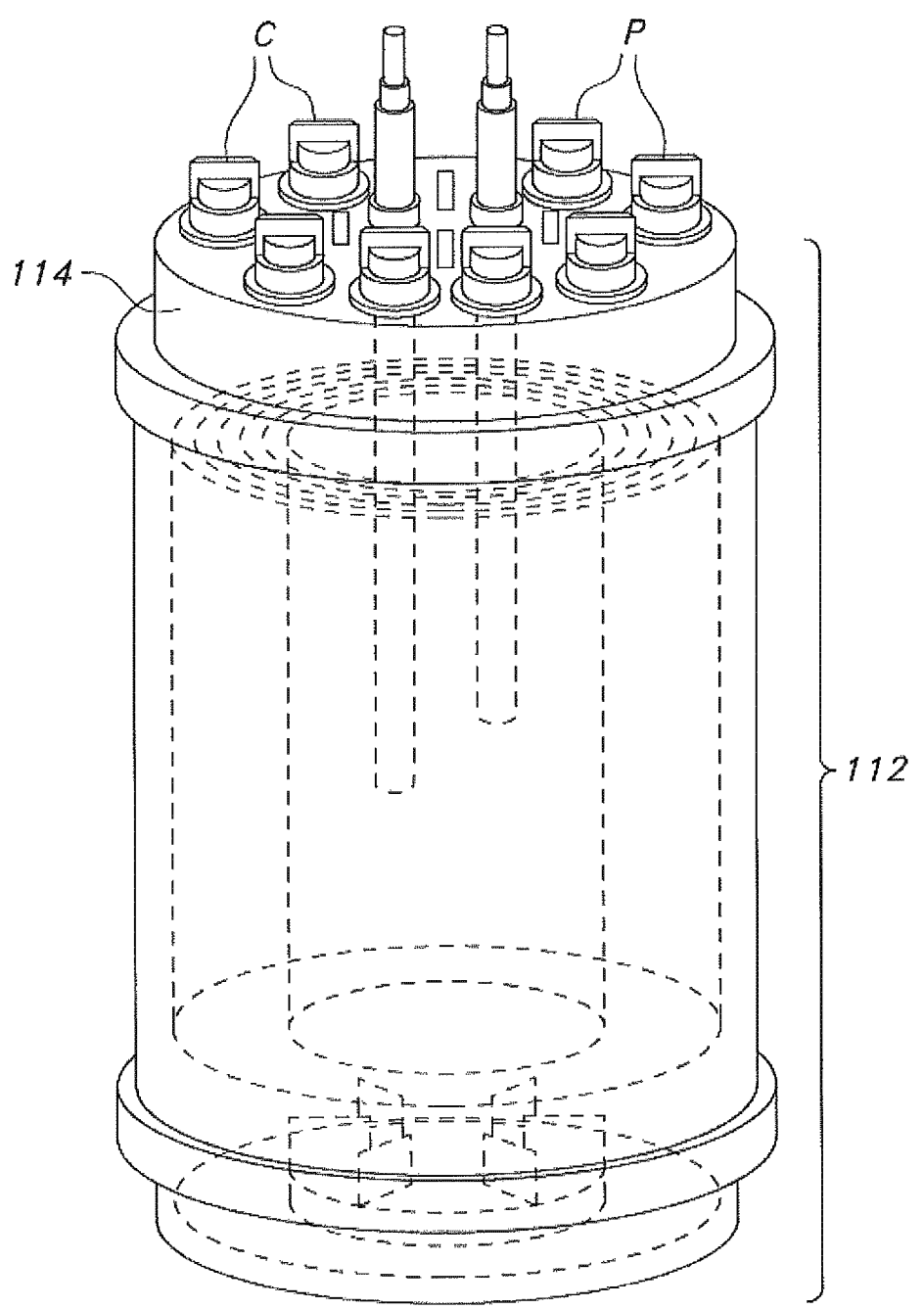

FIG. 7 is a perspective view of a first embodiment of a bioreactor according to the current disclosure.

Figure 8:
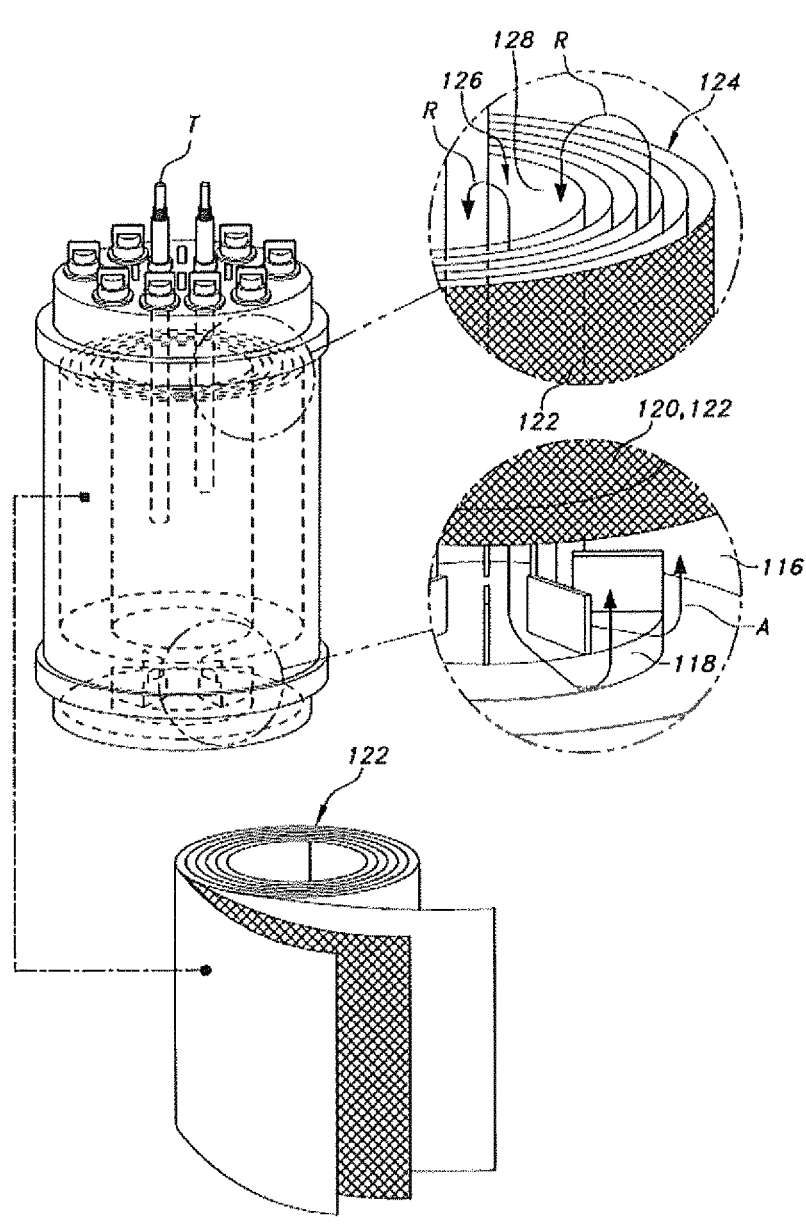

FIG. 8 is a perspective view of a bioreactor of FIG. 7, including several enlarged views.

Figure 9:
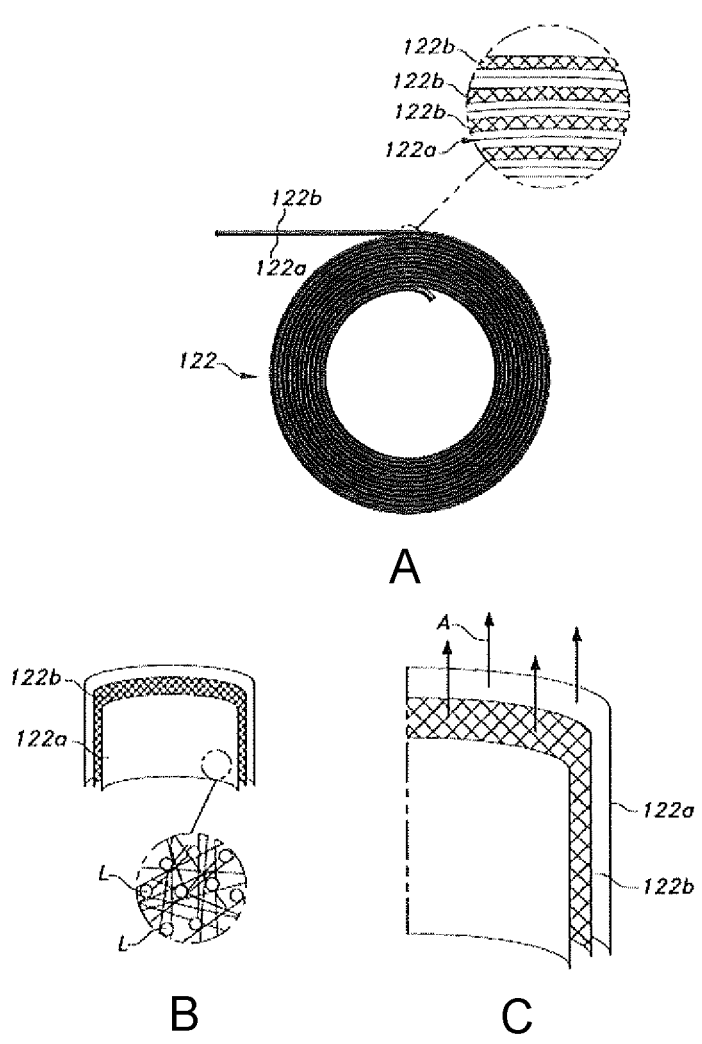

FIGS. 9A, 9B and 9C illustrate a matrix material for use in forming a structured fixed bed for culturing cells in any of the disclosed bioreactors.

Figure 10:
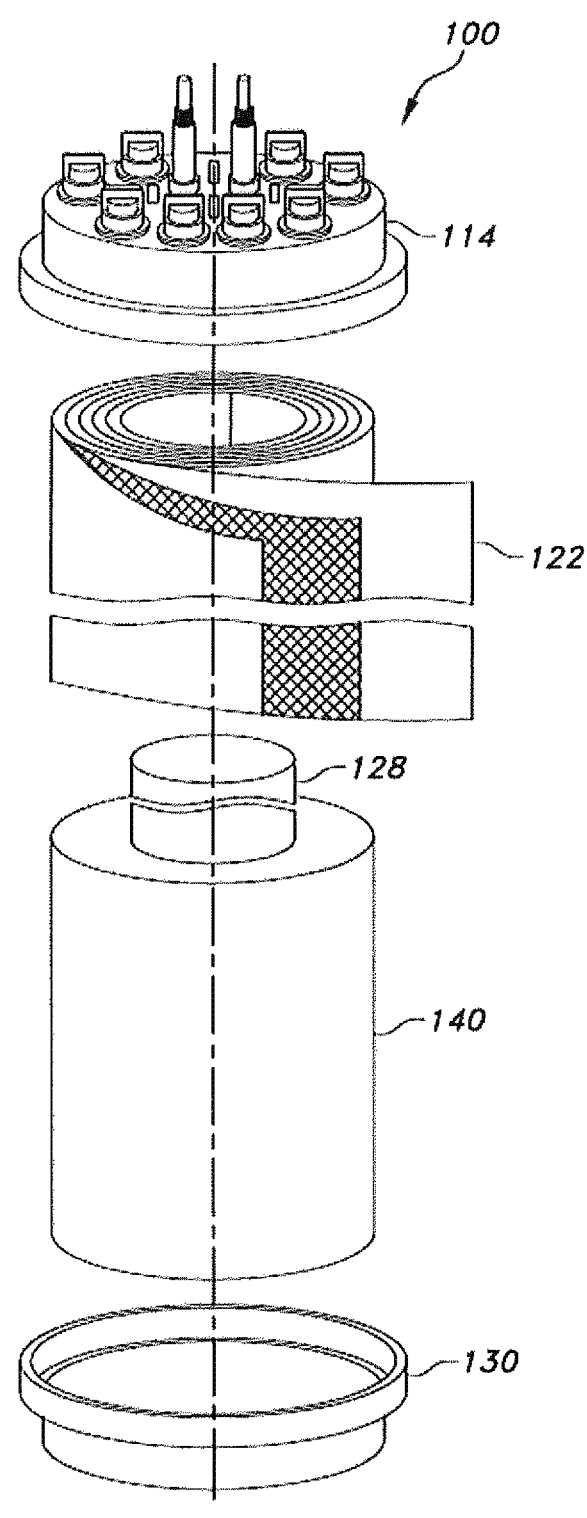

FIG. 10 illustrates a modular version of an embodiment of a bioreactor according to the current disclosure.

Figure 11:
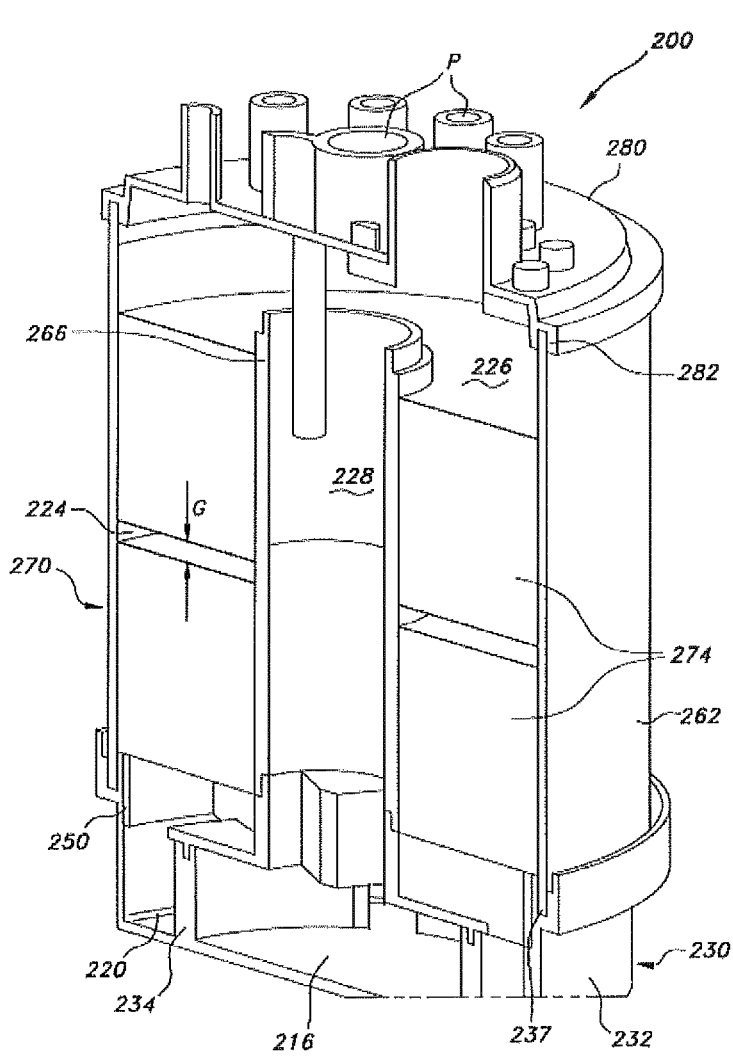

FIG. 11 is a cross-sectional view of an embodiment of a bioreactor according to the current disclosure.

Figure 12:
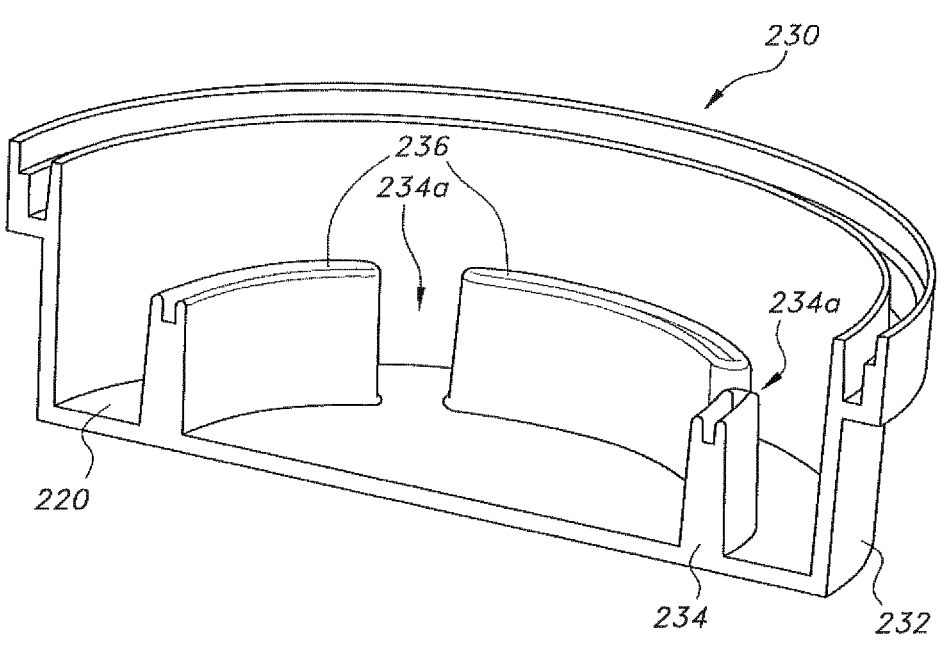

FIG. 12 is a cross-sectional view of a base portion of the bioreactor of FIG. 11.

Figure 13:
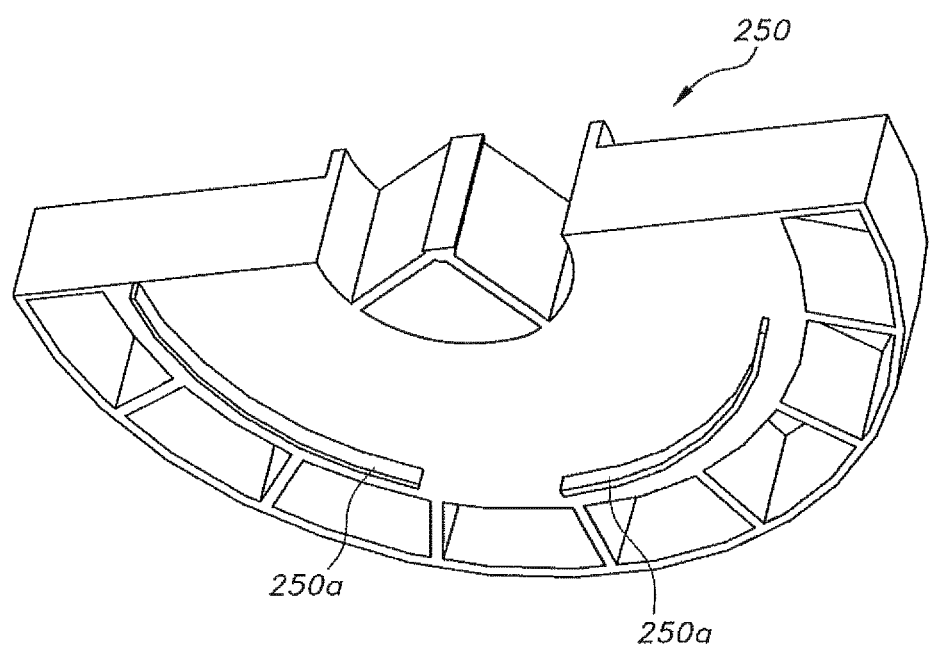

FIG. 13 is a partially cutaway top view of an intermediate part of the bioreactor of FIG. 11.

Figure 14:
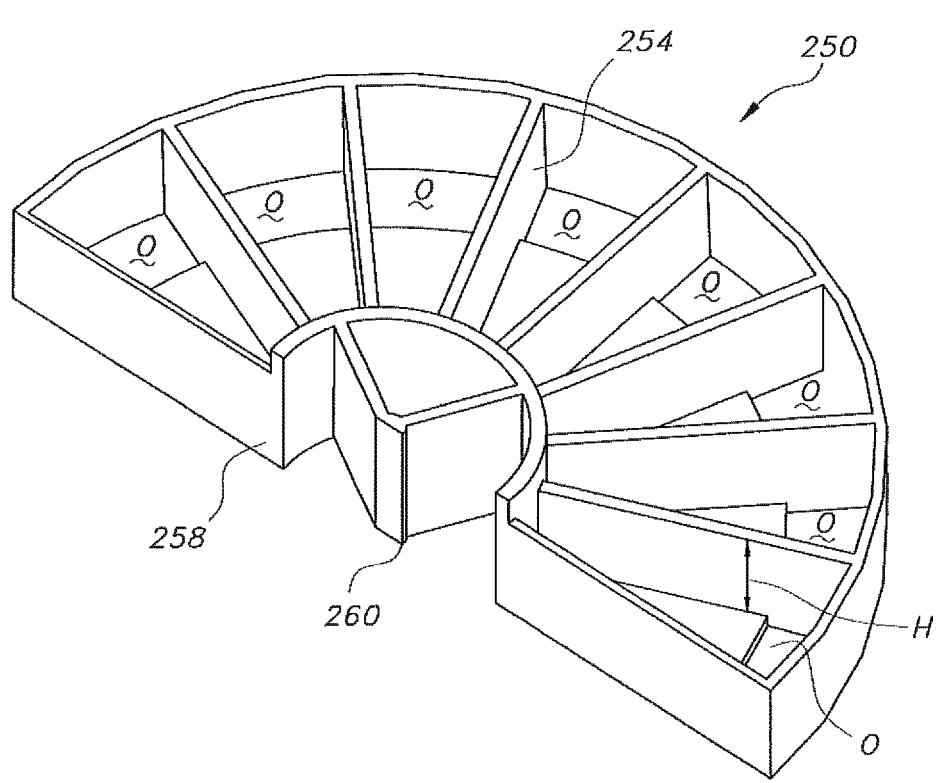

FIG. 14 is a partially cutaway top view of an intermediate part of the bioreactor of FIG. 11.

Figure 15:
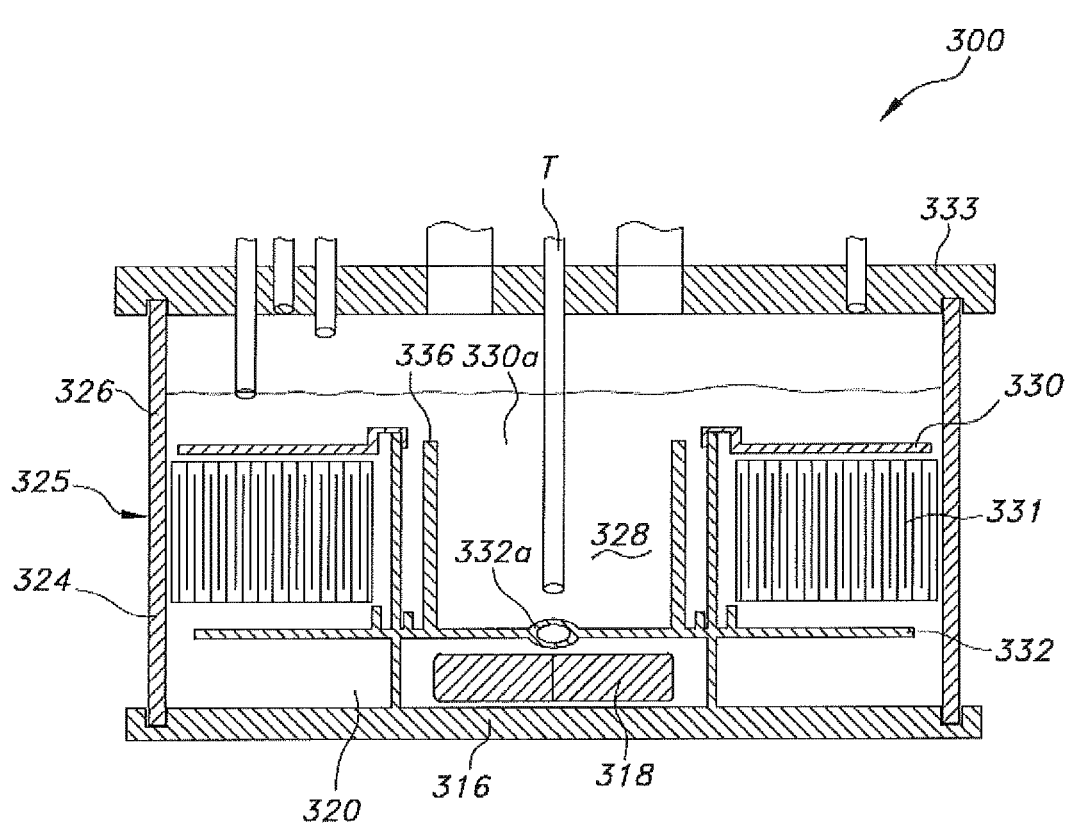
Figure 15A:
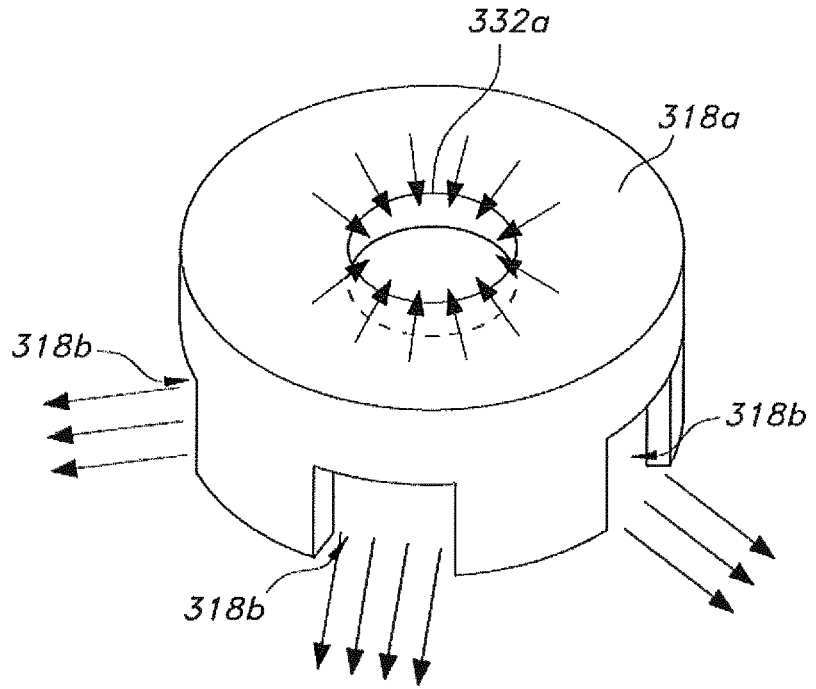
Figure 15B:
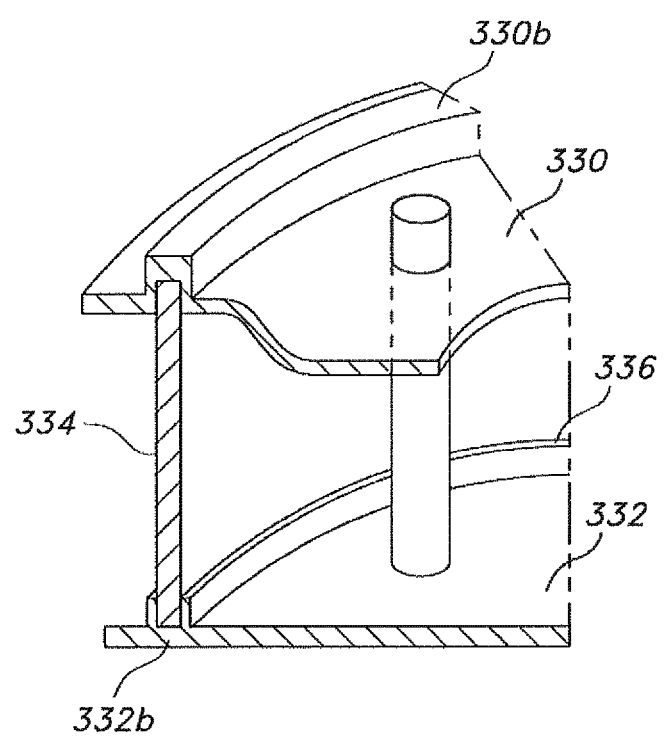

FIGS. 15, 15A and 15B are various view of a third embodiment of a bioreactor according to the disclosure.

Figure 16:
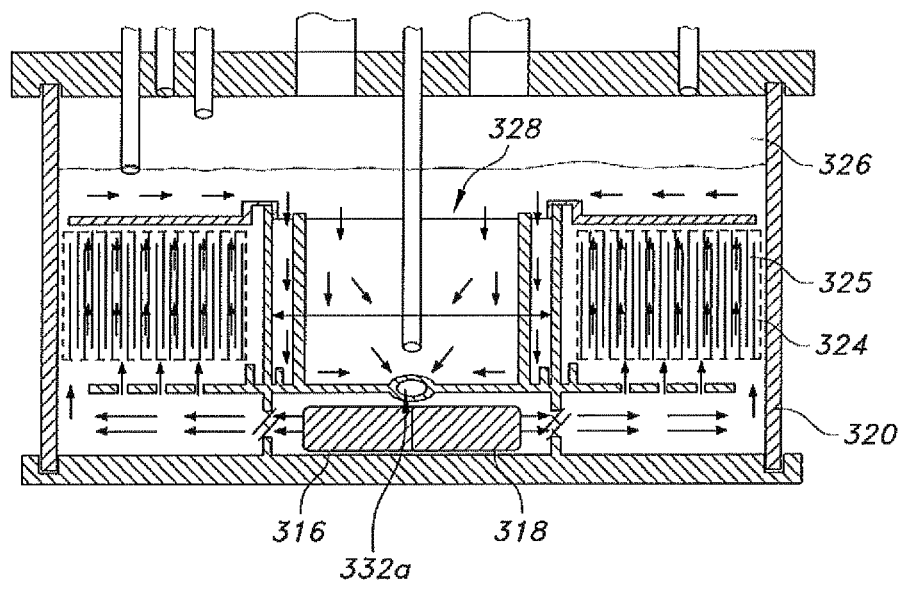

FIG. 16 is a cross-sectional view of the bioreactor of FIG. 15.

Figure 17:
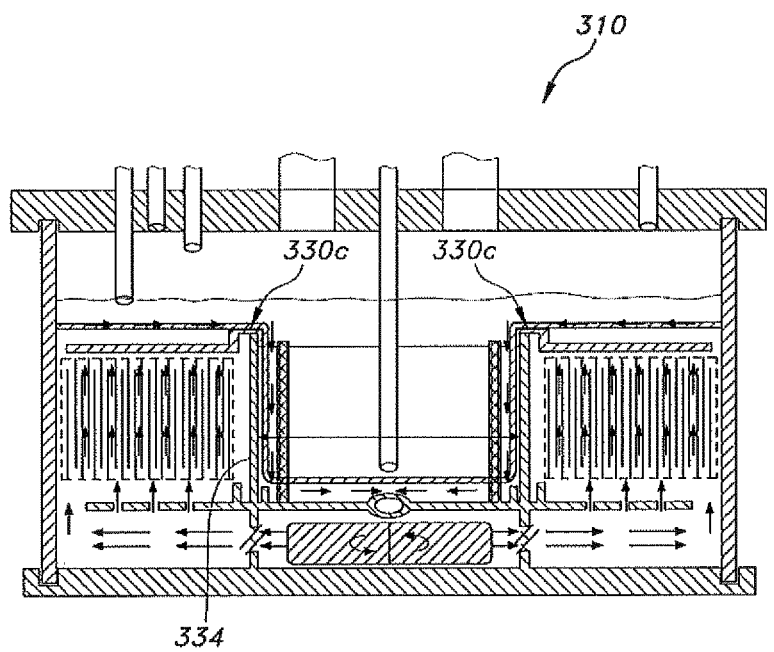

FIG. 17 is cross-sectional view of the bioreactor of FIG. 15.

Figure 18:
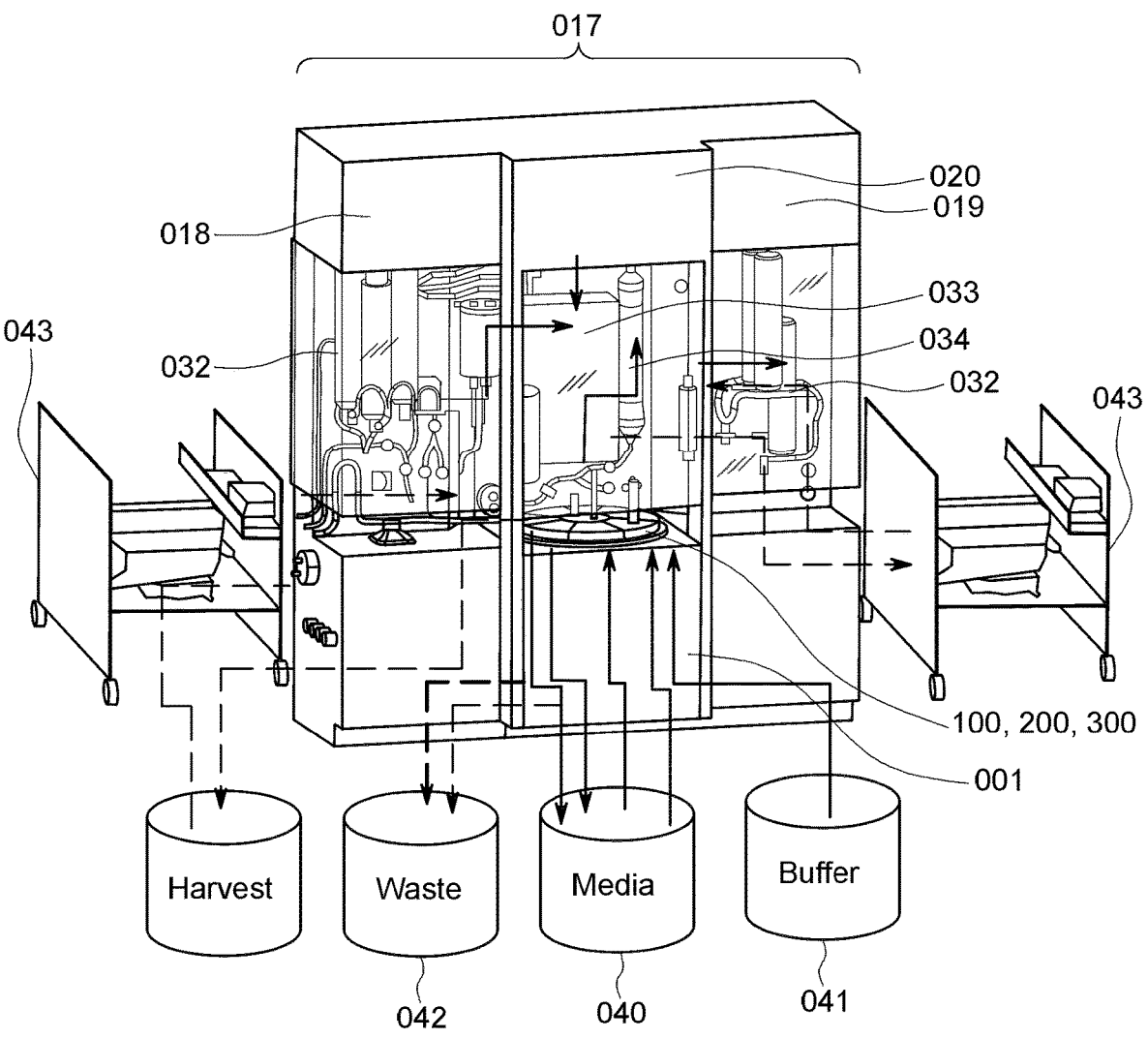

FIG. 18 illustrates a process flow in an embodiment of the system according to the current disclosure.

Figure 19:

FIG. 19 illustrates a possible embodiment of a level sensor according to the current disclosure.

Figure 20:
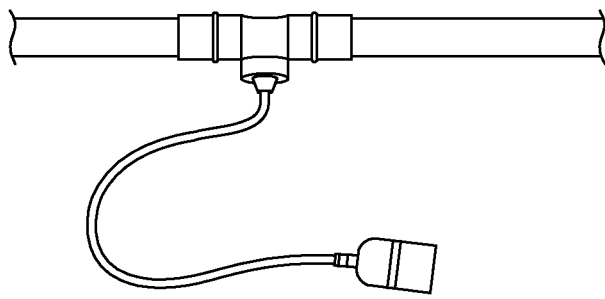

FIG. 20 illustrates a possible embodiment of a pressure sensor according to the current disclosure.

Figure 21:
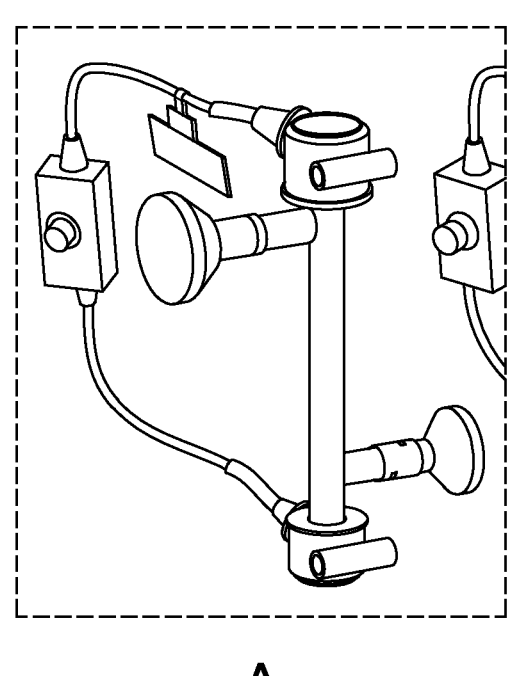
Figure 21:
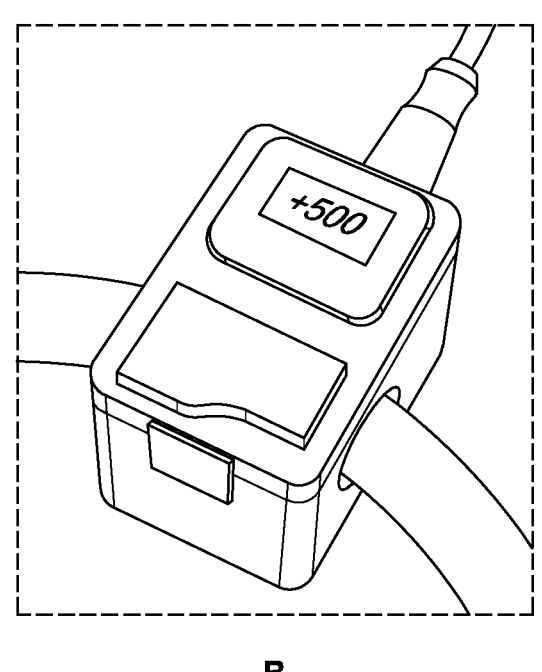

FIG. 21 illustrates two possible embodiments of a flowmeter according to the current disclosure.

Figure 22:
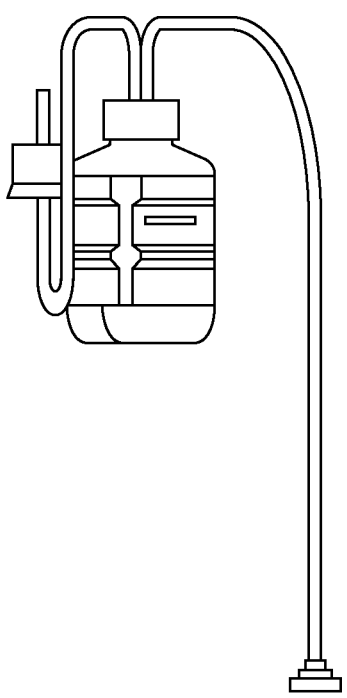

FIG. 22 illustrates a possible embodiment of a bubble or foam trap according to the current disclosure.

Figure 23:
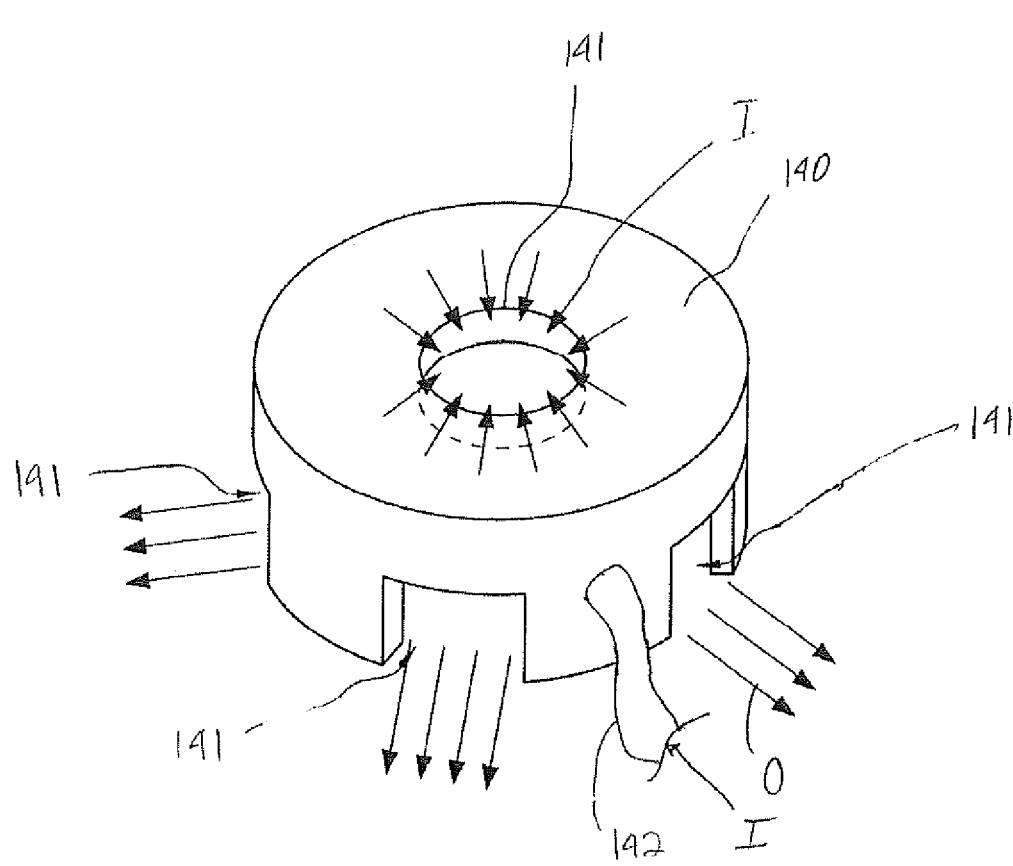

FIG. 23 illustrates a container for a fluid agitator including a gas supply tube according to one aspect of the disclosure.

Figure 24:
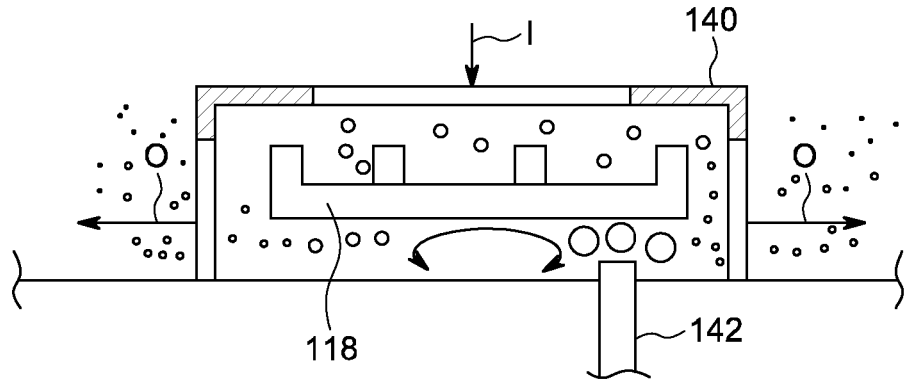

FIG. 24 illustrates an alternative embodiment of the container according to one aspect of the current disclosure.

Figure 25:
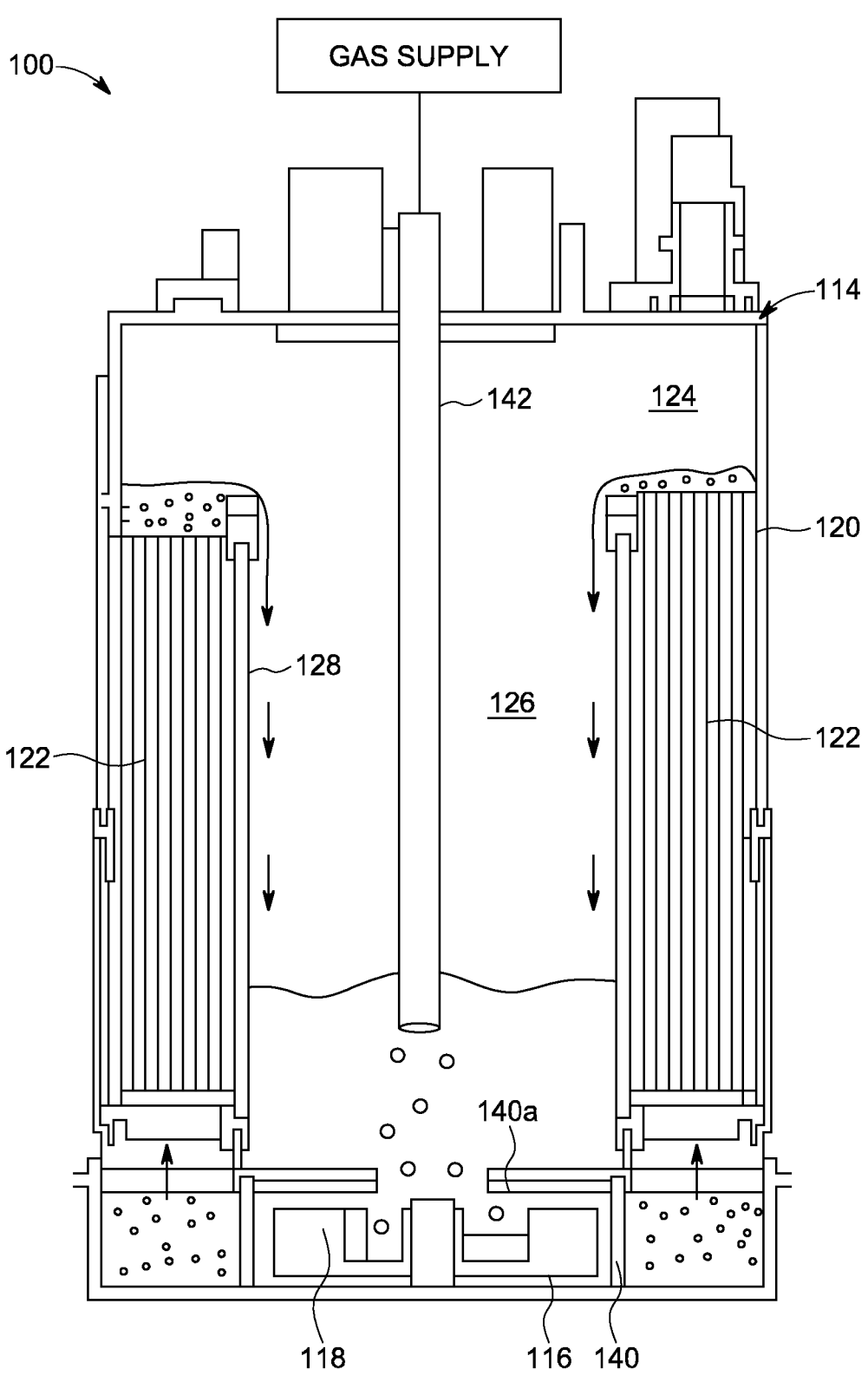

FIG. 25 illustrates a further embodiment of a bioreactor with a gas supply tube according to one aspect of the current disclosure.

Figure 26:
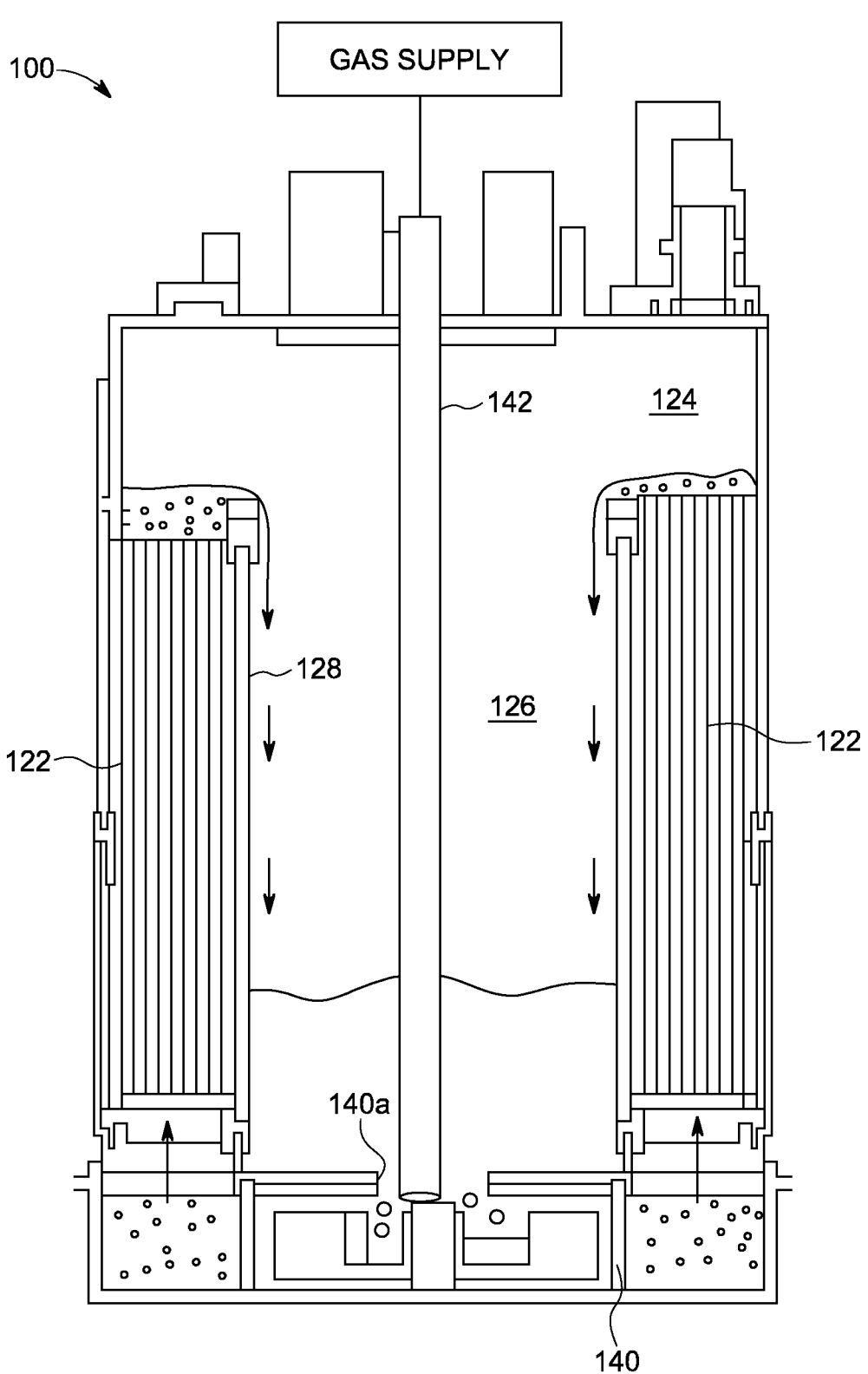
Figure 27:
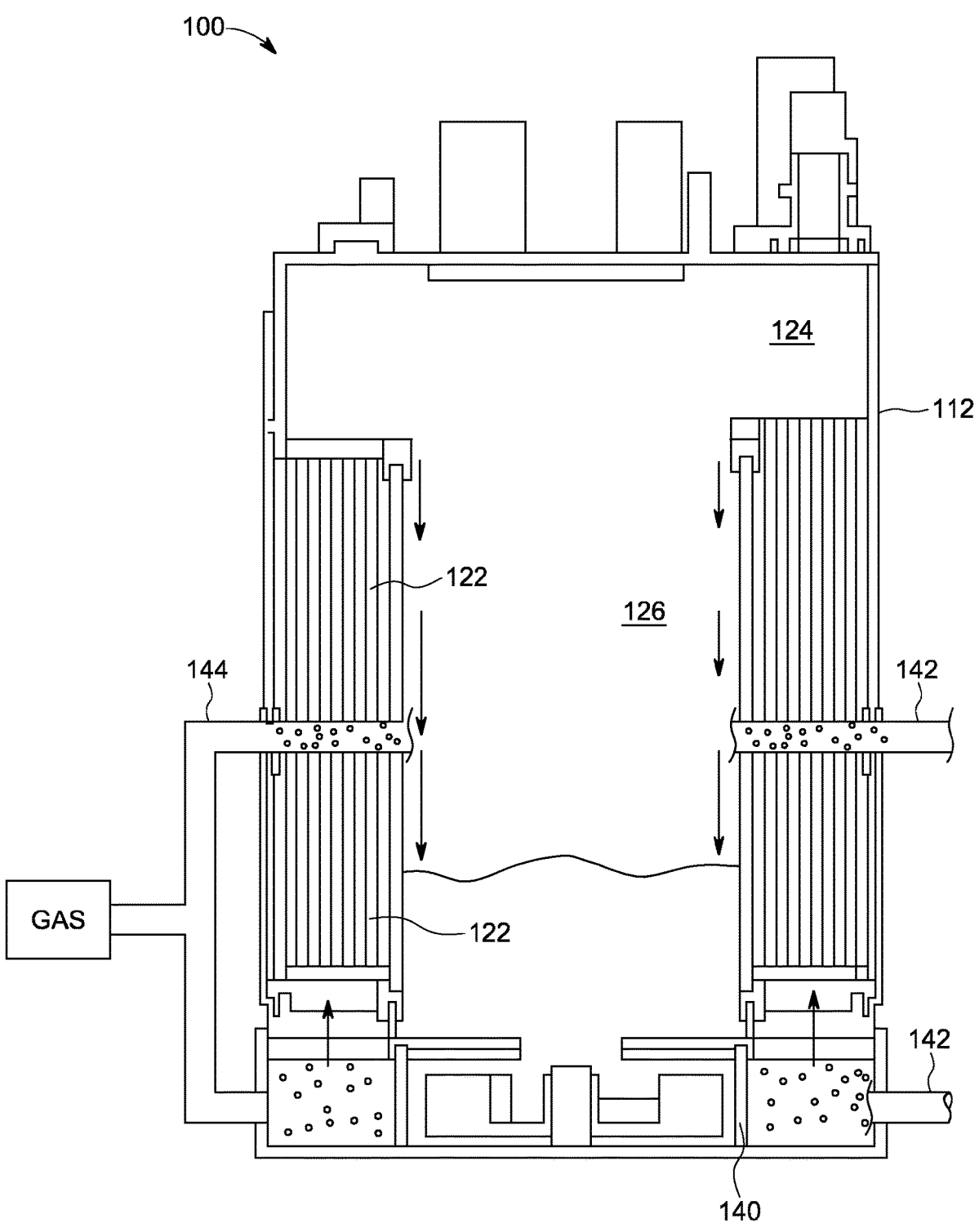

FIGS. 26 and 27 are alternative embodiments of the bioreactor of FIG. 25.

Figure 28:
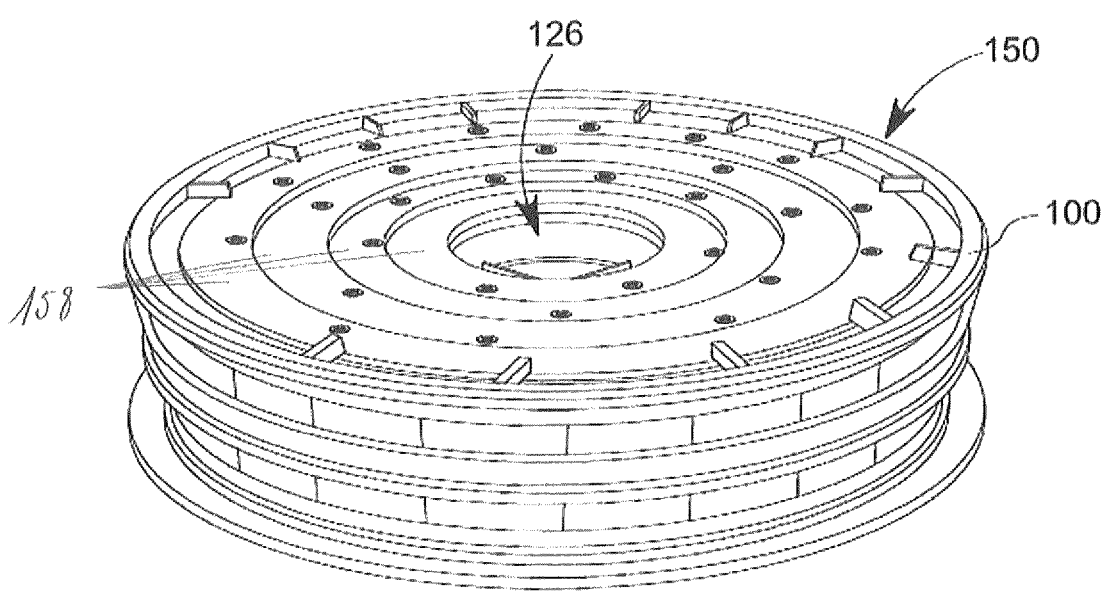
Figure 29:
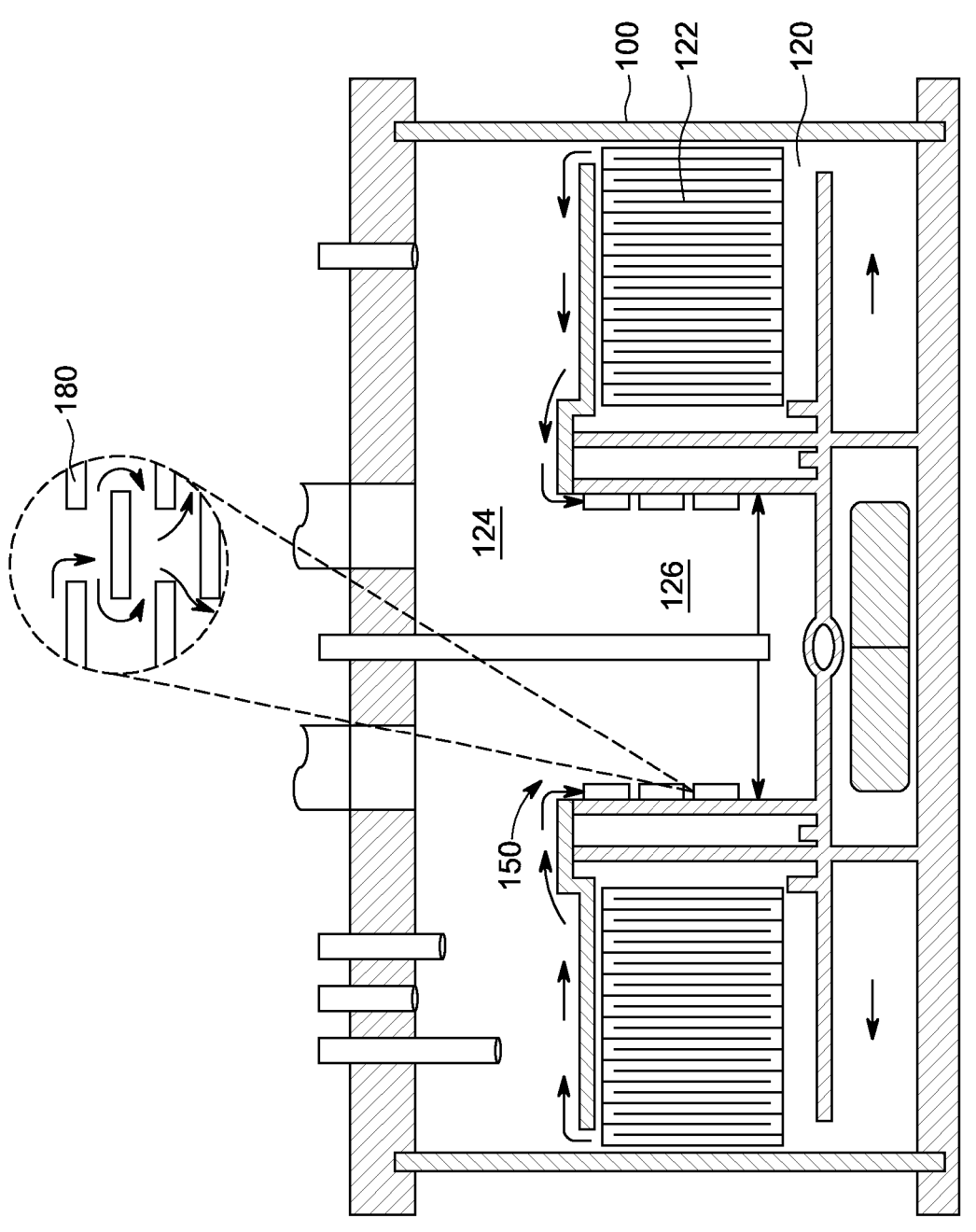
Figure 30:
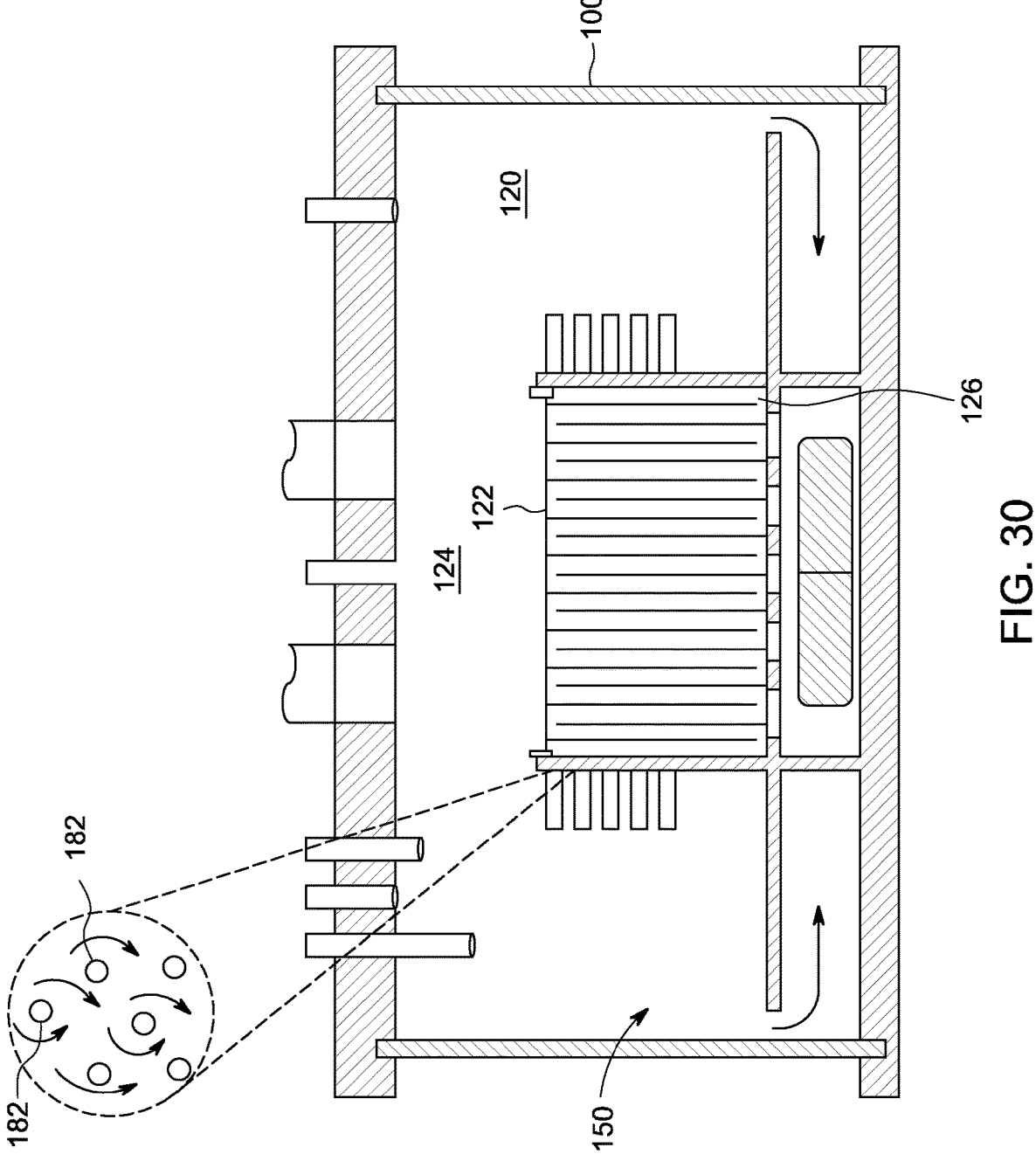

FIGS. 28-30 illustrate embodiments of flow extenders according to one aspect of the current disclosure.

Figure 31:
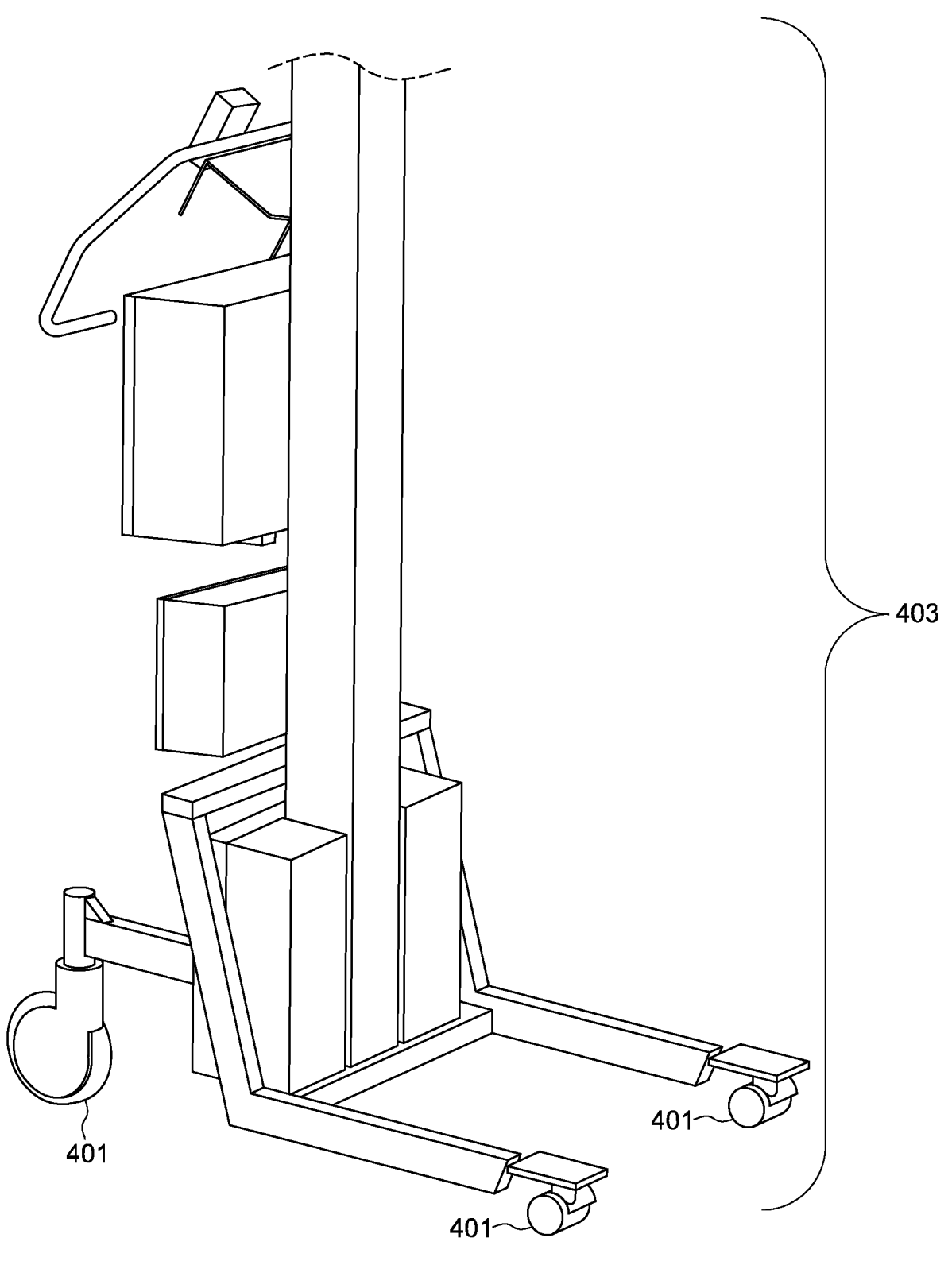

FIG. 31 illustrates an embodiment of a lift for transporting various parts of the system according to one aspect of the current disclosure.

4

Figure 32:
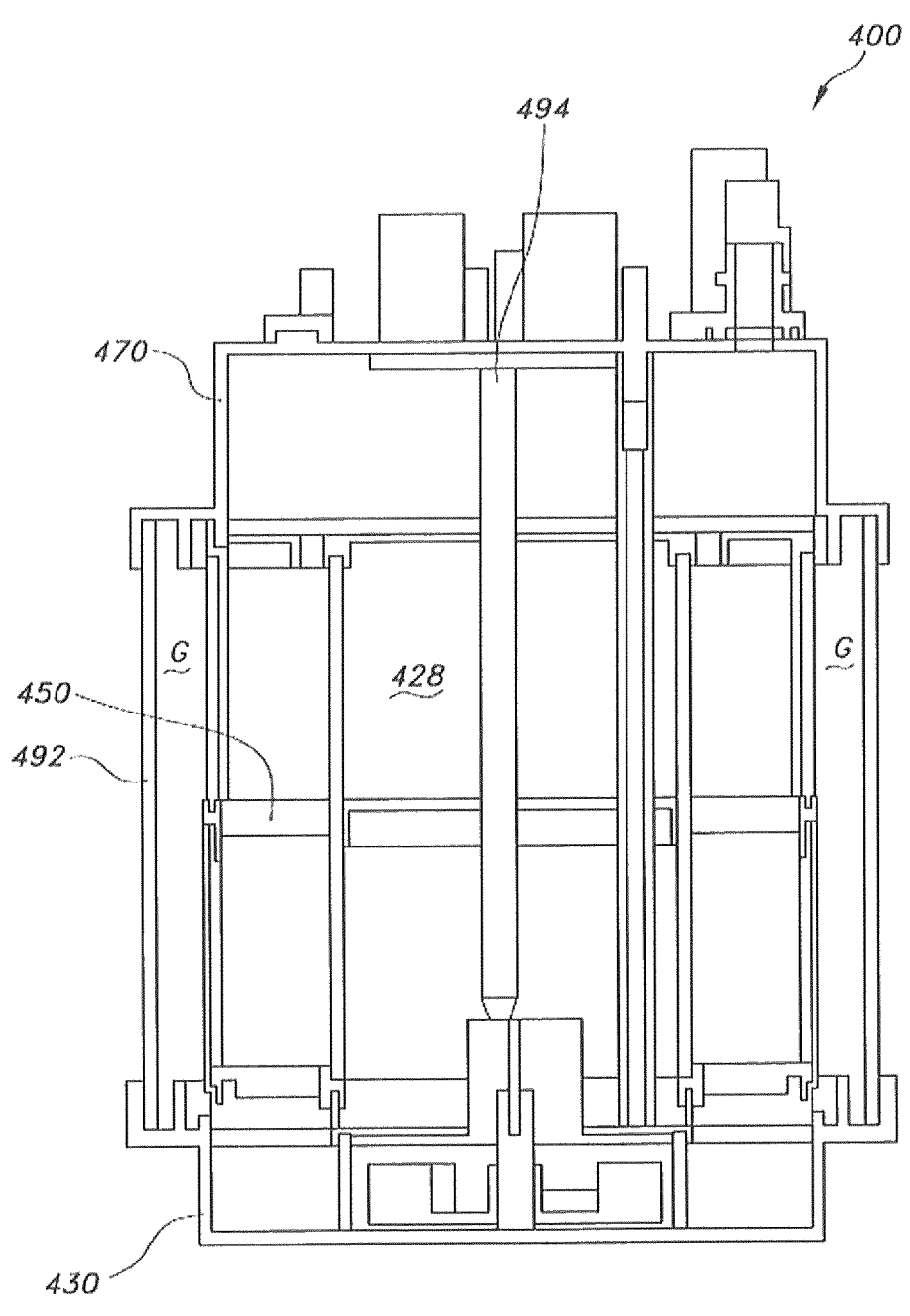
Figure 33:
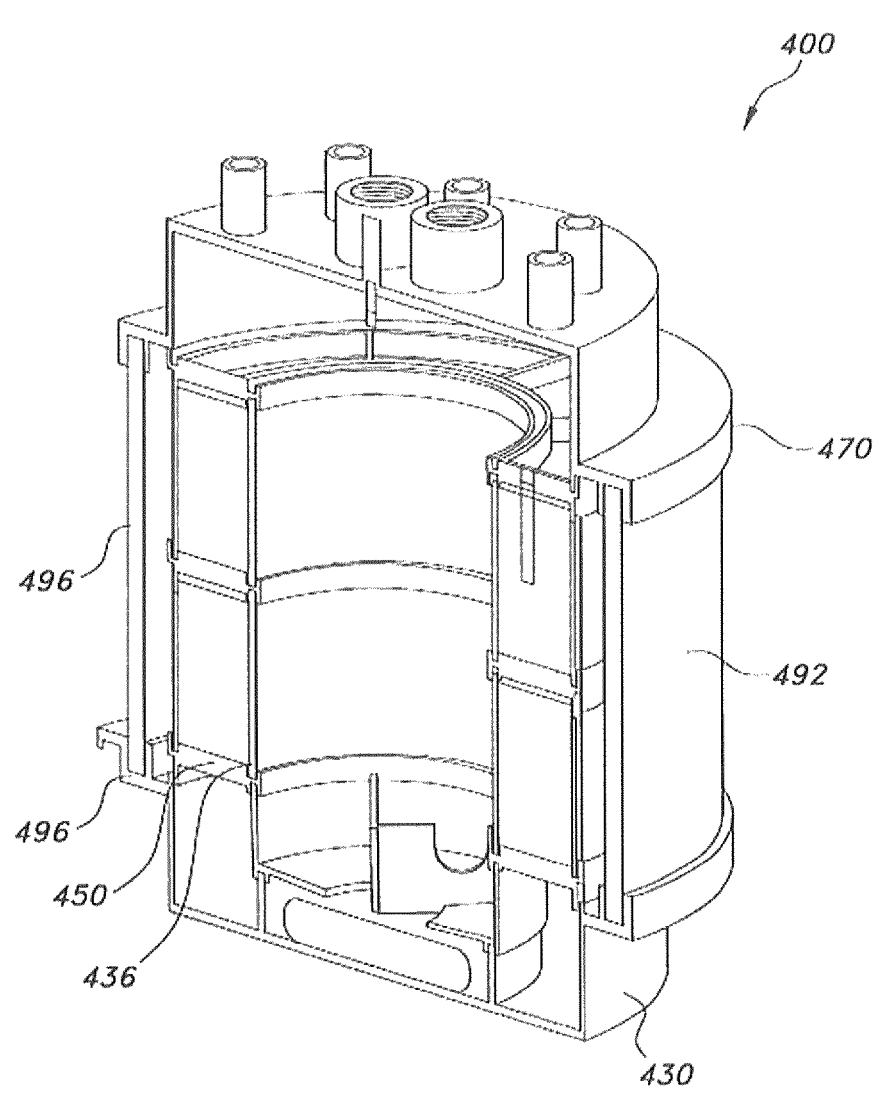

FIGS. 32 and 33 are cross-sectional views of further embodiments of the bioreactor according to the current disclosure.

Figure 34:
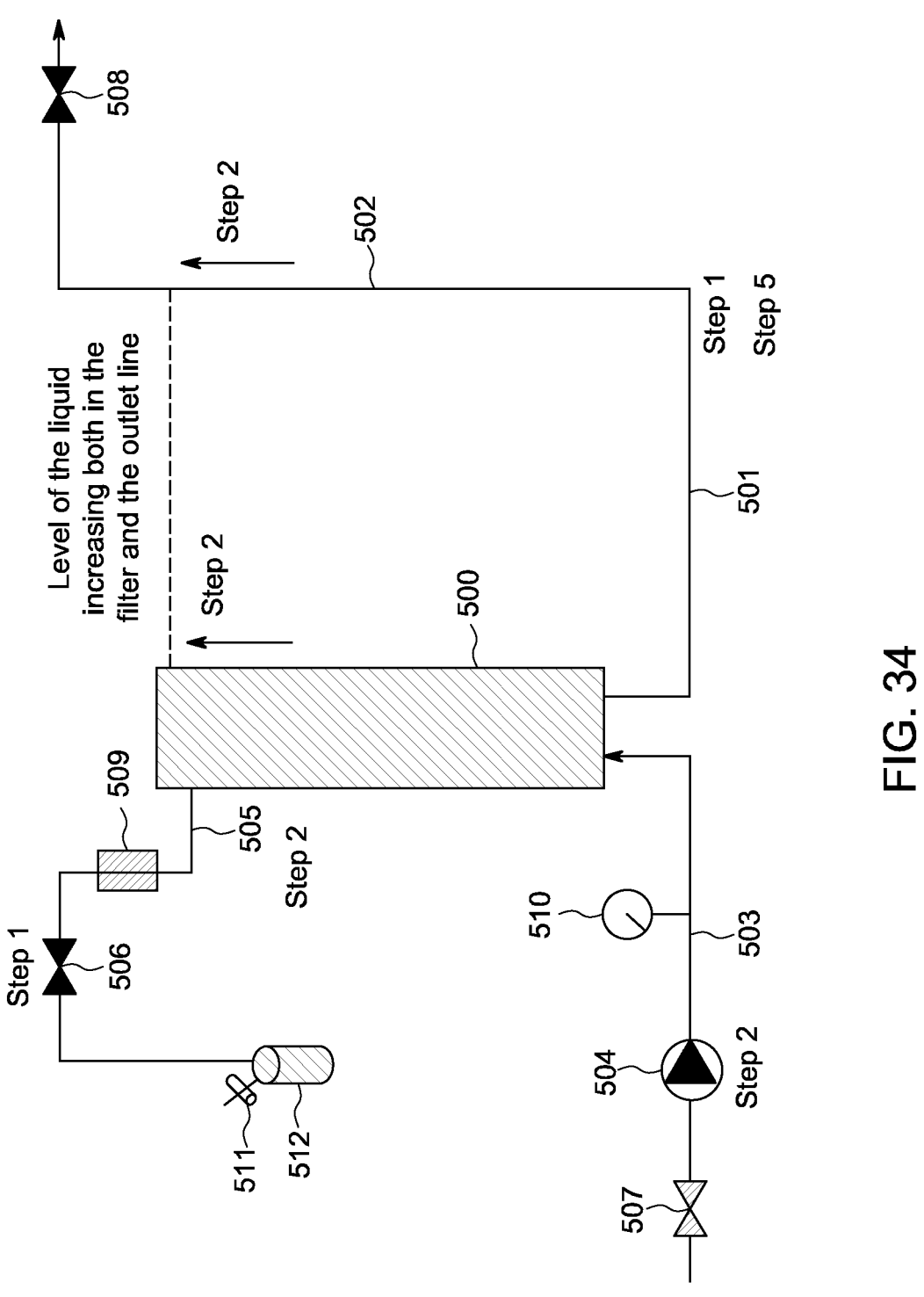

FIG. 34 is a schematic overview of filter unit according to an embodiment of the current invention.

DETAILED DESCRIPTION OF THE
INVENTION

The present invention concerns a device, systems and a method for the production of biomolecules such as proteins, RNA, DNA, viral particles, viral vectors, viral vaccines or antibodies.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

"Biomolecule" refers to any biological material of interest that is produced in a bioreactor. Biomolecules include, for example, viruses, virus-like particles, viral products, gene therapy products, viral vectors, DNA, RNA, proteins such as antibodies, carbohydrates, lipids, nucleic acids, metabolites and peptides.

"Gene therapy product" refers to a therapeutic product comprising nucleic acids to treat or prevent a disease or disorder, such as a genetic disease or disorder.

"Viral gene therapy product" refers to a viral product where a part of the genetic material of the virus is substituted with therapeutic nucleic acids and where the virus is implemented to introduce the therapeutic nucleic acids into the cells of the patient. A number of viruses have been used for human gene therapy, including retroviruses, adenoviruses, herpes simplex, vaccinia, and adeno-associated virus.

"Antibody" refers to any immunoglobulin molecule, antigen-binding immunoglobulin fragment or immunoglobulin fusion protein, monoclonal or polyclonal, derived from human or other animal cell lines, including natural or genetically modified forms such as humanized, human, chimeric, synthetic, recombinant, hybrid, mutated, grafted, and in vitro generated antibodies. Commonly known natural immunoglobulin antibodies include IgA (dimeric), IgG, IgE, IgG and IgM (pentameric).

"Virus" or "virion" refers to an ultramicroscopic (roughly 20 to 300 nm in diameter), infectious agent that replicates only within the cells of living hosts, mainly bacteria, plants, and animals: composed of an RNA or DNA core, a protein coat, and, in more complex types, a surrounding envelope.

"Bioreactor" refers to any device or system that supports a biologically active environment, for example for cultivation of cells or organisms for production of a biological product or biomolecule. This would include cell stacks, roller bottles, shakes, flasks, stirred tank suspension bioreactors, high cell density structured or unstructured fixed-bed bioreactors, batch reactors, etc.

"Purification" refers to the substantial reduction of the concentration of one or more target impurities or contaminants relative to the concentration of a target biomolecule.

"Tangential flow filtration (TFF)" refers to a method of membrane filtration in which fluid is forced through a space bounded by one or more porous membranes, where molecules small enough to pass through the pores are eliminated in the filtrate or "permeate", and molecules large enough to be rejected by the pores remain in the "retentate". The name tangential flow particularly refers to the fact that the direction of fluid flow is roughly parallel to the membrane, as opposed to so-called dead-end filtration where flow is roughly perpendicular to the membrane.

As used herein, "viral infection" refers to the entry of a virus into a cell and the subsequent replication of the virus in the cell.

"Cell culture harvest", "culture harvest" and "harvest" are used as synonyms and refer to the unclarified cell culture obtained from culturing cells in a bioreactor. The cultured cells or the grown cells also are referred to as host cells.

"Serial, in-line" means that devices or units are connected such that the outflow of one unit or device is directly fed into a subsequent unit or device, without intermediate storage.

As used herein, "docking" means to make a stable connection between two elements, whereby the elements can for instance comprise either a receiving portion or a connecting portion. In this disclosure, docking can for instance occur between the bioreactor cabinet and the system for production of biomolecules or between the bioreactor itself and the bioreactor cabinet.

In a first aspect the disclosure concerns a bioreactor cabinet, configured to be incorporated in a biomolecule production system, wherein said bioreactor cabinet is preferably a wheeled (or otherwise mobile) bioreactor cabinet suited to receive a bioreactor, said bioreactor cabinet is provided thereto with a bioreactor docking station, wherein said bioreactor cabinet, preferably a side wall of said bioreactor cabinet, is provided with a connector allowing the transmission of power, signals and/or data when paired with a biomolecule production system, such as a bioreactor chamber of said system.

In an embodiment, the disclosure concerns a bioreactor cabinet, configured to be incorporated in a biomolecule production system, wherein said bioreactor cabinet is preferably a wheeled bioreactor cabinet suited to receive a bioreactor, said bioreactor cabinet is provided thereto with a bioreactor docking station, wherein a wall, preferably a sidewall, of said bioreactor cabinet is provided with a connector allowing the transmission of power, signals and/or data when paired with a bioreactor chamber from a biomolecule production system.

In an embodiment, said bioreactor cabinet is adapted to dock into said bioreactor chamber of said biomolecule production system by means of a connection means, comprising a connector which allows the transmission of power, signals and/or data. In a further embodiment an additional connection is provided which allows to physically secure said bioreactor cabinet to said bioreactor chamber.

In another embodiment the bioreactor cabinet can align with a production system. The advantage of designing a separate bioreactor cabinet that can align with a production system is that it makes an easy installation of the bioreactor possible by one or two operators outside the production system. In addition, when the bioreactor cabinet is removed, this allows a safe access for all manifold connections of the production system.

In an embodiment the bioreactor cabinet is designed to be mobile. To such extent, said bioreactor cabinet may be provided with structures or components that allow the mobility or transportation of said bioreactor cabinet. Transportation means can include any means suitable in the art, both manually and/or electronically controlled, and include but are not limited to wheels, tracks, rolls . . . . Alternatively, or in addition to, in a further embodiment, said bioreactor cabinet may be provided with suitable structures that allow conjunction with an elevator or lifting device that may subsequently transport said bioreactor cabinet. In a preferred embodiment, the bioreactor cabinet comprises wheels.

The bioreactor cabinet might be made of any material suitable in the art such as metal alloy, metal, or plastic. In one embodiment, the bioreactor cabinet is made from a material comprising aluminum or stainless steel. In a specifically preferred embodiment, said bioreactor cabinet is made of a material comprising stainless steel.

In an embodiment of the disclosure the bioreactor cabinet is comprised of one or more handles for easy handling of said cabinet. The handle(s) make(s) it possible for an operator to move the bioreactor cabinet by pushing or pulling on the handle(s). The handle(s) can have various sizes and can be placed at different positions on the outside enclosure of the bioreactor cabinet. In some embodiments, one handle is placed along the total length of a wall of the bioreactor cabinet. In other embodiments, two or more handles are placed on the right and left side of the front wall of the bioreactor cabinet. In another embodiment, the handles are adjustable, removable and/or retractable. Said handle(s) may be made of any material suitable in the art such as plastic, aluminum, steel, metal alloy. In a specifically preferred embodiment, said handle(s) is/are made of stainless steel. Stainless steel has a high corrosion resistance and retains strength at high temperatures.

In a preferred embodiment, the handle is connected to the front wall of said bioreactor cabinet. This position will allow an operator to push and manipulate the bioreactor cabinet with great precision, especially when docking it into the system for the production/purification of biomolecules. In an embodiment, the handle is a metal bar, which is spring loaded and comprises 2 rods on its extremities that can be pulled towards the center of the metal bar. In an embodiment, it is possible to lower the metal bar to a lower position by pulling the 2 rods from the extremities of the metal bar towards the center of the metal bar. By lowering the handle, manipulations (such as sampling and docking the bioreactor cabinet into the system) are facilitated.

In order to allow docking, the bioreactor cabinet is provided with a connector allowing the transmission of power, signals and/or data when paired with a biomolecule production system and, optionally, one or more magnetic or other coupling-type connections (for instance, Radio Frequency (RF) technology) for allowing the connection to said biomolecule production system. As such, both the bioreactor cabinet and the system will be able to communicate with each other and transfer data.

In an embodiment, said connector is able to introduce the coupling of the bioreactor cabinet to a bioreactor chamber of the production system by means of a connecting portion and receiving portion. Said connecting portion may be located at the bioreactor cabinet whereas the receiving portion is present in the bioreactor chamber of said system or vice versa.

In an embodiment, the connector can be a modular connector system allowing combinations of power and signal contacts, Ethernet, optical fiber, coaxial contacts, hydraulic, pneumatic and thermocouplings in a compact frame or housing. This modular connector system can be configured according to the specific requirements of the connection. In a preferred embodiment the connectors are waterproof. In an embodiment, the male connector of the bioreactor cabinet is connected to the female connector of the production system. To ensure correct connection between the male and female connector, the female connector may contain centering pins. In another embodiment, the connector comprises an electronic eye to ensure correct connection. In another embodiment, the connector comprises magnetic elements to ensure correct connection.

In a further or in another embodiment, a connecting portion on the bioreactor cabinet and a receiving portion on the system will allow docking of the bioreactor cabinet to the system to ensure that both entities are firmly connected to each other, prohibiting the release of the bioreactor cabinet from the system during the production of biomolecules. This connecting and receiving portion can be any known connecting system suitable in the art, such as of mechanical or magnetic system. A break-away function can be incorporated to be able to release the bioreactor cabinet from the system.

In an embodiment, said bioreactor cabinet is comprised of both a connector allowing the transmission of power, signals and/or data when paired with a biomolecule production system and a magnetic connection that allows docking of the bioreactor cabinet to the biomolecule production system. In an embodiment, said magnetic connection may be a permanent magnet. In another, more preferred embodiment, said magnet may be an electromagnet, wherein a magnetic field is produced by an electric current. The main advantage of an electromagnet over a permanent magnet is that the magnetic field can be quickly changed by controlling the amount of electric current. In the current application, the use of a magnet, more specifically an electromagnet enhances the safety of the system, as it will prevent unauthorized docking or removal of the bioreactor cabinet to or from the production system. Said system may be comprised of a corresponding magnetic part to allow interaction with the magnet of said bioreactor cabinet. In an embodiment, the powered part of the magnetic connection is provided on the system and the stainless steel part of the magnetic connection is provided on the back of the bioreactor cabinet. In an embodiment the 2 parts become blocked once power is added. In an embodiment, the 2 parts are blocked with a force of 1000N.

In an embodiment, said connector and one or more magnetic connections of said bioreactor cabinet are provided on different walls. In a preferred embodiment, said connector and magnetic connection are provided on the same wall of said bioreactor cabinet. This again allows easy docking.

In some embodiments, the connector and the one or more magnetic connections are provided on a wall of the bioreactor cabinet, opposite to the front wall. When the bioreactor cabinet is pushed forward with the handle on the front wall of the bioreactor cabinet, the connector and magnetic connection can be aligned easily with their oppositely arranged counterparts present on said production system.

In a preferred embodiment, the bioreactor docking station resides inside the bioreactor cabinet, preferably guarded from the outside environment by the walls of said bioreactor cabinet. Consequently, the bioreactor cabinet does not only provide a means for transporting the bioreactor, but also provides a protective shield to safeguard the bioreactor from harmful encounters, such as collisions with other objects during transportation.

In some embodiments, the docking station of the bioreactor cabinet comprises a removable height adjuster, for allowing positioning of said bioreactor in said docking station.

Such removable height adjuster functions as a support to install the bioreactor. The removable height adjuster may be releasably attached to said bioreactor cabinet and/or docking station and may vary in dimension, depending on the size and the dimension of the bioreactor. In an embodiment, the removable height adjuster will allow positioning of the bioreactor, regardless of its dimension, such that for example the top of the bioreactor is perfectly aligned with the top surface of said bioreactor cabinet. For example, said bioreactor cabinet may be designed to fit a bioreactor of a specific size, such as a bioreactor with 600 $m^2$ internal growth surface. In case the same bioreactor cabinet is to be used with a smaller bioreactor, e.g. a bioreactor of 200 $m^2$ internal growth surface, a height adjuster may be used to accommodate said smaller bioreactor. The latter allows ergonomic manipulation of said bioreactor and its outlets that are located on said surface. Said height adjuster may have any form suitable to be used, such as square, rectangular, round. In an embodiment, said height adjuster is a cylinder or disc-like element. The surface of the height adjuster can't allow deformation of the adjuster. The height adjuster may comprise any material suitable in the art such as plastic, aluminium, steel, metal alloy. Stainless steel has a high corrosion resistance and retains strength at high temperatures.

In an embodiment, said bioreactor cabinet comprises a bioreactor support plate on the top surface of said bioreactor cabinet, that is comprised of a recess to allow the protrusion of a bioreactor. Said recess enhances the ergonomics of said bioreactor cabinet and system. In some embodiments, this bioreactor support plate is a grid-like plate.

These openings in the support plate allow air flow circulation in the bioreactor cabinet. In addition, the openings make it possible to have a better view of the bioreactor inside the enclosure of the bioreactor cabinet. In an embodiment the plate can comprise more than one piece. In a preferred embodiment the plate comprises two pieces. The plate might be made of any material suitable in the art that is resistant to corrosion.

In a preferred embodiment, the bioreactor cabinet comprises a bioreactor provided in a bioreactor docking station.

The bioreactor cabinet is designed to accommodate the bioreactor together with its heating support and an agitation motor. In this way the bioreactor cabinet allows an easy and fast installation or removal of the 3 elements simultaneously (bioreactor-heating support-agitation motor), which can be done by one operator. In addition, a retention tray will be installed in the bioreactor cabinet and connected with a main retention tray of the bioreactor chamber. The retention tray can be equipped with leak detectors. The retention tray will collect potential process leakages. In an embodiment the bioreactor cabinet can contain more than one retention tray. In an embodiment, the different retention trays on the bioreactor cabinet are on different levels and may be connected to each other with a tube. In an embodiment, the maximum capacity of one or more of the retention trays is 85 L.

In some embodiments, the one or more walls of the bioreactor cabinet may be provided with positioning means for allowing the alignment of said bioreactor cabinet with a biomolecule production system and further enhancing docking of said bioreactor cabinet in said system. In a preferred embodiment, the sidewalls of the bioreactor cabinet may be provided with positioning means for allowing the alignment of said bioreactor cabinet with a biomolecule production system and further enhancing docking of said bioreactor cabinet in said system.

Said positioning means help to guide the bioreactor cabinet to align correctly with a biomolecule production system.

Said positioning means may be any kind of element that helps guiding and docking said bioreactor cabinet in said system. In an embodiment, said positioning means are circular or cylindrical elements on a rotating axle such as wheels or gears that are incorporated in sockets in the side walls of said bioreactor cabinet.

In a further embodiment, said positioning means are a pair of wheels, each wheel being on a rotating axle, wherein each pair comprises two wheels, wherein the rotation axle of the first wheel is positioned perpendicular to the rotation axle direction of a second wheel.

In a further embodiment, each side wall of said bioreactor cabinet is comprised of two pairs of wheels, for instance installed at opposite sides of said wall, each along or near the corners of said side walls. Wheels at both sides of the side walls will allow the front and the back of the bioreactor cabinet to be guided correctly into the bioreactor chamber.

In an embodiment the bioreactor chamber further comprises one or more receiving elements to receive the bioreactor cabinet in the bioreactor chamber. In an embodiment the bioreactor chamber further comprises guides to guide the bioreactor cabinet into the bioreactor chamber.

In an embodiment, the bioreactor cabinet comprises an inclinometer to ensure the bioreactor is on a horizontal surface. In a further embodiment, the inclinometer is set on the bioreactor cabinet to ensure the bioreactor is on a horizontal surface. In a still further embodiment, a maximum deviation angle of horizontality limit is set to activate an alert that indicates the bioreactor cabinet is not perfectly horizontally positioned. In an embodiment, a degree of inclination is determined by a wear-free semiconducting sensor element.

Typical bioreactors are constructed with fixed dimensions (height, in particular), and thus can be difficult and costly to transport to remote locations where cell cultures may be needed for providing treatments (particularly, the developing world). The fixed nature also prevents past bioreactors from being adapted for a variety of uses.

A further issue relates to the ability of maximizing cell density for a given area. Many past proposals for bioreactors use fluidized beds. While such beds may work well for promoting cell growth and provide certain advantages, the resulting volume of space in the bioreactor required to create such a bed is large. Readily scaling a bioreactor with an unstructured or fluidized bed while achieving the desired cell growth is also challenging, and there is a current demand for bioreactors that may be utilized in a variety of operating conditions in the field (including, for example, within a sterile hood, cabinet or isolator where clearance may be limited).

Accordingly, a need is identified for an improved bioreactor that would be easy to deliver and assemble, particularly at remote locations, and/or would be readily adaptable for use in a variety of sizes or configurations, or for different applications or uses. In some embodiments of the disclosure, the present disclosure concerns systems and methods for the production of biologics. In particular, the production of cells, viruses or cells- or virus-derived products. In some embodiments, a bioreactor disclosed herein allows for high density cell growth. For example, density of at least 2 million cells/ml, at least 5 million cells/ml, at least 10 million cells/ml, at least 20 million cells/ml, at least 40 million cells/ml, at least 60 million cells/ml, or at least 100 million cells/ml. In some embodiments, the density can reach 300, 250 or 200 million cells/ml. In some embodiments, the bioreactor disclosed herein can have a total volume of at least 1 L, at least 10 L, at least 30 L, at least 40 L, or at least 50 L. In some embodiments, the bioreactor total volume can be at most 2500 L, at most 200 L, at most 150 L, at most 100 L, or at most 75 L. By bioreactor total volume reference can be made to the total liquid volume that can be introduced in the bioreactor, which will then be full. In an embodiment, the bioreactor comprises a drain for removal of excess products and fluids.

In some embodiments, the bioreactor may have a diameter of approximately 50-60 cm. In some embodiments, the bioreactor may have a diameter or height of approximately more than about 5, 10, 15, 20, 25, 30, 35, 40, 45, 50, 60, 70, 80, 90 or 100 cm. In some embodiments, a cover part or lid that may be used in connection with bioreactor may have a diameter of approximately more than 2, 4, 5, 6, 8, 10, 12, 15, 20, 25, 30 or 50 centimeters. In some embodiments, the overall bioreactor may have a height of approximately 20-50 centimeters.

In some embodiments, the bioreactor can be a perfusion bioreactor, wave bioreactor, cylindrical bioreactor, bag bioreactor, moving bed bioreactor, packed bed bioreactor, fibrous bioreactor, membrane bioreactor, batch bioreactor, continuous bioreactor or combinations of the foregoing. In some embodiments, the bioreactors can be made from or comprise a suitable material, for example, stainless steel, glass, aluminum, or plastic. In some embodiments, the bioreactor can allow for analysis of products.

Access to a bioreactor described herein can be via a lid, or door. In some embodiments, an access mechanism for the bioreactor can comprise for example, a lock and key mechanism, a pass code punch pad, card swipe, transponder reader, finger print scanner, retina scanner, sensors, automatic identification and data capture methods such as radio-frequency identification (RFID), QR code, biometrics (like iris or facial recognition system), magnetic stripes, Optical character recognition (OCR), smart cards, voice recognition, or any other access mechanism. In an embodiment, the access mechanism restricts access to the bioreactor itself. In another embodiment, the access mechanism restricts access to the bioreactor cabinet or the bioreactor chamber comprising the bioreactor. In another embodiment, the access mechanism restricts access to a process controller which controls the bioreactor and/or the entire production system.

In some embodiments, a bioreactor disclosed herein can comprise a process controller. In some embodiments, the biomolecule production system can comprise one or more process controllers. In an embodiment, one or more process controllers are configured to control both the bioreactor and the biomolecule production system. In some embodiments, the process controller is configured to control operations of a bioreactor and/or a biomolecule production system and can include a plurality of sensors, a local computer, a local server, a remote computer, a remote server, or a network. In some embodiments, the bioreactor and/or the biomolecule production system can include one or more sensors, for example, a temperature sensor (e.g., a thermocouple), flow rate sensor, gas sensor, level sensor or any other sensor. In some embodiments, the process controller can be operational to control aspects of a product manufacturing process, and can be coupled to sensors disposed in the bioreactor and/or the biomolecule production system, for example, to control the temperature, volume flow rate or gas flow rate into the bioreactor and/or the biomolecule production system in real time. In an embodiment, the process controller is divided in two parts, namely a Programmable Logic Controller (PLC) and a Supervisory Control and Data Acquisition (SCADA). The PLC is the intelligence of the system and is connected to the sensors and the actuators. The PLC contains only data and no power. The SCADA is important for visualisation, data historian and audit trail. This SCADA system runs on a server that stores the data historians and supports the visualization. In an embodiment, information can also be visualized from a client tablet. In an embodiment, the client network can be connected directly to the server for remote access. In some embodiments, a process controller can include a Human-Machine Interface (HMI), such as a display, for example, a computer monitor, a smart phone app, a tablet app, or an analog display, that can be accessed by a user to determine the state of the system (based on the sensors comprised in the system) and to control the system by means of various actuators, such as pumps, valves, heaters and agitators. In some embodiments, the process controller can include an input, for example, a keyboard, a separated smart tablet, a key pad, a mouse, or a touch screen, to allow a user to enter control parameters for controlling the operation of the bioreactor. In some embodiments, the process controller can control access to the bioreactor.

In some embodiments, the bioreactor disclosed herein can comprise and or contain sensors for monitoring different parameters. In an embodiment, the sensors can be electrically connected. In another embodiment, the sensors can be wireless. In another embodiment, the bioreactor comprises both electrically connected sensors and wireless sensors. In some embodiments, a sensor disclosed herein can be located in any compartment of a bioreactor disclosed herein. In some embodiments, sensors described herein can be a gas sensor (e.g. oxygen, nitrogen, or carbon dioxide), pH sensor, temperature sensor, cell density sensor, level sensor or dissolved oxygen (DO) sensor. In some embodiments, the sensors disclosed herein can measure amongst other things, biomass or cell density, the dissolved oxygen partial pressure, oxygen content, the pH value, the temperature, pressure, flow rate, level, certain concentrations of nutriments, such as lactate, ammonium, carbonates, glucose or any metabolic product or product to be metabolized which could for example reflect the cell density. In some embodiment, cell density (biomass density) can be determined by electrical impedance analysis or electrical impedance spectroscopy using an arrangement of measuring electrodes. In some embodiments, a bioreactor according to the disclosure can comprise sensors for measuring culture parameters. In some embodiments, a sensor disclosed herein can be in contact with culture medium in the bioreactor. In some embodiments, culture parameters can comprise amongst other things, the dissolved oxygen partial pressure, the pH, the temperature, the optical density, certain concentrations of nutriments, such as lactate, ammonium, carbonates, glucose or any metabolic product or product to be metabolized which could for example reflect the cell density. In an embodiment, the part of the sensor which is placed into the bioreactor (for instance a pH probe) is single-use, whereas the part of the sensor not in contact with the bioreactor is multi-use (such as the transmitter of a pH sensor). In some embodiment, a bioreactor disclosed herein can use regulation loops according to the disclosed parameters. In some embodiments, a regulation loop can for example, modulate the quantity of oxygen to be injected according to the value of the dissolved oxygen partial pressure present or the quantity of dissolved oxygen consumed by the cells; speed of circulation of the culture medium; inject $CO_2$ according to the pH value obtained by the sensors or any other type of regulation generally used in this type of culture. In some embodiments, cells can be exposed to dissolved oxygen concentrations of 300 mM or less (160 mmHg partial pressure), less than 200 mM, or between 20 and 150 mM. In some embodiments, cells can be exposed to about 0%, 1%, 5%, 10%, 20%, 30%, 40%, 50%, 60%, 70%, 78%, 80%, 90%, or 100% nitrogen and/or about 0%, 1%, 5%, 10%, 21%, 30%, 40%, 50%, 60%, 70%, 80%, 90% or 100% oxygen. In some embodiments, cells can be exposed to pure oxygen or an oxygen enriched atmosphere. In an embodiment, a sampling assembly can be connected to the biore-actor lid.

In some embodiments, a bioreactor disclosed herein may comprise heating and/or cooling devices, designed to heat and/or cool culture medium. In an embodiment, one or more or all containers in the biomolecule production system may comprise heating and/or cooling devices. In some embodiments, the heating device can be an electrical element, an electrical coil or any other heating means generally used in the field of cell culture, such as for example a thermostati-cally controlled double jacket. In an embodiment, the heat-ing means are heating plates. In an embodiment, the heating device comprises 7 elements. In a further embodiment, each element comprises a temperature sensor. In a further embodiment, each element comprises a temperature limiter. In a further preferred embodiment, the temperature limiter is set to 110° C. In some embodiments, cooling device may be any suitable cooling devices such as a Peltier element. In some embodiments, with regard to the culture medium and gas, the bioreactor comprises at least one inlet for the introduction of gas and/or culture medium and at least one outlet for the collection of the culture medium contained in the bioreactor. In some embodiments, mix of gas or gaseous mixture and culture medium can be supplied through the same supply line. In an embodiment, the bioreactor inlet comprises a pump for pumping fluids inside the bioreactor. In an embodiment, the bioreactor outlet comprises a pump for pumping fluids outside the bioreactor. In an embodiment, one or more pumps in the system are Watson-Marlow peristaltic pumps.

In an embodiment, the pH inside the bioreactor is adjusted by means of a base adjustment kit. In an embodiment, this base adjustment kit comprises two parts, a bag assembly, containing the base, and a transfer assembly to connect to the bioreactor and optionally to fill the bag. In an embodi-ment, the bag assembly is hung on a hook. In an embodi-ment, the bag assembly comprises a 5 L single-use bag. In a preferred embodiment, the attachment of the bag with the bioreactor comprises an aseptic connection. In an embodi-ment, the base is added to the bioreactor by means of a pump, such as a Watson-Marlow peristaltic pump.

In some embodiments, culture medium can be circulated in the bioreactor via an agitator. In some embodiments, an agitator can be a rotatable, non-contact magnetic impeller, a blade or screw agitation system, or an external circulation system. In some embodiments, the agitator can comprise a disk blade turbine, a curved blade turbine, an open blade fluid foil axial impeller, a turbine impeller with pitched blades, or a three-blade propeller. In a preferred embodi-ment, the bioreactor comprises a magnetic stirrer comprising 5 magnets. In a further preferred embodiment, the magnetic stirrer controls a propeller located in the bioreactor. In a further embodiment, the propeller is single-use. In some embodiments, the agitator can have a flow rate of less than about 0.01 l/min, 0.05 l/min, 0.1 l/min, 0.5 l/min, 1 l/min, 2 l/min, 5 l/min, 10 l/min, 15 l/min, 20 l/min, 50 l/min, 100 l/min, or 150 l/min to more than about 160 l/min, 180 l/min, 200 l/min, or 250 l/min. In a preferred embodiment, the rate of the agitator is controlled by means of the HMI.

In some embodiments, the bioreactor described herein comprises a fixed bed. In some embodiments, the fixed bed is a structured fixed bed (which means that it is formed of an easily replicated, generally homogeneous, substantially fixed structure, and thus is not randomly oriented or unstruc-tured, and, as can be appreciated, could take a variety of sizes or shapes while meeting this qualification). In some embodiments, the structured fixed bed comprises a stack of substrate disks. The substrate layers of the disks are stacked with the first or second side of a substrate layer facing a first or second side of an adjacent substrate layer. In some embodiments, the structured fixed bed extends spirally around a tubular part. In some embodiments, the structured fixed bed described herein can provide for a large cell growth surface within a small volume while still allowing circulation of medium and cells. In some embodiments, the structured fixed bed can be a mesh or comprises a mesh structure. In some embodiments, mesh structure or mesh can be a structure comprising a network or web-like pattern of filament, wire or thread. In some embodiments, the network can define pores, openings or perforations formed of a three-dimensional weave. In some embodiments, the struc-tured fixed bed described herein can comprise a tortuous path for cells and cell culture media. In some embodiments, the tortuous path or channel formed creates turbulence which facilitates cell and cell medium incursion into and/or through the structured fixed bed. In some embodiments the mesh structure is a cell immobilization structure. In some embodiments the mesh structure is or forms a spacer layer or section for flow of cells and medium. In some embodi-ments the mesh structure is both a cell immobilization and a spacer layer section.

In some embodiments, a spacer layer facilitates the tor-tuous path. In some embodiments, the structured fixed bed can comprise one or more cell immobilization layers having a surface which allows cells to adhere and grow upon and forming a cell immobilization section. In some embodi-ments, adjacent to the cell immobilization layers are one or more spacer layers. In some embodiments, the spacer layer can include a structure which forms a spacer section. In some embodiments, the spacer section allows passage of cells and medium through an open but tortuous path. In some embodiments, the structure or nature of the spacer layers can be chosen such that the spacer layers create a tortuous, open path for cells and culture media to travel in parallel to the surface of said spacer and cell immobilization layers. In some embodiments, the tortuous path or channel formed by the spacer section creates turbulence which facilitates cell and cell medium incursion into the immobi-lization layers.

In some embodiments, the spacer layer can be a mesh or comprises a mesh structure. In some embodiments, mesh structure or mesh can be a structure comprising a network or web-like pattern of filament, wire or thread. In some embodiments, the network can define pores, openings or perforations formed of a three-dimensional weave. In some embodiments, the spacer layers and/or the cell immobiliza-tion layers of a spacer section and a immobilization section can be made of a biocompatible polymer, for example polyester, polyethylene, polypropylene, polyamide, plasma treated polyethylene, plasma treated polyester, plasma treated polypropylene or plasma treated polyamide. In some embodiments, the spacer layer or the cell immobilization layer can comprise silica, polystyrene, agarose, styrene divinylbenzene, polyacrylonitrile or latex. In some embodiments, the layers can be hydrophilic or hydrophobic. In some embodiments, the cell immobilization layer can be hydrophilic. In some embodiments, a cell immobilization layer can be woven or nonwoven. In some embodiments, a cell immobilization section and a spacer section can be alternately positioned. In some embodiment, alternately positioned sections can alternate in a vertical position or in a horizontal position. In some embodiments, cell immobilization sections may be layered or alternately positioned in a vertical position or in a horizontal position. In some embodiments one or more layers may be connected. In some embodiments, one or more layers of cell immobilization layers can be superimposed on one or more spacer layers (or vice versa). In some embodiments, a structured bed disclosed herein can be tightly or loosely rolled to a structure such as a spiral structure, a monolith structure or varying shape or could be formed of layers one on top of one another with fluid flowing in parallel or perpendicular to the surfaces of the layers.

In some embodiments, the fixed bed growth surfaces may range from 1 m$^2$ to 2 m$^2$, 7-30 m$^2$, 150-600 m$^2$, 2,400 m$^2$, and may vary among different sizes (height or diameter) of bioreactors. As noted, a plurality of fixed beds may be provided in a stacked configuration, such as one, two, three, four, or more fixed beds. In an embodiment, said fixed bed growth surface may for instance be 200 m$^2$ or 600 m$^2$.

In some embodiments, an impeller speed may be adjusted to compensate for an increase in pressure drop so as to maintain consistent linear velocity from bottom to top of reactor or visa-versa. In such case, shear stress on cells can be maintained constant for all sizes of bioreactor. In some embodiments, a sparger may also be provided. In some embodiments, it may be desirable during sparging to cease operation of the impeller to avoid transporting the air bubbles into the fixed bed.

In some embodiments, one or more bioreactor parts are flexible. In some embodiments, one or more bioreactor parts are rigid. In some embodiments, one or more of the bioreactor parts comprise polycarbonate. In some embodiments the one or more bioreactor parts comprise rigid polycarbonate. In some embodiments, the bioreactor vessel comprises polycarbonate. In some embodiments, one or more bioreactor parts are injection molded.

In an embodiment, the system is provided with a bioreactor as described in PCT/EP2018/086394 which is herewith incorporated as a reference in its entirety. In short, a bioreactor is provided which may be in modular form, that utilizes one or more structured fixed beds to promote ease of manufacturing and use, while still achieving excellent cell culturing outcomes from the resulting homogeneity and repeatability afforded, even when scaled up or down.

In some embodiments, the modular bioreactor comprises a base portion having a first chamber, an intermediate portion forming at least part of a second, outer chamber for receiving the fixed bed and at least part of a third inner chamber for returning fluid flow from the second outer chamber to the first chamber, and a cover portion for positioning over the intermediate portion. The fixed bed may comprise a structured fixed bed, and the intermediate portion may comprise a tubular part, the structured fixed bed extending spirally around the tubular part, or the intermediate portion may comprise an inner wall of the fixed bed. In any embodiment, the intermediate portion may comprise a plurality of intermediate parts, each associated with a structured fixed bed.

In some embodiments, at least one of the plurality of intermediate parts is perforated for allowing fluid to flow from a first structured fixed bed below the at least one intermediate part to a second structured fixed bed above the at least one intermediate part. In some embodiments, each of the plurality of intermediate parts is tubular, and each structured fixed bed comprises a spiral bed wound around the tubular intermediate part. A perforated support may be provided for the structured fixed bed.

In some embodiments, the intermediate portion may further comprise a tubular casing for forming a periphery of the modular bioreactor. The tubular casing forms a space for heating, cooling, or insulating the bioreactor. The intermediate portion may comprise a plurality of intermediate parts, each adapted for connecting with each other.

In some embodiments, the intermediate portion includes a tube for engaging at least one intermediate part and forming an inner wall of the outer second chamber for receiving the fixed bed. The tube may engage wherein the tube engages a first intermediate part below the tube and a second intermediate part above the tube. The second intermediate part may include openings for creating a fluid film along the third inner chamber. Supports, such as vertical rods, may be provided for supporting the second intermediate part from the first intermediate part.

In some embodiments, the cover portion comprises a cap including a plurality of ports. In some embodiments, the cover portion comprises a removable cap. The removable cap may have an outer diameter that is less than an outer diameter of the intermediate portion. The removable cap may have an outer diameter that is more than an outer diameter of the intermediate portion. At least one of the ports may include a threaded metal insert. The cover portion may have an outer diameter that is equal to or greater than an outer diameter of the intermediate portion.

The intermediate portion may comprise an intermediate part adapted for positioning at least partially within the base portion. The intermediate part may further include a flow disruptor for disrupting fluid flow.

The base portion may include a further chamber radially outward of the first chamber in fluid communication with the second outer chamber including the fixed bed. This further chamber may be formed in part by an upstanding wall having a plurality of openings for transmitting fluid from the first chamber to the further chamber.

In some embodiments, an agitator is associated with the base portion. The intermediate portion may be adapted for suspending the agitator in the first chamber in a manner that allows side-to-side movement for alignment with an external drive.

In some embodiments, a container is provided for containing the agitator. In some embodiments, the container includes a central inlet and a plurality of radially oriented outlets. A flow divider may be associated with the central inlet. In any embodiment, or as an independent component separate from any bioreactor, the agitator may comprise a plurality of curved blades.

In some embodiments, a plurality of flow disruptors are provided for dividing the fluid flow entering the third inner chamber into a plurality of streams. The plurality of flow disruptors may be associated with a ring. In some embodiments, one or more conduits for permitting gas to enter into a space behind one of the streams are provided. The one or more conduits may be connected to a structure including the plurality of flow disruptors. For example, a first conduit may be connected to the structure, or both first and second conduits may be connected to the structure. Alternatively, the first and second conduits may not be connected to the structure.

According to a further aspect of the disclosure, an apparatus for culturing cells is disclosed. The apparatus comprises a modular bioreactor comprising a base portion removably connected to both a central column and/or an outer casing, the outer casing and central column together forming a compartment for culturing cells.

In a possible embodiment, each of the plurality of stacked, structured fixed beds is wrapped around the central column. The central column comprises first and second interconnected tubes, a first structured fixed bed of the plurality of structured fixed beds being wrapped around the first tube and a second structured fixed bed of the plurality of structured fixed beds being wrapped around the second tube. In some embodiments the central column comprises first and second tubes for engaging a perforated support extending between at least two of the plurality of structured fixed beds.

In any embodiment, the structured fixed bed may comprise a cartridge adapted for being inserted into and removed from the second, outer chamber or compartment.

According to another embodiment of the disclosure, a bioreactor for culturing cells is provided. The bioreactor may comprise a base part having a first chamber adapted for receiving an agitator for agitating a fluid. A first central column may be attached to the base part, optionally removably, the first central column forming at least part of a second, outer chamber for culturing cells and a third inner chamber for returning fluid flow from the second outer chamber to the first chamber.

In this or other embodiments, the second, outer chamber includes a first structured fixed bed. In this or any embodiment, the first structured fixed bed comprises a spiral bed, and may be wound or wrapped around the first central column. A second central column may also form at least part of the second outer chamber, and further including a second structured fixed bed spaced vertically from the first structured fixed bed. A perforated support may be provided between the first structured fixed bed and the second structured fixed bed.

In any embodiment, the second, outer chamber includes an unstructured bed.

According to yet another embodiment of the disclosure, a bioreactor for culturing cells in connection with a fluid is used. The bioreactor comprises a first chamber including an agitator for agitating the fluid, a second, outer chamber including a plurality of stacked beds for culturing cells, and a third, inner chamber for returning fluid from the second outer chamber to the first chamber. In another embodiment, the bioreactor comprises a first chamber including an agitator for agitating the fluid, a second, inner chamber including a plurality of stacked beds for culturing cells, and a third, outer chamber for returning fluid from the second inner chamber to the first chamber.

In some embodiments, the bioreactor comprises a base portion having the first chamber, an intermediate portion forming at least part of the second, outer chamber and at least part of the third inner chamber, and a cover portion for positioning over the intermediate portion. In this or other embodiments, the intermediate portion comprises a first support for supporting a first bed of the plurality of stacked beds. The intermediate portion comprises a second support for supporting a second bed of the plurality of stacked beds, and may be adapted for removably connecting with the base portion and the cover portion.

In some embodiments, the second, outer chamber is bounded by an outer wall. The bioreactor may further include an outer casing forming a space with the outer wall, the space being for insulating, heating, or cooling the second, outer chamber.

Still another aspect of the disclosure pertains to a bioreactor that is used in conjunction with said bioreactor platform, said bioreactor is suited for culturing cells in connection with a fluid. In an embodiment, the bioreactor comprises a first chamber including an agitator for agitating the fluid, a second, outer chamber including at least one bed for culturing cells, and a third, inner chamber for returning fluid from the second outer chamber to the first chamber. The second, outer chamber may be bounded by an outer wall, and further including an outer casing forming a space with the outer wall, the space being for insulating, heating, or cooling the second, outer chamber. In another embodiment, the bioreactor comprises a first chamber including an agitator for agitating the fluid, a second, inner chamber including at least one bed for culturing cells, and a third, outer chamber for returning fluid from the second inner chamber to the first chamber. The third, outer chamber may be bounded by an outer wall, and may further including an outer casing forming a space with the outer wall, the space being for insulating, heating, or cooling the third, outer chamber.

In this or any other embodiments, the at least one bed comprises a structured fixed bed, such as a spiral bed or a stacked/layered bed, but could also be an unstructured bed. The inner chamber may be formed by at least one tube (which may be separate from or part of the bed). The at least one tube may be connected to first and second supports bounding the at least one bed. The first and second supports may be connected to the outer wall, or the first and second supports may be at least partially perforated.

This disclosure also relates to bioreactor comprising first and second stacked, structured beds. The bioreactor may further include a screen engaging both the first and second stacked, structured beds. The first and second stacked beds may comprise structured beds, such as spiral beds.

Also disclosed is a bioreactor including a structured fixed bed forming a central column of the bioreactor. The structured fixed bed may comprise a spiral bed. An inner surface of the structured fixed bed is fluid-impervious, such that a central column is formed for returning fluid to recirculation through the structured fixed bed, such as from top to bottom. The bioreactor may be modular, and a plurality of stacked, structured fixed beds may be provided, possibly with a gap or spacer between each bed in the stack.

Compact bioreactors such as the ones described herein may have the drawback that the inoculum should be concentrated (e.g. by centrifugation) as the bioreactor can otherwise not accommodate the volume of the inoculum (maximum working volume−minimum working volume<non-concentrated inoculum). In some occasions this may require to partially empty the bioreactor to reach the minimal working volume.

Typically, an amount of 5.000 to 25.000 cells/m$^2$ bioreactor surface is required. For a bioreactor of 600 m$^2$ this equals to an amount of $3\times10^{10}$ to $15\times10^{10}$ viable cells. This is a considerable amount, and equals the cell harvest of 9 to 10 cell factories.

The presence disclosure also relates to a method for inoculating a bioreactor without having to concentrate said inoculum. To that purpose, the current disclosure describes a methodology wherein a bioreactor is inoculated in recirculation mode and wherein the inoculum recipient is changed at a later phase in the process.

In an embodiment, the method comprises the following steps:

filling a bioreactor with medium and equilibrating the pH of said medium preparing an inoculum comprising a sufficient amount of cells in a cell medium volume, wherein the inoculum is not concentrated (for instance by centrifugation). As an example, a 6 L inoculum can be prepared for a 150 m$^2$ bioreactor. The inoculum is placed in an inoculum recipient, for instance a bag or bottle The inoculum recipient is connected to the bioreactor and preferably gently agitated by any means known in the art and suitable for said purpose A circulation loop between the bioreactor and inoculum recipient is established, allowing the circulation of cells with medium from said recipient to said bioreactor and back. The circulation may continue for a suitable amount of time, depending on the volume of the inoculum and the size of the bioreactor. Circulation time may typically range from 1 hour to 10 hours, or from 1 to 4 hours. By that time, viable cells should be attached and fixed to the fixed bed present inside said bioreactor. Non-viable cells will remain into suspension, either in the bioreactor or in the recipient.

Once the circulation period is ended, the inoculum recipient is de-coupled from said bioreactor Cells are allowed to grow inside the bioreactor (batch growth), followed by a recirculation of fresh media, not containing cells, or by means of a recirculation mode with a recirculation media vessel, preferably a single use vessel. In one embodiment said vessel is a bag.

The method as described above does not require concentration of the cell inoculum and also prevents the risk of having non-viable or non-attached cells in the recirculation loop. The method provides an efficient manner of inoculating compact (fixed bed) bioreactors thereby assuring high cell density while still allowing a low working volume. The method also allows removing any unwanted excipients that have been used to harvest cells (such as for instance trypsin) and that otherwise negatively could impact cell growth. In an embodiment, the inoculation density of the bioreactor is between $1 \times 10^3$ and $1 \times 10^4$ cells/cm$^2$, more preferably between $2 \times 10^3$ and $8 \times 10^3$ cells/cm$^2$, such as $5 \times 10^3$ cells/cm$^2$. In an embodiment, the cell density at harvest is between $5 \times 10^4$ and $5 \times 10^5$ cells/cm$^2$, more preferably between $1 \times 10^5$ and $4 \times 10^5$ cells/cm$^2$, such as $1.5 \times 10^5$ cells/cm$^2$.

In an embodiment, the current disclosure thus describes:

A method for inoculating a fixed bed bioreactor comprising the steps of:

coupling an inoculum recipient comprising an amount of cells in a volume of medium to a bioreactor provided with a medium volume;

allowing the content of said inoculum recipient to circulate to said bioreactor and back to said recipient, thereby allowing the cells to populate said fixed bed; and decoupling said recipient from said bioreactor once circulation has ended.

Said method is used to inoculate a bioreactor present in a system as described herein.

In a preferred embodiment, media conditioning can be performed within the bioreactor vessel.

In another embodiment (e.g., with a bioreactor which utilizes recirculation into a separate media conditioning vessel during cell growth phase), two recirculation steps are employed: a first recirculation is introduced during the inoculation, and a second recirculation step is employed during the growth of the cells.

In an embodiment, a (re)circulation loop for media conditioning may be provided as well. This loop fluidly connects the fixed bed reactor to a media conditioning vessel, thereby supplying a cell culture media within the conditioning vessel to the bioreactor. The media from the media conditioning vessel is delivered to the bioreactor via an inlet, which may also include an injection port for cell inoculum to seed and begin culturing of cells. The bioreactor vessel may also include one or more outlets through which the cell culture media exits the vessel. In addition, cells or cell products may be output through the outlet. To analyze the contents of the outflow from the bioreactor, one or more sensors may be provided in the line. In some embodiments, the system includes a flow control unit for controlling the flow into the bioreactor. For example, the flow control unit may receive a signal from the one or more sensors (e.g., an $O_2$ sensor) and, based on the signal, adjust the flow into the bioreactor by sending a signal to a pump (e.g., peristaltic pump) upstream of the inlet to the bioreactor. Thus, based on one or a combination of factors measured by the sensors, the pump can control the flow into the bioreactor to obtain the desired cell culturing conditions.

The media conditioning vessel can include sensors and control components found in typical bioreactor used in the bioprocessing industry for a suspension batch, fed-batch or perfusion culture. These include but are not limited to DO oxygen sensors, pH sensors, oxygenator/gas sparging unit, temperature probes, and nutrient addition and base addition ports. A gas mixture supplied to sparging unit can be controlled by a gas flow controller for $N_2$, $O_2$, and $CO_2$ gasses. The media conditioning vessel also contains an impeller for media mixing. All media parameters measured by sensors listed above can be controlled by a media conditioning control unit in communication with the media conditioning vessel, and capable of measuring and/or adjusting the conditions of the cell culture media to the desired levels. In an embodiment, the media conditioning vessel is provided as a vessel that is separate from the bioreactor vessel. This can have advantages in terms of being able to condition the media separate from where the cells are cultured, and then supplying the conditioned media to the cell culture space.

Hence, the system as described herein may be provided with means for coupling an inoculum recipient to said bioreactor and means for allowing the recirculation of the inoculum and optionally also fresh of conditioned medium to said bioreactor. The inoculum recipient could be present in any of the three chambers (bioreactor, process or downstream chamber) as described herein, but is preferably present in said bioreactor chamber. In an embodiment, the inoculum is provided on a skid.

In a further aspect, the current disclosure also concerns a system for the production of biomolecules, said system comprises at least one process chamber comprising one or more purification or filtration devices allowing the purification or filtration of a biomolecule of a cell harvest and a bioreactor chamber, suited to receive a bioreactor. In one embodiment said bioreactor chamber is provided with a connector allowing the transmission of power, signals and/or data when paired with a bioreactor cabinet comprising a bioreactor. In an embodiment, the system is coupled to a further module, such as a module for additional processing, formulation or packaging.

In a preferred embodiment the system can be assembled in packages that can pass through a door of 93 cm×200 cm. In addition, the design of the system is made to ease the maintenance, where each critical part can be easily removed by 2 technicians without any lift or other specific tools and where the maintenance last less than 2 hours per part.

The general casing is the main structure of the system. In a possible embodiment the dimensions are 2445 mm×2496 mm×950 mm. In some embodiments, the length of the system can be reduced depending on the number of filters in the process chamber and the downstream chamber. In one embodiment, the general casing comprises a footprint between about two and about ten square meters; preferably the footprint is between about three and about five square meters, and more preferably, the footprint is about 3 square meters.

In another or further embodiment, the system is provided with a bioreactor as described in PCT/EP2020/084317 and US 2021 002 486 8, which is considered to be incorporated herein by reference in its entirety. In short, the bioreactor includes a fixed cell culture bed and an agitator for pumping liquid through the cell culture bed, wherein the agitator is placed in a container. In an embodiment, the agitator is connected to a conduit. In an embodiment, the conduit comprises an injector for delivering gas bubbles into the container. In an embodiment, the agitator converts the bubbles originating from the injector into second bubbles having a second, smaller size than the first size for delivery to the cell culture bed with the liquid. Given their smaller size, the second bubbles are better able to pass into and through channels formed by the spacer layers and the adjacent cell immobilization layers (or other available paths) of the fixed bed. This serves to further enhance the oxygenation of the cells being grown in the bed, without a corresponding need to increase the speed of the impeller and the resulting liquid flow rate. Moreover, the release of the gas into or near the agitator container and the resulting flow avoids the creation of deleterious air pockets in the bioreactor, which are notoriously difficult to remove without halting the bioreactor operation.

In an embodiment the system is equipped with control software. This software enables the gathering, transmission, processing and visualisation of parameter measurements in the system. In addition, the control software will be able to adjust these parameters. Parameters include but are not limited to pH, temperature, dissolved oxygen, volume, nutrients, level and transmembrane pressure. In an embodiment, the control software is able to display alarm signals when the system does not operate appropriately. In an embodiment, it is possible to access the system remotely via connection to a network. In an embodiment the system is controlled by the user through a smart tablet connected to the control system.

In some embodiments, the system is a mobile system, comprising wheels or tracks to allow transport.

In an embodiment the system is designed to be installed against a wall. In a preferred embodiment, the system is installed on wheels, allowing the system to be moved for maintenance access when in non-production. In some embodiments, the wheels can be equipped with brakes and a directional lock. This will prevent unnecessary movement of the system.

In a preferred embodiment, each chamber comprises a wall or back sheet opposite to an operation area of said chamber, said wall or back sheet is provided with one or more instruments chosen from pumps, pipings, electrical sockets and/or manifolds needed for allowing functioning of said chamber.

Said back sheet is by preference a vertical metal sheet at the back of the chamber, limiting said chambers. In one embodiment, the back sheet supports process instruments and single use manifolds used in at least a corresponding chamber. In a further embodiment, the back sheet is supporting all process instruments (i.e. pumps, valves, sensors) and single-use manifolds. In an embodiment, modular back sheet templates, different back sheets with specific hardware, can be designed, depending on the processes to be executed in the system, allowing interchangeability and easy development for future customer need or requirement. The back sheets can be adapted and assembled together to fit different process needs. Furthermore, the combination and position of these back sheets can be adjusted onsite at any point in order to facilitate multi-product manufacture. Each back sheet is designed with all equipment's and devices accessible by the operators, while in the back of this sheet all technical components are installed like motors, network cables, power supply, etc. This design allows easy maintenance, increased accessibility, particle reduction and increases safety.

In some embodiments, the user handling area of each chamber in the system is shielded with a front window. In one embodiment, said front window is preferably provided with a gap to allow access during operation. In a further embodiment the front window is sealable. In an embodiment, the window openings can be locked by a locking device. In an embodiment, said locking device can be controlled by the control software. In an embodiment, the software sends a command to lock the locking device as soon as the process is ready to start and to keep the locking device locked for the full process duration. In an embodiment, the lateral left door of the chamber is provided with a locking device. In an embodiment, said locking device is an electromagnet consisting of a powered part and a stainless steel part which become blocked once power is added. In an embodiment, the 2 parts are blocked with a force of 1000N. In an embodiment, the window openings are locked with more than one locking device. In an embodiment, the window openings are locked with 3 locking devices. In an embodiment, the windows are locked during operation of the system. In a further embodiment, an emergency stop of the system is activated, meaning all the moving actuators are stopped into the process chamber and process is set on hold, when force is applied to the locked windows. By locking the windows and the lateral doors, the safety of the operator and the efficiency of the laminar air flow (coming from the top of the chamber) are guaranteed.

In an embodiment the general casing of the system has front windows with a gap of 100 to 300 mm, such as 200 mm with the work space. This gap allows the evacuation of the air from the process chamber and gives access during operations. The overall design allows the operators to stay in front of the chamber. The windows may be made of any material suitable in the art such as (thermo)plastic or glass. In a specifically preferred embodiment, said windows are made of plexiglass. Plexiglass has a light weight and is more shatter-resistant than glass.

In an embodiment the windows can be opened, to allow further accessibility by the operator. Said windows may be opened in a vertical manner, opening towards the side of said system or chamber, or in a horizontal manner, towards the top of the system. The opening and closing of the windows may be manually or automatically operated.

In order to be able to fully operate and execute the task of producing or purifying the desired biomolecules, said bioreactor chamber will be equipped with a bioreactor cabinet, wherein said bioreactor cabinet is connected to the system by means of a connection system, comprising a connection part and a receiving part on the bioreactor cabinet and on the system.

In one embodiment, a connection between the bioreactor cabinet and the system will allow docking of the bioreactor cabinet to the system and ensures that both entities are firmly connected to each other, prohibiting the release of the bioreactor cabinet from the system during the production of biomolecules. In a preferred embodiment the connection is magnetic. Said magnet may be an electro magnet, wherein magnetic field is produced by an electric current. The main advantage of an electromagnet over a permanent magnet is that the magnetic field can be quickly changed by controlling the amount of electric current. In the current application, the use of a magnet, more specifically an electro magnet enhances the safety of the system, as it will prevent unauthorized docking or removal of the bioreactor cabinet to or from the production system. Said system may be comprised of a corresponding magnetic part to allow interaction with the magnet of said bioreactor cabinet. In an embodiment, said magnetic connection is controlled by the software.

In order to allow docking and functioning, the bioreactor cabinet is also provided with a connector allowing the transmission of power, signals and/or data when paired with a biomolecule production system and a connection, preferably magnetic, for allowing the connection to said biomolecule production system. In an embodiment, said connector may be comprised of a connecting portion and receiving portion, wherein said connecting portion may be present on said bioreactor cabinet and said receiving portion may be present at a recess in said bioreactor chamber; or vice versa. In an embodiment, the powered part of the magnetic connection is provided on the system and the stainless steel part of the magnetic connection is provided on the back of the bioreactor cabinet. In an embodiment the 2 parts become blocked once power is added. In an embodiment, the 2 parts are blocked with a force of 1000N.

In an embodiment, a male connector of the bioreactor cabinet is connected to a female connector of the production system. In a preferred embodiment, to ensure correct connection between the male and female connector, the female connector contains centering pins.

In a preferred embodiment, the connector can be a modular connector system allowing combinations of power and signal contacts, Ethernet, optical fiber, coaxial contacts, hydraulic, pneumatic and thermocouplings in a compact frame or housing. This modular connector system can be configured according to the specific requirements of the connection. In a preferred embodiment the connectors are waterproof.

The bioreactor cabinet will be connected to the bioreactor chamber with an industrial connector providing a reliable and pluggable transmission of the power, signal and data.

By preference, said bioreactor cabinet is a bioreactor cabinet as described above. In some embodiments, the bioreactor cabinet of the system protrudes from the processing chamber plane. This provides better ergonomic conditions for the operators using the system, allowing them more easy access to the various elements in the bioreactor cabinet.

In an embodiment, the bioreactor cabinet and bioreactor chamber are able to function as a standalone biomolecule production system. In another embodiment, the bioreactor chamber and bioreactor cabinet are connected to one or more upstream (process chambers) or downstream chambers.

In an embodiment, the bioreactor cabinet is first connected to the bioreactor chamber and afterwards the bioreactor cabinet and bioreactor chamber are connected to an upstream (process chamber) or downstream chamber for purification or clarification.

In an embodiment, the bioreactor chamber and the process chamber (either for upstream or downstream processing) are preassembled. In an embodiment, the bioreactor chamber is connected to a downstream chamber. In another embodiment, the bioreactor chamber/process chamber assembly is connected to a downstream chamber.

The system and the chambers of said system will be equipped with devices that allow further purification or filtration of the harvest of said bioreactor. The harvest can comprise of medium originating from the bioreactor or can be a lysate of the cells cultured in the bioreactor. Said purification means can be a combination of one or more of clarification, flocculation, precipitation of cell debris, lipids, host cell proteins, DNA, as well as ultrafiltration, tangential flow filtration aiming at concentrating the supernatant, or changing the chemical conditions (such as pH, conductivity, ionic strength). Said means can also be chromatographic means, in capture mode or in flow through mode; chromatography can be envisaged both in a packed mode, a monolith mode, a membrane-based mode or in a fluidized mode; should the chromatography be implemented in a fluidized mode, it can include the use of classical media separated by settling or centrifugation, or (para)magnetic media separated by an external magnetic field. It can be any combination of any of the means described previously.

Such devices may include but are not limited to one or more chromatography column such as such as affinity chromatography, ionic exchange chromatography (e.g. anion or cation), hydrophobic interaction chromatography, size exclusion chromatography (SEC), immuno-affinity chromatography which is a column packed with an affinity resin, such as an anti-IgM resin, a Protein A, a Protein G, or an anti-IgG resin or any combination. Anion exchange exploits differences in charge between the different products contained in the harvested supernatant. The neutrally charged product passes over the anion exchange chromatography column cartridge without being retained, while charged impurities are retained. The size of the column may vary based on the type of protein being purified and/or the volume of the solution from which said protein is to be purified.

To that purpose, and in an embodiment, said bioreactor chamber is provided with a concentrator, such as a TFF and optionally a fluid collection vessel, suited to receive outflow from said concentrator and recycling it back to said concentrator or to a downstream process. In a preferred embodiment, said concentrator such as TFF as well as fluid collection vessel are connected to said back sheet of said bioreactor chamber.

In an embodiment, the bioreactor of the chamber and the concentrator are connected by a conduit facilitating liquid transport from said bioreactor to said concentrator. Alternatively, when a vessel is included in the system, the bioreactor and the vessel are connected by a conduit, facilitating liquid transport from the bioreactor through an inlet to said intermediate vessel. In addition, the vessel and the concentrator are also connected by a concentrator feed conduit which allows liquid transport from the vessel to the concentrator. In a preferred embodiment, the concentrator is controlled by one or more valves, such as pinch valves. In an embodiment, the liquid is pumped from the collection vessel to the concentrator by means of pump. In a further embodiment, the pump is a single-use pump. In a preferred embodiment, the pump is a single-use diaphragm pump. In an embodiment, the collection vessel comprises a conduit allowing the fluid to by-pass the concentrator. Finally, a conduit facilitating liquid transport from the concentrator to the bioreactor can also be provided. In a preferred embodiment, the collection vessel comprises an inlet for small additions. In a preferred embodiment, the collection vessel comprises an inlet for $CO_2$. In a preferred embodiment, the collection vessel comprises an inlet for one or more buffers. In one embodiment, the collection vessel comprises one or more level sensors. In a preferred embodiment, the collection vessel comprises a conduit for connection to a bubble trap. The generation of foam during the course of a bioprocess remains a major technological challenge to be resolved. The foaming tendency of the cultivation media used in bioreactors induces various direct, that is microbial cells stripping and contamination, as well as indirect adverse effects, that is modification of the properties of the medium subsequent to the addition of chemical antifoam leading to toxic effects at the level of the microbial metabolism and fouling of the downstream processing equipment. In an embodiment, the system comprises a foam trap to remove foam from the system.

In an embodiment, the collection vessel comprises one or more handles for easy transport of the collection vessel. In an embodiment the intermediate vessel may be single-use, disposable and/or autoclavable. The shape of said vessel may be any kind of shape known to the skilled person and suited for its purpose.

In an embodiment, one or more parts of the system are installed and/or removed in the system by means of a lift. In an embodiment, the concentrator (for instance a TFF cartridge), the collection vessel, a pump head and required tubing are transported by means of a lift. In an embodiment, the lift comprises wheels to transport the various parts to be installed, and a holder to grasp the various parts. In an embodiment, the lift grasps the collection vessel (and connected parts) by positioning the holder in between the handles of the collection vessel.

In an embodiment, one or more vessels of the system, such as the collection vessel and the bioreactor, are single-use. In an embodiment, one or more of the vessels of the system are rigid. In an embodiment, one or more of the vessels of the system are flexible. In an embodiment, sensors, such as level sensors, flowmeters, pressure sensors, temperature sensors or pH sensors, are present in or connected to one or more vessels of the system. In an embodiment, the sensors are single-use. Flow meters allow non-invasive fluid monitoring from the outside through the tubing. In an embodiment, a flow meter is located after a filtration pump and is used to measure the filtration flow. In an embodiment, the flow meter is located on the permeate conduit and is used to measure the permeate flow. Pressure sensors protect the system from overpressure. In a preferred embodiment, a single pressure sensor is located downstream of every pump in the system. In an embodiment, the level measurement of the collection vessel is done with three capacitive level sensors that measure the level on a 20 cm range. In an embodiment, a portion of the level sensors is located in the process chamber on the back sheet and needs to be in contact with the collection vessel to operate. The level sensors enable to continuously measure the liquid level in the collection vessel. In an embodiment, the system comprises one or more pH sensors. In an embodiment, the bioreactor comprises a pH sensor. In an embodiment, the collection vessel comprises a pH sensor. In an embodiment, the pH sensor comprises a pH probe in contact with the fluid inside the collection vessel and a transmitter. In an embodiment, the pH probe is single-use. In an embodiment, the pH probe is multi-use. In an embodiment, the transmitter is single-use. In an embodiment, the transmitter is multi-use. In a preferred embodiment, the pH probe is single-use and the transmitter is multi-use. In an embodiment, the gas flow to the bioreactor and the collection vessel is controlled by means of one or more mass flow controllers (MFCs). In an embodiment, 3 MFCs are used to control pH and DO inside the bioreactor with respectively air, CO2 and O2. In an embodiment, one MFC is used to control DO inside the sparger with O2. In an embodiment, one MFC is used to control the pH in the collection vessel with air or CO2. In an embodiment the MFCs are grouped in a MFC block. In a further embodiment, the MFC block is situated inside the bioreactor cabinet. In an embodiment, the MFC block is located in the electrical cabinet of the bioreactor chamber.

The system's concentrator can be chosen from a number of devices known to the skilled person which are suited for reducing the volume of the liquid in which the target biomolecule resides. In some embodiments, the concentrator comprises one type of concentration device (e.g., tangential flow filter). In some embodiments, the concentrator comprises more than one type of concentration device (e.g., tangential flow filter and dead-end filter). Most of these devices are based on filtration and/or size exclusion chromatography. In one embodiment the concentrator is a filtration device, more preferably a micro-filtration device, or an ultra-filtration device or a combination of both micro- and ultra-filtration device. When the system is provided with an ultra-filtration device for reducing the volume of the liquid in which the target biomolecule resides, the membrane of the device is adapted as to allow flow through of water and low molecular weight solutes, which are in general referred to as the permeate, while macromolecules such as biomolecules are retained on the membrane in the retentate.

In an embodiment, said TFF is equipped with at least one hollow fiber having pores with a porosity sufficient to retain practically all of the target biomolecules, while permitting smaller contaminants such as growth medium and solutes to pass through the pores of the membrane. In contrast to dead-end filtration, in which the liquid is passed through a membrane or bed, and where the solids are trapped on the filter, tangential flow across the surface of the filter is allowed in the TFF device, rather than directly through the filter. Accordingly, formation of a filter cake in the TFF is avoided. In another embodiment, said TFF may be equipped with a cassette/cartridge allowing tangential flow filtration. In yet another embodiment, said TFF is a single pass tangential flow filtration (SP-TFF). This device is especially advantageous when purifying proteins such as antibodies. In some embodiments, the TFF comprises a membrane with an area of between about 1000 $cm^2$ and 2000 $cm^2$, preferably about 1500 $cm^2$. The TFF may be reused, for one time use and/or disposable. In some embodiments, the TFF is plug and play.

In a further embodiment, a kit is provided, wherein the kit comprises a TFF cartridge and one or more pre-assembled manifolds. Preferably the one or more manifolds comprise tubing, sterile connectors and optionally one or more pressure sensors. In one embodiment, the one or more pressure sensors are disposable.

As mentioned above, the system is provided with a retentate conduit mediating recirculating of the retentate to an input of the bioreactor or an input of a vessel. An additional advantage of implementing a TFF device as a concentrator in the system is that the TFF device is suited to be operated in a continuous perfusion process. This allows significant concentration of the culture volume.

In a preferred embodiment the collection vessel with the TFF attached is located at the center of the bioreactor chamber behind the bioreactor. The TFF is connected to the collection vessel with a support. The collection vessel—TFF—and TFF pump assembly is attached to the back-ground metal sheet of the system. In one embodiment, the collection vessel and the TFF are installed and uninstalled once the bioreactor cabinet is removed. In a further embodiment, for reagent addition of less than 5 liters, supports are created in the bioreactor chamber to hang bags.

In one embodiment, the collection vessel is filled with the cell harvest of the bioreactor using a pump. The manifold connection of the collection vessel-TFF to the bioreactor or to the bubble trap is done with an aseptic connection. Benzonase addition and NaCl are prepared in bags that will be hanged inside the process chamber with bag supports (i.e. hooks). In one embodiment, these two products are added with one single pump to the collection vessel. The volume accuracy requires to fill the bag with the exact reagent quantity or to control the peristaltic pump with a flowmeter. The homogeneity inside the collection vessel is guaranteed with the recirculation loop through the TFF with the TFF pump. The waste coming from the permeate line is collected in a waste tank/vessel/bag/line (outside the system) and connection to this waste tank/vessel/bags/line is done with an aseptic connection. In a preferred embodiment, the tank/vessel/bags/line should have a vent system and/or a check valve to avoid any backflow and ideally a disconnection system. In some embodiments, the product is sent to devices that allow further purification or filtration after the concentration in the TFF. A bubble detector may be located just before those purification or filtration devices allowing to detect when the collection vessel is empty and to determine the presence of gas bubbles or liquid. In an embodiment, the bubble detector comprises an ultrasonic sensor. In one embodiment, to minimize the product loss, the collection vessel and the TFF are rinsed. In one embodiment, the rinsing comprises the addition of chasing buffer inside the collection vessel and the TFF loop and optionally recirculating the chasing buffer in the loop for a certain time to reduce the product. After the rinsing, process air is sent to the inlet of the TFF to push the product and reduce as much as possible the dead volume. In a further embodiment, the drain of the collection vessel also allows to reduce the void volume. In an embodiment, a sampling assembly is connected to the collection vessel, for collecting samples. In a further embodiment, the sampling assembly is connected to the top of the collection vessel.

The general purpose of the collection vessel is to have a gamma irradiated "plug and play/ready to use" solution. In an embodiment the vessel has been designed in polypropylene with the possibility to hang a TFF on the side using holders. The TFF selected is gamma irradiated and with a complete gamma stable manifold (collection vessel+pump+TFF).

An embodiment of the system according to the current disclosure, comprises in the first place a bioreactor chamber containing a bioreactor cabinet including a bioreactor. Processes in the bioreactor produce biomolecules from cultured cells. The resultant product is optionally purified in the process chamber which is fluidly connected and adjacent to the bioreactor chamber. In an embodiment, the cultured cells are lysed before further processing. In an embodiment, DNA is removed from the cultured cells before further processing. This process chamber comprises one or more purification, clarification or filtration devices allowing the purification or filtration of a biomolecule of a cell harvest.

In another or further aspect, said disclosure also pertains to a system for the production of biomolecules, comprising a process chamber comprising one or more purification, clarification or filtration devices allowing the purification, clarification or filtration of a biomolecule of a cell harvest, a downstream chamber and a bioreactor chamber, suited to receive a bioreactor, wherein said bioreactor chamber is positioned in between said process chamber and said downstream chamber, and is fluidly connected to both chambers, wherein said bioreactor chamber is provided with a connector allowing the transmission of power, signals and/or data when paired with a bioreactor cabinet comprising a bioreactor and a connection system for allowing the connection to said bioreactor cabinet. In another embodiment, the bioreactor chamber is not positioned in between the process chamber and the downstream chamber, but is positioned on the outside of the system.

In an embodiment, fluidly connected includes one or more intervening manifolds, vessels, devices etc.

In an embodiment, said one or more filtration or purification devices are in liquid connection with an outlet line, said outlet line comprises a section that is positioned parallel to said filtration or purification devices and rises in a vertical direction, allowing for a vertical flow in said outlet line.

In an embodiment the process chamber contains an in-depth filtration system. The number of filters in this filtration system is flexible. In an embodiment, one or more of the walls of the process chamber are free standing, allowing expansion of the process chamber and the addition of extra filters in the filtration system. As the filters are located on the side of the system, the design is quite flexible if a huge number of filters must be added. The number of filters will have a direct impact on the dimensions of the system. In an embodiment, the in-depth filtration system comprises one or more high-performance polyethersulfone (PES) liquid filters.

In one embodiment, the process chamber includes equipment, instruments and single use manifolds required for performing the processes in that chamber. In one embodiment, the process chamber includes equipment, instruments and single use manifolds required for the production of biomolecules. In a further embodiment, the process chamber includes equipment, instruments and single use manifolds required for the gene therapy process. In another embodiment, the process chamber includes equipment, instruments and single use manifolds required for the production of antibodies. In another embodiment, the process chamber includes equipment, instruments and single use manifolds required for the production of viral vaccines. The process chamber design must ensure easy accessibility of instruments, devices, manifold, aseptic connections. The working space is located at around 90 cm from the ground to allow the operators to perform procedures standing up.

The processes performed in the process chamber can be subdivided in one or more modules. In one embodiment, the process chamber comprises a plurality of modules. In a further embodiment, hardware associated with one or more modules is installed or at least partially installed on one or more panels. In a still further embodiment, each module is one (or multiple) panels with the hardware installed. In one embodiment, all panels are fixed against the process chamber. Modular concept/panels allow interchangeability and easy development for future customer needs or requirements. Each panel is designed with all equipment and devices accessible by the operators, while in the back all technical components are preferably installed like motors, network cables, power supply, etc. In one embodiment, the panel forms part of a backend cabinet. In one embodiment, the backend cabinet is modular.

After this first purification or filtration step, known as primary clarification, the harvest is concentrated in the bioreactor chamber. As a concentrator for instance a TFF can be used. Optionally the harvest is buffer exchanged using diafiltration.

Diafiltration is the fractionation process that washes smaller molecules through a membrane and keeps molecules of interest in the retentate. Diafiltration can be used to remove salts or exchange buffers. Accordingly, the diafiltration module can be used to exchange one buffer for another and is a more efficient substitute for dialysis. Diafiltration can be used to neutralize pH and as a concentration step (to concentrate the cell product).

In a further embodiment the system comprises a downstream chamber, flanking said bioreactor chamber. In the downstream chamber the harvest is optionally further clarified after the concentration (and buffer exchange) step in the bioreactor chamber. This step is known as secondary clarification.

In an embodiment, said downstream chamber is in fluid connection with said bioreactor chamber and/or the process chamber. In a preferred embodiment, said downstream chamber is in fluid connection with said bioreactor chamber. In a further embodiment the purification or filtration devices in the downstream chamber are first flushed to a waste tank before seeing product. After the flushing, the product in the collection vessel is sent through the devices in the downstream chamber until the collection vessel is emptied. In a further embodiment, the devices are then rinsed with a chasing buffer for a specified time. The chasing step is combined with the rinsing cycle of the collection vessel and the TFF. Buffers are located outside of the system and are introduced in the system by the left side as for the media. In some embodiments, a specific pump is scheduled to add buffers. In an embodiment, an assembly (named bioharvest feed assembly) is present for transfer of the harvest from the process chamber to the collection vessel and a waste vessel.

In another embodiment, an assembly (named diafiltration buffer assembly) is present, starting from a diafiltration buffer feed in the process chamber to the collection vessel in the bioreactor chamber and the secondary clarification system in the downstream chamber or from the collection vessel in the bioreactor chamber to the secondary clarification system in the downstream chamber. In an embodiment, this diafiltration buffer assembly is connected to a buffer feed assembly, wherein this buffer feed assembly provides buffer for the clarification filters for filter wetting/priming. In an embodiment, the buffer feed assembly comprises four inlet connections and a single-use pump head.

In another embodiment, an assembly (named permeate/waste assembly) is present connecting the TFF permeate and the waste vessel in the downstream chamber. In another embodiment, an assembly (named bulk product outlet assembly) connects the secondary clarification assembly or the diafiltration buffer assembly with the waste vessel and the transfer bag.

The current invention also provides for an innovative way of venting filters such as clarification filters. Prior to being used, these filters should be primed and vented. In a classical way, a filter is vented aseptically by the addition of a priming solution by means of a pump until the solution reaches the vent line (typically the top of the filter). During the addition of the solution, the outlet line of said filter is closed. While doing so, some of the priming solution may enter into a bottle that is connected to said filter. When the solution reaches the vent line, the pump is stopped and the vent line is closed by means of a (manual) clamp or pinch valve or the like. At this point, the filter is primed and vented (with no air inside the filter). Once the outlet line is opened again, the filter can be used. The operation as described above is a manual operation, and therefore includes a few risks. Indeed, if the operator fails to see that the priming solution has reached the vent line, the bottle connected to the vent will be rapidly filled with the priming solution and the vent of the bottle clogged. Consequently, the pressure will increase and can create an overpressure with a risk of leakages. In addition, filters are not transparent, and the operator(s) may have difficulties seeing whether or not the level inside the filter is increasing and to what extent.

To conclude, the above explained operation requires the utmost care and attention and is therefore often performed with at least two operators. In many cases, these operators will manually modulate the flow rate to carefully perform this step. The operator(s) must be ready to immediately react and stop the pump when the liquid reaches the vent line.

Automation of this step is difficult and risky, as disposable manifolds and filters are used that usually cannot resist high pressure.

The current invention aims to provide a solution for above problem, by allowing venting and priming of filters such as clarification filters in a novel and innovative way, which may limit the risks and problems as described above.

The method makes use of a line connected to the filter that moves above the filter (vertical rise tubing) and allows to reach the level inside the filter by principle of the communicating vessels. Doing so, the outlet line will be filled in parallel with the filter and reach the same levels (communicating vessels principle). The latter allows that the outlet line remains open during priming and venting and prevents the risk of overpressure. Should there still be some overpressure in the system, the priming solution will be pushed inside the outlet line.

More in detail, the method employs the following steps:

The vent line (top of the filter) is open (automated pinch valve) and connected to a sterile bottle containing a vent. An outlet line is provided to the filter, wherein a part of said outlet line rises vertical and parallel to said filter(s).

The priming solution is added to the filter by means of a pump. While the solution fills the filter(s), the vertical part of the outlet line is filled as well. Filling continues until the filters are completely filled and the solution reaches the vent line of said filters. Reaching the vent line is detected by a liquid sensor, such as a bubble sensor. Said liquid sensor is preferably present in the vertical part of said outlet line.

Once the vent line has been reached, the vent line is closed (automated pinch valve). At this step, the filter is primed and vented (no air inside anymore) and the filter can be used.

Optionally, a (digital) pressure sensor can be present, to be used to stop the system in case of an emergency or technical issue.

By the method as described above, the filter is immediately usable once the vent line is closed. The manual operations are hereby limited to the absolute minimum and the risks that something goes wrong during priming/venting are minimized.

In an embodiment, a method for venting and priming a filter such as a clarification filter is disclosed herein, wherein said filter is in liquid connection with an outlet line, said outlet line comprises a section that is positioned parallel to said filter and rises in a vertical direction, allowing for a vertical flow in said outlet line, wherein a priming solution is added to said filter by means of a pump, and wherein said priming solution fills said filter and said vertical section of said outlet line during priming. Said filling continues until the solution reaches a vent line of said filter, after which said vent line is closed, preferably automatically closed.

Said method as disclosed herein can be used in a system as described herein. To that purpose, filters, such as clarification filters may be provided with an outlet line which comprises a vertical section positioned parallel to said filter and which is in liquid connection with said filter. An automated pinch is present, suited to open and close the vent line (top op said filter). A digital liquid detector such as a bubble sensor can be positioned in the vent line to prevent leakage or to stop the system in case of an emergency.

In an embodiment actively producing biomolecules, said system is paired with a bioreactor cabinet.

In a preferred embodiment the bioreactor cabinet is located at the middle of the system. This location allows a better operator access and footprint reduction. The pairing of an independent bioreactor cabinet which can be removed from the system, allows better access to all other elements of the process as the operator can go inside the system when the bioreactor cabinet is removed. Similar, during manifold installation, the bioreactor cabinet can be removed from the system and the bioreactor and vessel can be installed, after which the bioreactor cabinet can be reconnected to the system, improving ergonomic constraints.

In an embodiment, one or more of the following elements: a part of the fluid path, cell culture media, buffers, waste container or the drug substance container, are located outside the bioreactor cabinet and are connected with standard sterile connectors.

In a preferred embodiment the system is mobile. To that purpose, the chambers may be comprised of wheels or any other element that allows movement. Wheels will allow the system to be mobile and to be transported.

In an embodiment the system is designed to be installed in a GMP manufacturing area. However, for cleaning purposes, the system can be easily transported to a different location. In an embodiment the system is designed to be resistant to standard VHP decontamination cycle or similar. In an embodiment the system is only suitable for indoor environments and the room temperature should be maintained at ambient temperature.

In a preferred embodiment of the invention, the system comprises a HVAC system that extracts air from the system's surrounding, filters said air, preferably by means of a HEPA filter and provides filtered air in said system chambers.

The HVAC system allows for the supply of air with the appropriate quality level to the system chambers, offering an additional protection to the product. In a preferred embodiment, the ventilation ensures to reach environmental grade ISO 7 (defined in the ISO 14644) with C grade in the system chambers.

In a preferred embodiment, air is extracted from the surrounding grade C or D area, filtrated in HEPA (H14) and blow into the system chambers. The air is evacuated out of the system chambers by the window gap at the work plan level. Preferably, the airflow (downflow) inside the system chambers (in the work area) has a velocity of 0.45 m/s at 15 cm from the work plan and the back sheet. In a preferred embodiment, the HVAC system comprises 3 blocks attached to each other. Each block contains one filter HEPA (H14) with a fan, allowing each HEPA filter to be integrity tested individually and easily replaced by one engineer and the fan to be easily replaced by one operator and to be accessible for maintenance operations. A 100% DOP central connections is foreseen in the technical area to ease the integrity testing. In an embodiment each HEPA filter can be monitored by a magnetic indicator. In an embodiment, membrane diffusion screens are located above one or more of the system chambers generating a uniform airflow inside the chamber(s). In an embodiment, the membrane diffusion screens comprise a stainless-steel frame and a stainless-steel mesh.

In some embodiments, the HVAC system is placed on top of said chambers. In a preferred embodiment, the design of the system is articulated around a central column, containing the HVAC system at the upper end of the column. In a preferred embodiment, the airflow is unidirectional and guided between the back plate of the technical enclosure and the glazing. The glazing can be made of any material suited in the art, such as Plexiglas, glass or polycarbonate (PC).

In some embodiments, the back of each chamber in the system is provided with an electrical cabinet, said electrical cabinet houses the electrical parts of the instruments present in said chamber.

Electrical cabinets supplying the power to instruments and controlling the process are integrated at the back side of the system. In a preferred embodiment, these electrical cabinets are composed by a back sheet, a technical enclosure and a space for a circuitboard. In some embodiments, the electrical cabinets are made of stainless steel and are accessible by opening the back doors of the system. The back sheet is fixed to the front of the electrical cabinet to allow proper instrument and electronic part fixation. In some embodiments, key components to be accessible by maintenance during operations are located in the front part of the chamber, while all terminals boxes, wiring and electronics are in the back with no access during the operation. In a preferred embodiment, the electrical cabinets are removable, replaceable, exchangeable and/or interchangeable. In an embodiment, the electrical cabinets are modular. In an embodiment, the system comprises at least one electrical cabinet. In a further embodiment, the system comprises a plurality of electrical cabinets. In a preferred embodiment, the system comprises 9 electrical cabinets. In a further embodiment, each of the chambers in the system (bioreactor chamber, process chamber and downstream chamber) comprises 3 electrical cabinets each.

In a further aspect, the current disclosure also comprises the use of a system as described above for biomolecule production, such as proteins, viruses or viral particles, or gene therapy products.

In a preferred embodiment, the fluid path within the system is a fully closed system made of disposable consumables (e.g. bioreactor, filters, TFF membranes, bottles, sampling devices, single used sensors) interconnected by disposable tubing manifolds. In an embodiment, the fluid path includes sampling systems. In an embodiment, the foam trap is connected with the collection vessel. In an embodiment, the bioreactor is developed for single-use and comprises disposable pre-fitted manifolds for a top and bottom liquid bioreactor drain, a liquid sample line, a bubble or foam trap and a base addition.

In a final aspect, the disclosure also pertains to a chained method for producing a biomolecule, such as a protein, a virus or viral particle, or gene therapy product by means of a system according to any of the embodiments as described above. Said method may comprise the steps of providing a bioreactor provided in a bioreactor cabinet, preferably a wheeled bioreactor cabinet, that docks into a bioreactor chamber of a biomolecule production system, and wherein a harvest from said bioreactor is filtered or purified in a processing chamber flanking said bioreactor chamber to produce a biomolecule harvest, said biomolecule harvest is further concentrated by means of a concentrator located in said bioreactor chamber.

In some embodiments, said biomolecule harvest is inline clarified in one or more filters present in said downstream chamber flanking said bioreactor chamber.

A possible process flow in an embodiment of the system involves the production of a biomolecule, such as a viral particle, e.g. for producing a vaccine or a viral gene therapy product. To this purpose cells are cultured in the bioreactor inside the bioreactor cabinet which is embedded in the bioreactor chamber. Media and buffer are supplied to the bioreactor by means of externally supplied bags, that are connected to the bioreactor chamber. Waste that is produced during the production cycle is guided towards a waste vessel. Subsequently the bioreactor harvest is lysed and transported to the process chamber, where it is filtered using purification or filtration devices. After this step, the product is either harvested or transported to the bioreactor chamber, where it is concentrated by means of the collection vessel and TFF. Afterwards, the concentrate is transported towards the purification or filtration devices in the downstream chamber. Additional chambers can be connected to said system in case further upstream or downstream processing is needed.

In a particular embodiment, the current disclosure provides for a system and method for the production of a (therapeutic) gene therapy product, more preferably a human gene therapy product, even more preferably a viral gene therapy product that uses a viral vector to introduce genetic material in a subject.

In an embodiment, said viral vector may be a retrovirus, adenovirus, herpes simplex, vaccinia, lentivirus or an adeno-associated virus.

During the infection phase, the virus is added to the bioreactor. In an embodiment, the virus is added to the bioreactor by means of a virus infection kit. In an embodiment, the virus infection kit comprises a two-part bottle assembly for the virus infection process and two spare connections. In an embodiment, the virus is added to the bioreactor by means of a pump, such as a Watson-Marlow peristaltic pump.

In an embodiment, an endonuclease is added to the bioreactor for nucleic acid removal. In an embodiment, an endonuclease is added to the bioreactor via an inlet for small additions. Endonucleases are the ideal tool for nucleic acid removal in virus vector and vaccine manufacturing. In a further embodiment, the endonuclease is added by means of an endonuclease assembly comprising a 5 L single-use bottle assembly and extra connections. In an embodiment, the endonuclease is added to the bioreactor by means of a pump, such as a Watson-Marlow peristaltic pump. In an embodiment, the endonuclease is benzonase endonuclease, which degrades both DNA and RNA to small 3-5 base pairs (<6 kDa) fragments with no base preference. The use of benzonase endonuclease additionally increases the yield in virus purification, protects the downstream chromatography and filter devices from fouling and reduces feed stream viscosity.

In an embodiment, transfection reagent is added to the bioreactor by means of a transfection assembly comprising a single-use bag assembly and two extra connections.

In another embodiment, said biomolecule that is produced is a vaccine, such as a vaccine against influenza, SARS, MERS, COVID-19, Measles, Rabies, Zika, Polio, Mumps or Rubella.

The present invention will be now described in more details, referring to figures that are not limitative.

DESCRIPTION OF FIGURES

The present invention is in no way limited to the embodiments described and/or shown in the figures. On the contrary, methods according to the present invention may be realized in many different ways without departing from the scope of the invention.

Reference is made to FIG. 1A which illustrates one embodiment of a bioreactor cabinet 001. Arrows indicate the positions where the bioreactor 100,200,300, the heating support (not shown) and agitation motor (not shown) can be installed on the bioreactor cabinet 001. The bioreactor 100,200,300 is installed in the bioreactor docking station 044. In addition, wheels 005 as moving structure are visible on FIG. 1A. Two handles 004, 004' allow easy manipulation of the bioreactor cabinet 001. The removable height adjuster 006 is able to accommodate a bioreactor of 200 m² 100, 200,300.

FIG. 1B illustrates another embodiment of a bioreactor cabinet 001. One handle 004 connected to the front wall of the bioreactor cabinet 001 allows easy manipulation of the bioreactor cabinet 001, especially when docking said bioreactor cabinet. The bioreactor cabinet is provided by wheels 005 (or other features for providing mobility) in order to allow easy transport. A bioreactor 100,200,300 a heating support (not shown) for heating the culture media of said bioreactor and agitation motor (not shown) are installed in the bioreactor cabinet 001. A removable height adjuster 006 in the form of a disc-like structure makes it possible to accommodate a bioreactor of 200 m² 100,200,300 while ensuring that the top surface of the bioreactor 114 levels with the top surface of the bioreactor cabinet 008. In case a larger bioreactor 100,200,300 is used (e.g. a 600 m² surface bioreactor) the use of the height adjuster 006 may become obsolete. A connecting portion of a connector 009 and a magnetic connection 010 are provided on a wall of the bioreactor cabinet 001, opposite to the front wall 011 of said bioreactor cabinet. While the connecting portion of a connector 009 and the magnetic connection 010 are not necessarily to be positioned on the same wall of the bioreactor cabinet 001 as shown in FIG. 1B, the latter does enhance the ergonomics and the ease of handling of said bioreactor cabinet 001. Both the connecting portion of the connector 009 and the magnetic connection 010 are designed to be able to engage with their counterparts present on a biomolecule production system. In the embodiment shown in FIG. 1B, each sidewall 012 of the bioreactor cabinet 001 is provided with positioning means at the corners of these sidewalls, which are in essence a pair of wheels 013. Each pair of wheels comprises two wheels, wherein the first wheel is positioned perpendicular to the direction of the second wheel. The bioreactor cabinet comprises a grid-like bioreactor support plate 014 on the top surface of the bioreactor cabinet 008, comprising of a recess 015 to allow the protrusion of a bioreactor surface 114. Said bioreactor cabinet

001 may internally be divided in shelfs 016, allowing stockage of material and hardware. The bioreactor cabinet of this embodiment contains two retention trays 037. The different retention trays 037 on the bioreactor cabinet are on different levels and are connected to each other with a tube 038.

FIG. 1C illustrates a further detailed embodiment of FIG. 1B. One handle 004 connected to the front wall 011 of the bioreactor cabinet 001 allows easy manipulation of the bioreactor cabinet 001, especially when docking said bioreactor cabinet 001. The bioreactor cabinet 001 is provided by wheels/casters 005 in order to allow easy transport. Alternatively, other features may be used for providing mobility of the cabinet 001. A bioreactor 100,200,300 a heating support (not shown) for heating the culture media of said bioreactor and agitation motor (not shown) are installed in the bioreactor cabinet. A removable height adjuster 006 in the form of a disc-like structure makes it possible to accommodate a bioreactor of 200 m$^2$ while ensuring that the top surface of the bioreactor 114 levels with the top surface of the bioreactor cabinet 008. A connecting portion of a connector 009 and a magnetic connection 010 are provided on a wall of the bioreactor cabinet, opposite to the front wall 011 of said bioreactor cabinet. In the embodiment shown in FIG. 1C, each sidewall 012 of the bioreactor cabinet 001 is provided with positioning means at the corners of these sidewalls, which are in essence a pair of wheels 013. Each pair of wheels comprises two wheels, wherein the first wheel is positioned perpendicular to the direction of the second wheel. The bioreactor cabinet comprises a grid-like bioreactor support plate 014 on the top surface of the bioreactor cabinet, comprising of a recess 015 to allow the protrusion of a bioreactor surface 114. Said bioreactor cabinet 001 may internally be divided in shelfs 016, allowing stockage of material and hardware. The bioreactor includes an external casing or housing 112 forming an interior compartment and a removable cover or top surface 114 for covering the interior compartment, which may include various openings or ports P with removable covers or caps C for allowing for the selective introduction or removal of fluid, gas (including by way of a sparger), probes, sensors, samplers, or the like.

FIGS. 1D-1F illustrate a cross section of an embodiment according to the current disclosure. One handle 004 connected to the front wall 011 of the bioreactor cabinet 001 allows easy manipulation of the bioreactor cabinet 001, especially when docking said bioreactor cabinet 001. The bioreactor cabinet 001 is provided by wheels 005 or other features for mobility in order to allow easy transport.

In FIGS. 1E-1F a bioreactor 100,200,300 a heating support (not shown) for heating the culture media of said bioreactor and agitation motor (not shown) are installed in the bioreactor cabinet 001. A removable height adjuster 006 in the form of a disc-like structure makes it possible to accommodate a bioreactor of 200 m$^2$ while ensuring that the top surface of the bioreactor 114 levels with the top surface of the bioreactor cabinet 008. The bioreactor cabinet 001 comprises a grid-like bioreactor support plate 014 on the top surface of the bioreactor cabinet, comprising of a recess 015 to allow the protrusion of a bioreactor surface 114. Said bioreactor cabinet 001 may internally be divided in shelfs 016, allowing stockage of material and hardware. The bioreactor includes an external casing or housing 112 forming an interior compartment and a removable cover or top surface 114 for covering the interior compartment, which may include various openings or ports P for allowing for the selective introduction or removal of fluid, gas (including by way of a sparger), probes, sensors, samplers, or the like.

FIG. 2 illustrates a front view of a biomolecule system 017 according to an embodiment of the disclosure showing a process chamber 018, a downstream chamber 019 and a bioreactor chamber 020, suited to receive a bioreactor 100, 200,300 in a bioreactor cabinet 001. To that purpose the system 017 is provided with a recess 021 that allows receiving a bioreactor cabinet 001 in said system 017. The bioreactor chamber 020 is mandatory; the process chamber 018 and downstream chamber 019 are optionally and can be coupled separately to the bioreactor chamber 020. The bioreactor 100,200,300 includes an external casing or housing 112 (not shown) forming an interior compartment and a removable cover or top surface 114 for covering the interior compartment. The user handling area of each chamber in the system is shielded with a front window 022, said front window is preferably provided with a gap 023 to allow access during operation.

FIG. 3 shows a top view of a system 017 according to an embodiment of the current disclosure comprising a process chamber 018, a downstream chamber 019 and a bioreactor chamber 020. The bioreactor cabinet 001 of the system 017 when fitted in said system protrudes from the processing chamber 018 plane, allowing the operator easier access to the bioreactor cabinet 001. The back of each chamber in the system is provided with an electrical cabinet 024. These electrical cabinets supply the power to instruments and control the process and are composed by a back sheet 025, a technical enclosure 028 and a space for a circuitboard 029. In this embodiment, the electrical cabinets are made of stainless steel and are accessible by opening the back doors of the system. The back sheet 025 is fixed to the front of the electrical cabinet 024 to allow proper instrument fixation and electronic part dissimulation. Key components to be accessible by maintenance during operations are located in the front part of the chamber, while all terminals boxes, wiring and electronics are in the back with no access during the operation.

FIG. 4A shows a front view of a system 017 according to an embodiment of the current disclosure. The system comprises a process chamber 018 comprising one or more purification or filtration devices allowing the purification or filtration of a biomolecule of a cell harvest, a downstream chamber 019 and a bioreactor chamber 020. The bioreactor chamber is suited to receive a bioreactor 100,200 in a bioreactor cabinet 001. The bioreactor cabinet 001 is guided into the bioreactor chamber by the use of guides 036 on the bioreactor chamber 020 and wheels 013 on the bioreactor cabinet 001. The general casing 026 is the main structure of the system. In some embodiments, the length of the system 017 can be reduced depending on the number of filters in the process chamber 018 and the downstream chamber 019. Materials used for the general casing 026 of said system are resistant to corrosion. In the embodiment shown in FIG. 4A, the metallic elements are made of stainless steel SS316 with a rugosity of Ra≤1.2 μm.

FIG. 4B shows a back view and a front view of the system 017 shown in FIG. 4A. A HVAC system 027 is placed on top of the chambers 018,019,020 ensuring that air with the appropriate quality level is supplied to the system chambers. The backside and sides of the casing of said system is comprised of electrical 024 and pneumatic cabinets 030, comprising the important electrical and pneumatic components of said system. This allows easy access to these electrical and pneumatic components by the operator, meanwhile ensuring that the operator does not have to enter the spaces wherein the biomolecules are produced.

FIG. 5 illustrates a detail of the front view of a system according to an embodiment of the current disclosure including the front windows 022. In a preferred embodiment the general casing of the system has front windows with a gap 023 of 200 mm with the work plan 031. This gap allows the evacuation of the air from the process chamber 018 and gives access during operations. The overall design allows the operators to stay in front of the chamber. In an embodiment the windows can be opened by two different ways (vertically and horizontally).

FIG. 6A illustrates a preferred embodiment of a system 017 according to the current invention. In this embodiment, a bioreactor chamber 020 is positioned centrally in the production system 017 which is flanked by a process chamber 018 and a downstream chamber 019. This bioreactor chamber 020 allows docking of the bioreactor cabinet 001 comprising a bioreactor 100,200,300. To that purpose, the bioreactor chamber 020 is provided with a recess (not shown) that allows receiving said bioreactor cabinet 001. To facilitate docking of the bioreactor cabinet a handle 004 is present on the bioreactor cabinet 001. The bioreactor cabinet 001 contains wheels 005 to allow easy transportation. The bioreactor 100,200,300 includes an external casing or housing (not shown) forming an interior compartment and a removable cover or top surface 114 for covering the interior compartment, which may include various openings or ports P with removable covers or caps C for allowing for the selective introduction or removal of fluid, gas (including by way of a sparger), probes, sensors, samplers, or the like.

Bioreactor harvest from the bioreactor ports will be transported to the process chamber 018, the appropriate pipings 039 are provided to allow fluid transfer. The process chamber 018 is provided with a one or more purification or filtration devices 032 allowing the purification or filtration of a biomolecule of a cell harvest. The purification or filtration devices 032 are provided with an outlet line having a vertical section 502 parallel to said purification or filtration devices 032, and which allows for safe priming and venting of said purification or filtration devices 032 prior to use. Priming solution is providing via an inlet line 503 in connection to said purification or filtration devices 032. Such filter may for instance be an in-depth filtration system. The number of filters in the process chamber 018 is flexible, depending on the product that is to be produced. As the filters are located on the side of the system, the design is quite flexible if a huge number of filters must be added. The working space 031 is located at around 90 cm from the ground to allow the operators to perform procedures standing up.

The background metal sheet 025 in the process chamber 018 is designed with all equipment's and devices accessible by the operators, while in the back 028 all technical components are installed like motors, network cables, power supply, etc.

The bioreactor chamber 020 is equipped with a collection vessel 033 and a TFF 034 in order to concentrate the harvest. The collection vessel 033 and TFF 034 are fluidly connected to each other. Both are located at the centre of the bioreactor chamber 020 behind the bioreactor 100, 200. The collection vessel 033—TFF 034—and TFF pump (not shown) assembly is attached to the background metal sheet 025 of the system 017. Access to collection vessel 033 and TFF 034 is possible when the bioreactor cabinet 001 is not docked into said system 017. The homogeneity inside the collection vessel is guaranteed with the recirculation loop through the TFF 034 with the TFF pump (not shown). From the TFF 034, concentrated biomolecule harvest can be transferred to a downstream chamber 019 of said system. Again, the appropriate pipings 039 are provided to allow fluid transfer. Said downstream chamber 019, flanks said bioreactor chamber 020 on the side opposite from the process chamber 018. The presence of a downstream chamber 019 is optional. In the downstream chamber 019 the harvest can be further clarified after the concentration step in the bioreactor chamber 020. Said downstream chamber 019 is in fluid connection with the bioreactor chamber 020 and comprises one or more purification or filtration devices 032 allowing the purification or filtration of a biomolecule of a cell harvest. The back sheet 025 of the downstream chamber is provided with pumps, pipings, electrical sockets and/or manifolds needed for allowing functioning of said chamber. In the back of the technical enclosure 028 all technical component must be installed like motors, network cables, power supply, etc.

FIG. 6B shows the embodiment of FIG. 6A from a different perspective.

Reference is now made to FIG. 7, which illustrate one embodiment of a bioreactor 100 for culturing cells, according to one aspect of the disclosure. In some embodiments, the bioreactor 100 includes an external casing or housing 112 forming an interior compartment and a removable cover 114 for covering the interior compartment, which may include various openings or ports P with removable covers or caps C for allowing for the selective introduction or removal of fluid, gas (including by way of a sparger), probes, sensors, samplers, or the like.

Within the interior compartment formed by the bioreactor housing 112, several compartments or chambers may be provided for transmitting a flow of fluid or gas throughout the bioreactor 100. As indicated in FIG. 8, in some embodiments, the chambers may include a first chamber 116 at or near a base of the bioreactor 100.

In some embodiments, the first chamber 116 may include an agitator for causing fluid flow within the bioreactor 100. In some embodiment, the agitator may be in the form of a "drop-in" rotatable, non-contact magnetic impeller 118 (which as outlined further below may be captured or contained within a container (not shown) including a plurality of openings for admitting and releasing fluid).

In some embodiments, as a result of the agitation provided, fluid may then flow upwardly (as indicated by arrows A in FIG. 8) into an annular chamber 120 along the outer or peripheral portion of the bioreactor 100. In some embodiments, the bioreactor is adapted to receive a fixed bed, such as a structured spiral bed 122, which in use may contain and retain cells being grown. As indicated in FIG. 8, in some embodiments, the spiral bed 122 may be in the form of a cartridge that may be dropped or placed into the chamber 120 at the point of use. In some embodiments, the spiral bed 122 can be pre-installed in the chamber during manufacture at a facility prior to shipping.

In some embodiments, fluid exiting the chamber 120 is passed to a chamber 124 on one (upper) side of the bed 122, where the fluid is exposed to a gas (such as oxygen or nitrogen). In some embodiments, fluid may then flow radially inwardly to a central return chamber 126. In some embodiments, the central return chamber can be columnar in nature and may be formed by an imperforate conduit or tube 128 or rather formed by the central opening of the structured spiral bed. In some embodiments, the chamber 126 returns the fluid to the first chamber 116 (return arrow R) for recirculation through the bioreactor 100, such that a continuous loop results ("bottom to top" in this version). In some embodiments, a sensor, for example a temperature probe or sensor T may also be provided for sensing the temperature of the fluid in the chamber 126. In some embodiments, additional sensors (such as, for example, pH, oxygen, dissolved oxygen, temperature) may also be provided at a location before the fluid enters (or re-enters) the chamber 116. The sensors and probes as described herein, may be reusable, one-time-use and/or disposable.

FIG. 9A shows one embodiment of a matrix material for use as a structured fixed bed in the bioreactor of the present disclosure and, in particular, a spiral bed 122. In some embodiments, one or more cell immobilization layers 122*a* are provided adjacent to one or more spacer layers 122*b* made from a mesh structure. In some embodiments, the layering may optionally be repeated several times to achieve a stacked or layered configuration. In some embodiments, the mesh structure included in spacer layers 122*b* forms a tortuous path for cells (see cells L in FIG. 9B suspended or entrapped in the material of the immobilization layer 122*a*), and a cell culture may form part of any invention claimed herein) and fluid to flow when layered between two immobilization layers 122*a*. Homogeneity of the cells is maintained within the structured fixed bed as a result of this type of arrangement. In some embodiments, other spacer structures can be used which form such tortuous paths. In some embodiments, as shown in FIG. 9A, the structured fixed bed can be subsequently spirally or concentrically rolled along an axis or core (e.g., conduit 128, which may be provided in multiple component parts). In some embodiments, the layers of the structured fixed bed are firmly wound. In some embodiments, the diameter of the core, the length and/or amount of the layers will ultimately define the size of the assembly or matrix. In some embodiments, thickness of each of the layers 122*a*, 122*b* may be between 0.1 and 5 mm, 01 and 10 mm, or 0.001 and 15 mm.

According to one aspect of this disclosure, the bioreactor 100 in certain embodiments may be "modular." In some embodiments, a modular bioreactor can be comprised of a plurality of discrete modules that interact together to create a space suitable for culturing cells in a manner that is highly predictive due to the manufacturing homogeneity of the modules. In some embodiments, a modular bioreactor is not limited to particular shape or form (e.g., cylindrical or otherwise, and with a structured fixed bed or unstructured bed, depending on the application). For example, as shown in FIG. 10. In some embodiments, the modules may comprise a base portion formed by base module 130, an intermediate portion formed by an intermediate module 140 (which may be formed from a number of stackable modular portions, as outlined further in the description that follows), an optional associated central module, such as conduit or tube 128, which may also be considered part of the intermediate module, and a cover module, such as formed by a cover part in the form of lid or removable cover 114. In some embodiments, the modules may be separately manufactured as individual components and either assembled at a manufacturing facility based on an intended application (and then shipped to a point of use) or assembled based on an intended application at the point of end use. In some embodiments, the modules of the bioreactor 100 interact to create a place for growing cells, such as in a high-density manner using a fixed bed, such as for example a structured or unstructured fixed bed.

A further embodiment of a bioreactor 200 according to the disclosure is shown in FIGS. 11-14. In some embodiments, the bioreactor (whether modular or otherwise pre-assembled as a single unit) can comprise a base, an intermediate portion and a cover. In some embodiments, a base portion can comprise base part 230. In some embodiments, an intermediate portion can comprise intermediate parts 250 and/or

270. In some embodiments, intermediate parts 250 and 270 are not identical. In some embodiments, a cover portion can comprise a cover part 280. Referring to FIG. 11, in some embodiments, base part 230 may include an external wall 232 and an internal wall 234, which may define a first chamber 216 for receiving the agitator (not shown). In some embodiments, the internal wall 234 can include openings 234*a* for allowing fluid flow to the second, radially outward chamber 220 bounded by the external or outer wall 232 (FIG. 12).

As can be seen in FIG. 12, in some embodiments, the internal wall 234 may include a plurality of connectors, such as grooves 236, for engaging corresponding connectors, such as tongues 250*a*, on the first intermediate part 250, as shown in FIG. 13. In some embodiments, the internal wall 234 may be of lower/higher height than the external wall 232. In some embodiments, the internal wall 234 may be of lower height than the external wall 232, as can be seen in FIG. 8. With reference to FIG. 11, in some embodiments, the first intermediate part 250 may be at least partially recessed within the base part 230.

In some embodiments, the base part 230 may include a peripheral connector, such as a groove 237 (FIG. 11). In some embodiments, the connector or groove 237 can be adapted to receive a corresponding connector of a second intermediate part 270, which may simply be part of an outer wall 262 thereof. In some embodiments, within the intermediate part 270 can be located a plurality of fixed beds 274 in a third chamber 224 (but a single monolithic fixed bed could be used, which in this or any disclosed embodiment may take any size, shape, or form), which could be supported by an interposed support, but a gap G could also be provided between adjacent sections of fixed beds). The gap could also be eliminated, such that an upper bed rests on and is supported by a lower one.

In some embodiments, the structured fixed bed can be of the spiral form, as shown in FIGS. 9, 9A, 9B, and 9C (which spiral form can be implemented in any embodiment of a bioreactor, disclosed or otherwise). In the case of a spiral bed, the bed may be wound around an internal wall 266, which may form a fifth chamber 228 for returning fluid to the first chamber 216 in the base part 230. The internal wall 266 may comprise multiple stacked tubular parts, as shown. In some embodiments, the multiple stacked tubular parts can allow for the height to be adjusted depending on the number of fixed beds present (e.g., one tubular part may be provided for each stacked bed) (FIG. 11).

In some embodiments, the cover part 280, or lid can be adapted to removably connect with the second intermediate part 270, and thus form a fourth chamber 226 in which the liquid encounters gas, for example air. In some embodiments, the connection between the cover part and the second intermediate can be by a connector, such as a groove 282, which receives the upper end of the outer wall 262 or any access mechanism disclosed herein. The lid or cover part 280 may include various ports P (FIG. 11).

Turning back to FIGS. 11 and 14, further details of the intermediate part 250 are shown. In some embodiments, part 250 may include a plurality of radially extending supports 254, which thus lend support for a structured fixed bed when resting thereon in the adjacent third chamber 224. In some embodiments, the height H of the supports 254 can be sufficient to allow the fluid to develop sufficient upward velocity before entering the chamber 224 to pass through the full section of the fixed bed 274 (FIG. 11).

In some embodiments, an inner annular wall 258 can be connected to the inboard end of the supports 254. In some embodiments, the wall 258, corresponds in diameter to the diameter of the internal wall 266 of the intermediate part 270, which may also connect with it (such as by nesting). In some embodiments, the internal wall 266 can form a passage for delivering fluid from the fifth chamber 228 to the first chamber 216. In some embodiments, a flow disruptor 260 may be provided in this passage to help prevent the creation of any vortex within the fifth chamber 228.

From FIG. 11, in some embodiments, it can be understood that the flow from one fixed bed module to the next-adjacent fixed bed module in the cell culturing chamber 224 can be direct or uninterrupted. In some embodiments, the outer chamber 224 can create a continuous flow path through the multiple beds located therein, which may be structured fixed beds, unstructured fixed beds, or unstructured beds. In some embodiments, the continuous and substantially unimpeded flow through the predesigned and matching bed modules helps to promote homogeneity for cell growth and other processing and enhances the consistency of the cell culturing operation, and also promotes the ability to take measurements or samples from the stacked beds, which is not readily possible if blocking partitions (as contrasted with the perforated supports, as discussed below) are present. Finally, in a structured bed embodiment, the manufacture of the overall bioreactor is even less complicated and labor intensive as the effort to match the properties and characteristics from one fixed bed module to the other is greatly reduced.

Reference is now made to FIGS. 15 and 16, which schematically illustrate a third embodiment of a bioreactor 300, which for purposes of clarity is shown in cross-section. In some embodiments, the bioreactor 300 (whether modular or otherwise pre-assembled as a single unit) comprises an external housing 331 with a cover 333, either of which may include various openings or ports for allowing for fluid introduction or removal. In some embodiments, within the bioreactor housing 331, several compartments or chambers are provided, including a first chamber 316 including an agitator for causing fluid flow within the bioreactor 300, which may be in the form of a "drop-in" rotatable, non-contact magnetic impeller 318 or an agitator disclosed herein. As indicated in FIG. 15A, in some embodiments, the impeller 318 may be housed, captured or contained within a housing, such as a housing or container 318a including a plurality of openings 318b serving as inlets and outlets for admitting and releasing fluid (but any other form of agitator could be used). In some embodiments, the agitation created may be such that fluid is caused to flow into a second or outboard annular chamber 320, which is radially outward of the first chamber 316.

In some embodiments, fluid may then flow upwardly (as indicated by arrows in FIG. 16) into a third annular chamber 324 along an intermediate, outer portion of the bioreactor 300. In some embodiments, the outer portion can be adapted to receive a fixed bed, such as a structured spiral bed 325, but other forms may be used), which in use may contain cells being grown. In some embodiments, the spiral bed 325 may be in the form of a cartridge that may simply be dropped into the chamber 324 at the point of use, or could be pre-installed in the chamber during manufacture at a facility prior to shipping.

In some embodiments, fluid exiting the third chamber 324 can then passed to a fourth chamber 326, where it is exposed to a gas (such as air) and then flows radially inwardly to a fifth chamber 328, which is columnar in nature and returns the fluid to the first chamber 316 for recirculation through the bioreactor 310, such that a continuous loop results. In some embodiments, a temperature probe or sensor T, or any other sensor disclosed herein may also be provided for sensing a parameter, for example the temperature of the fluid directly in the fifth chamber, and additional sensors (such as, for example, pH or dissolved oxygen) may also be provided at this location (which is before the fluid enters (or re-enters) the fixed bed 325).

From the partially cutaway image at FIG. 15B, it can be understood that the third chamber 324 may be bounded by upper and lower plates 330, 332, which include openings or perforations for allowing fluid generally free of cells to enter and exit the fixed bed 325. In some embodiments, the lower plate 332 may include a central opening 332a for allowing fluid to pass from the fifth chamber 328 to the first chamber 316 for recirculation. In some embodiments, the upper plate 330 can include an opening 330a, into which fluid may travel to enter the fifth or return chamber 328.

In some embodiments, support for the upper plate 330 may be provided by a hollow, generally cylindrical tube 334, but could take other shapes. In some embodiments, the opposed ends of this tube 334 may fit into corresponding grooves 330b, 332b in the plates 330, 332 (in some cases the lower plate 332 can be integral with the impeller housing or container 318a in the illustrated embodiment). In some embodiments, supports, such as generally vertical rods 336, can be arranged to provide added support for the plate 330. In some embodiments, the disclosed vertical rods 336 do not interfere in any significant way with the fluid flow in the corresponding chamber 328. In some embodiments, the ends of the rods 336 may be recessed in the plates 330, 332, or held in place by suitable fasteners or locking mechanisms (e.g., locking connections, bolts or adhesives).

From FIG. 16 and the action arrows provided thereon, it can be understood that, as a result of the fluid agitation, in some embodiments, fluid may flow from the chamber 316 outwardly into chamber 320. In some embodiments, the fluid can then be redirected to pass vertically through chamber 324 including the fixed bed, and into chamber 328. In some embodiments, fluid is then directed inwardly to chamber 328, where the fluid may return to the first chamber 316 via opening 332a. In some embodiments, fluid can refer to culture medium.

FIG. 17 further illustrates an arrangement in which, in some embodiments, the upper plate 330 is provided with peripheral openings 330c to allow fluid to flow directly along the inner wall formed by tube 334. In this manner, a thin layer or film of fluid may be created, which flows downwardly while passing through the fifth chamber 328. In some embodiments, this may serve to increase the volume of the fluid exposed to gas (air) within the fifth chamber 328, prior to it being returned to the first chamber 316. In some embodiments, this implementation can allow for more oxygen transfer which may be needed for larger sizes or otherwise to increase cell growth rates adjust process parameters based on the biologic being produced. In some embodiments, the "waterfall" implementation that creates a fluid film can be achieved by adding a limited quantity of cell culture medium from the start, such that only a small overflow results. Alternatively, in some embodiments, the "waterfall" implementation is achieved by adding cell culture medium and cells and then when cells are growing in the bed, withdraw culture medium (such as using a dip tube) in the corresponding chamber, such as chamber 328.

FIG. 18 illustrates a possible process flow in an embodiment of the system 017. Said process involves the production of a biomolecule, such as a viral particle, e.g. for producing a vaccine or a viral gene therapy product. To this purpose cells are cultured in the bioreactor 100,200,300 inside the bioreactor cabinet 001 which is embedded in the bioreactor chamber 020. Media 040 and buffer 041 are supplied to the bioreactor by means of externally supplied bags, that are connected to the bioreactor chamber. Waste that is produced during the production cycle is guided towards a waste vessel 042. Subsequently the bioreactor harvest is lysed and transported to the process chamber 018, where it is filtered using purification or filtration devices 032. After this step, the product is either harvested or transported to the bioreactor chamber 020, where it is concentrated by means of the collection vessel 033 and TFF 034. Afterwards, the concentrate is transported towards the purification or filtration devices 032 in the downstream chamber 019. Additional chambers 043 can be connected to said system in case further upstream or downstream processing is needed.

It will be apparent to the skilled person that the process flow as shown in FIG. 18 is exemplary and that other sequences of process flows may be used in relation to the currently disclosed invention.

FIG. 19 illustrates a possible embodiment of a level sensor according to the current disclosure. Such a level sensor enables to continuously measure the liquid level in the collection vessel from outside.

FIG. 20 illustrates a possible embodiment of a pressure sensor according to the current disclosure. Such pressure sensors protect the system from overpressure.

FIG. 21 illustrates two possible embodiments of a flowmeter according to the current disclosure. Such flow meters allow non-invasive fluid monitoring from the outside through the tubing.

FIG. 22 illustrates a possible embodiment of a bubble trap according to the current disclosure. Such bubble traps remove bubbles from aqueous solutions.

FIG. 23 illustrates a possible embodiment of a container 140. One skilled in the art will appreciate that the walls of such container 140 may be formed independent of the rest of the bioreactor or may be shared with other walls or parts of the bioreactor. For instance, in FIG. 23, the bottom of such container is formed by the bottom of the bioreactor. To allow for liquid flow, the container 140 may include a plurality of openings 141, one or more of which may serve as either inlets or outlets for admitting and releasing liquid (note exemplary action arrows I (IN) and O (OUT) in FIG. 23). In some embodiments, liquid exiting the container 140 may then flow upwardly and through the structured bed, such as spiral bed, and return to an inlet via openings 141 of the container 140. One skilled in the art will appreciate that the arrangement could also operate in reverse. In order to ensure stability and proper injection location of bubbles, a tube 142 can be connected along a sidewall of the container 140.

It may be desirable to increase the amount of gas transfer to the cell culture media liquid while circulating through the bioreactor. According to one aspect of the disclosure, and with reference to FIG. 24, this may be achieved by introducing a flow of gas, such as air or oxygen, into the bioreactor. Specifically, an injector for injecting a gas (such as sterilized air) may be provided so that bubbles are injected into the fluid at or near the centrifugal pump created by an agitator, such as impeller 118 within the container 140. In some embodiments, the injector may comprise an injector conduit or tube 142 which can be connected to a gas supply external to the bioreactor (see, e.g., FIGS. 25, 26), and connected to any wall thereof. For instance, such tube 142 can be connected to the cover 114 of the bioreactor 100 as shown in FIGS. 25 and 26. Alternatively, tube 142 can be connected to the bioreactor 100 at a location along the base of the bioreactor adjacent to the location of the container 140, as shown in FIG. 24.

In some embodiments, as shown in FIG. 24, the outlet of the tube 142 for supplying gas to the liquid of the bioreactor 100 is within or in fluid communication with an interior of the container 140, and thus located in the fluid path between the inlet I and outlet O. However, it is also possible for the outlet of the tube 142 to be located within the central chamber 126, such as when the tube 142 is passed through another wall or surface of the bioreactor 100. In FIG. 25, the tube 142 is shown to be passing through the cover 114 into the lower portion of the central chamber of the bioreactor proximate the container 140, and in FIG. 26, the tube 142 is shown entering the container 140, such that an open distal end of the tube may transmit liquid directly to, or is in fluid communication directly with, the interior compartment of the container.

In any of the embodiments, oxygen-containing gas (such as air) injected into the bioreactor 100 via tube 142 forms relatively large size of bubbles in the fluid since the tube simply includes an unobstructed open end. Alternatively, smaller bubbles can be generated with the use of a device such as a sparger is used along with customized nozzles and related oscillator systems. In either case, as a result of the positioning of the open end or nozzle of the tube 142, these larger "macrobubbles" or smaller "microbubbles" (Size 1) are released to a location before which they will encounter the turbulence and shearing action created by the agitator (e.g., rotating impeller 118 serving as agitator) forming the pump for the bioreactor 100. This agitation serves to divide the larger macrobubbles into more numerous bubbles having a smaller size, or "microbubbles" or to divide the smaller microbubbles into yet more numerous bubbles having yet smaller size (Size 2). The formation of more numerous bubbles may further result from the increased residence time of the gas bubbles within the agitator container 140 (if present) as well as the speed and design of the agitator.

As a result of the rotation of impeller 118, these microbubbles may then be carried away by the flowing liquid, such as radially outwardly and upwardly in the illustrated bioreactor 100. It can be appreciated by one skilled in the art that the opposite flow pattern would result if the pump direction reversed.

Given their smaller size, the microbubbles are better able to pass into and through channels formed by the spacer layers 122b and the adjacent cell immobilization layers 122a (or other available paths) of the fixed bed 122. This serves to further enhance the oxygenation of the cells being grown in the bed, without a corresponding need to increase the speed of the impeller 118 and the resulting liquid flow rate. Moreover, the release of the gas into or near the agitator container 140 and the resulting flow avoids the creation of deleterious air pockets in the bioreactor 100, which are notoriously difficult to remove without halting the bioreactor operation.

However, in another embodiment of the disclosure, as the (Size 2) microbubbles pass through the structured fixed bed 122, they are further divided into smaller and more numerous microbubbles (Size 3). For example, this may occur as the bubbles enter into the channels formed in the fixed bed 122, such by the spacer layers 122b and/or the adjacent cell immobilization layers 122a and pass through all available tortuous (or labyrinthian) paths provided. As they travel, the larger bubbles tend to break up or divide into still yet smaller microbubbles before exiting the fixed bed 122. Consequently, the gas transfer during residence time in the fixed bed 122 is increased and the bubbles emanating from the bed once having passed therethrough are actually still even smaller in size (and thus more numerous) that at a point of entry, as a result of shearing forces caused by the bubbles engaging the mesh of the spacer layer 122*b* in the illustrated embodiment.

As indicated in FIGS. 25 and 26, in the illustrated version of a bioreactor 122, liquid exiting from the bed 122 travels to the central chamber 126 where it flows directly along the inner surface of the wall thereof, which may be formed by tube 128. The liquid level in the central chamber 126 can be lower than the liquid level in the bed 122. A thin layer or "film" of liquid may be created, which flows downwardly (in this embodiment) while passing through the central chamber 126. In some embodiments, this gas-liquid interface serves to increase the volume of the liquid exposed to gas (e.g., air), prior to it being returned to the first chamber 116 and eventually re-entering the fixed bed 122 as a result of the pumping action created by agitator. In some embodiments, this can allow for more oxygen transfer which may be needed for larger sizes of bioreactor or otherwise to increase cell growth rates or adjust process parameters based on the biologic being produced. FIG. 27 illustrates a further example of a bioreactor 100, which includes multiple stacked beds (two shown, but any number could be provided). In this arrangement, the gas injector is arranged to provide a fresh supply of gas to a location at the inlet end of each bed 122 in the stack, which may be achieved using individual tubes 142 passed through a corresponding portion (e.g., housing 112*a*) or a manifold 144 connected to a gas supply. The bubbles may be larger in size upon introduction, and then once having passed through the corresponding bed 122 are actually still even smaller in size that at a point of entry, as a result of shearing forces caused by the bubbles engaging the mesh of the spacer layer 122*b* in the illustrated embodiment. Alternatively, the bubbles may be smaller due to use of a sparger/nozzle system perhaps with an oscillator so that they do not create a cloud an inlet of fixed bed section.

Additionally (or alternatively), increasing the gas transfer coefficient, or kLa, value may be achieved by increasing or extending the distance, and thus the time during which, the liquid media travels while in contact with gas phase prior to returning to the fixed bed. In one possible embodiment, this extended flow pattern is achieved by providing a flow extender (which for purposes of this disclosure means a structure with an increased surface area over which the liquid must flow in order to increase the residence time in contact with gas, and may be formed of any suitable material, such as polymer, metal, or the like). It may also be desirable, as discussed further below, to combine the flow extender with a flow disruptor to cause turbulence, which minimizes the diffusion layer normally formed at the gas/liquid border. One skilled in the art will appreciate that this introduction of a flow extender and/or flow disrupter can be applied to any fixed bed bioreactor design including an unstructured packed bed bioreactor. As further shown in FIG. 28, the flow extender 150 may be provided in a modified form with a series of concentric ledges, or steps 158, over which liquid flows or cascades while moving radially. This not only increases the residence time of the liquid, but also generates a measure of turbulence as the liquid changes direction while flowing along and/or over the steps 158.

In a case where the bed 122 is in the outer (annular) chamber 120, the extender 150 also may be located within the central chamber 126, as shown in FIG. 29. In this example, the extender 150 comprises a maze-like structure formed of segmented walls 180 that may be spaced vertically and circumferentially to create a tortuous flow in a film of liquid exiting the bed 122 and entering chamber 126 from above. This creates the desired disruption of the normally occurring diffusion layer and thus causing the liquid to interface with the gas in chambers 124, 126, thereby improving the gas transfer. The structure of the extender 150 for causing the flow disruption could also take the form of pins, forks, or the like. As shown in FIG. 30, the extender 150, such as for example one comprising pins 182 or any other disruptive structures, may also be provided in chamber 120, when the bed 122 is located in central chamber 126.

FIG. 31 shows an embodiment of a lift 403 for transporting various parts of the system according to one aspect of the current disclosure. The lift comprises wheels 401 to transport the various parts to be installed, and a holder 402 (not shown) to grasp the various parts.

FIGS. 32 and 33 illustrate alternate embodiments of a modular bioreactor 400 including fixed beds 496. In some embodiments, the base part 430 and cover part 470 can be adapted for connecting with an outer casing 492, which creates a gap or space with the periphery of the intermediate parts 450. In some embodiments, the gap G or space may be used for providing a heating or cooling effect to control the temperature of the beds associated with the intermediate parts 450. The gap G or space may also simply supply insulation of the walls of the intermediate area of the bioreactor which are close to growing cells within the bed and likely to be sensitive to temperature variations. This insulation acts to prevent heat which is applied to the bottom of the base part 430 of the bioreactor from extending up to the adhered cells in the bed(s) 496.

FIG. 32 also illustrates the possible use of sparging in the bioreactor, which may be provided in any disclosed embodiment. In the illustrated arrangement, the sparging is provided by a sparger 494 located in the fifth chamber 428. The bubbles generated as a result may thus flow upwardly countercurrent to the return fluid flow.

These figures, and perhaps FIG. 33 best, also show that the intermediate parts 450 may engage internal tubes 436, which are fluid impervious to thus provide the chamber 428 for returning flow to the base part 430, where it may be agitated and returned to enter the beds from below and flow upwardly therethrough (in any embodiment disclosed). These tubes 436 may be provided such that one tube corresponds to each fixed bed 496 present, as shown, and two intermediate parts 450 engage each tube 436 (e.g., one from below and one from above). However, in this or any other disclosed embodiment, it should be appreciated that the innermost surface of the fixed bed, such as the innermost spiral wrap of a spiral bed, may be made to perform a similar function by making it or otherwise conditioning it so as to be impervious to fluid. For instance, the surface maybe coated with a fluid-impervious or hydrophobic material, such that it still retains the fluid in the bed(s) and maintains a distinct, return flow of fluid through the central column formed by chamber 428.

FIG. 34 is a schematic overview of filter unit 500 such as a clarification filter provided with an outlet line 501 having a vertical section 502 parallel to said filter, and which allows for safe priming and venting of said filter unit 500 prior to use. Priming solution is providing via an inlet line 503 in connection to the filter 500, by means of a pump 504. The filter is also in liquid connection with an outlet line 501 which as described has a vertical section 502. A vent line 505 connected to the top of the filter 500 is open during the addition of the priming solution. Opening and closing of the vent line 505 can be regulated by an automated pinch valve 506. It will be clear to a skilled person that also other options known in the art are suited to regulate the vent line. Optionally, an automated (pinch) valve 507, 508 may be present at the inlet 503 and/or in the outlet line 501. The vent line 505 can be provided with a digital liquid detector 509 to monitor the liquid in the vent line. The inlet line 503 can be provided with a digital pressure sensor 510 to monitor the pressure in the inlet line 503. A vent 511 is present at the end of the vent line 505 and the vent line 505 ends in a bottle 512 to recover any excess of priming solution.

The system as described in FIG. 34 is implemented in the system as shown in FIGS. 6A and 6B, more specifically in the process chamber 018. It will be clear to a person skilled in the art that said principle can also be applied to other filters that require priming and venting and that are present in any of the other chambers of the system.

The invention claimed is:

1. A bioreactor cabinet configured to be incorporated in a biomolecule production system, the biomolecule production system including a bioreactor chamber adapted to receive the bioreactor cabinet, wherein said bioreactor cabinet is a mobile bioreactor cabinet adapted to receive a bioreactor, wherein said bioreactor cabinet comprises a bioreactor docking station adapted to receive the bioreactor, wherein at least one side wall of a plurality of sidewalls of said bioreactor cabinet includes a connector adapted to mate with a corresponding portion of the bioreactor chamber and to couple the bioreactor cabinet to the bioreactor chamber of the production system, allowing the transmission of power, signals or data between the bioreactor cabinet and the bioreactor chamber when the bioreactor cabinet is paired with the bioreactor chamber of the biomolecule production system.

2. The bioreactor cabinet according to claim 1, wherein said bioreactor cabinet is adapted to dock into said biomolecule production system comprising an additional connection for physically securing said bioreactor cabinet to said bioreactor chamber.

3. The bioreactor cabinet according to claim 2, wherein said additional connection is one or more magnetic connections.

4. The bioreactor cabinet according to claim 3, wherein said connector and one or more magnetic connections are provided on the same wall of said bioreactor cabinet.

5. The bioreactor cabinet according to claim 1, wherein said bioreactor cabinet is a wheeled cabinet.

6. The bioreactor cabinet according to claim 1, wherein said bioreactor cabinet includes a handle connected to the front wall of said bioreactor cabinet.

7. The bioreactor cabinet according to claim 1, wherein said bioreactor docking station resides inside said bioreactor cabinet, guarded from the outside environment by said bioreactor cabinet.

8. The bioreactor cabinet according to claim 1, wherein said bioreactor docking station comprises a removable height adjuster for allowing positioning of the bioreactor when present.

9. The bioreactor cabinet according to claim 1, wherein said plurality of sidewalls of the bioreactor cabinet are provided with positioning means for allowing the alignment of said platform with a biomolecule production system.

10. The bioreactor cabinet according to claim 9, wherein said positioning means are circular or cylindrical elements on a rotating axle incorporated in sockets in the plurality of sidewalls of said bioreactor cabinet.

11. The bioreactor cabinet according to claim 1, comprising a bioreactor support plate on a top surface of said bioreactor cabinet, wherein said bioreactor support plate comprises a grid and a recess adapted to receive a bioreactor surface.

12. The bioreactor cabinet according to claim 1, further comprising a bioreactor placed on said bioreactor docking station.

13. The bioreactor cabinet according to claim 12, wherein said bioreactor comprises a fixed bed for culturing cells, wherein said fixed bed is a structured fixed bed.

14. The bioreactor cabinet according to claim 12, wherein said bioreactor comprises:

a base portion having a first chamber;

an intermediate portion forming at least part of a second, outer chamber for receiving the fixed bed and at least part of a third inner chamber for returning fluid flow from the second outer chamber to the first chamber; and a cover portion for positioning over the intermediate portion.

15. System for the production of biomolecules, said system comprising a bioreactor cabinet according to claim 1.

* * * * *